US011384379B2

(12) United States Patent
Yahagi et al.

(10) Patent No.: US 11,384,379 B2
(45) Date of Patent: Jul. 12, 2022

(54) **METHOD FOR PRODUCING A PROTEIN AND DISACCHARIDE USING A *TALAROMYCES CELLULOLYTICUS***

(71) Applicant: AJINOMOTO CO., INC., Tokyo (JP)

(72) Inventors: Daiki Yahagi, Kanagawa (JP); Erika Yoshida, Kanagawa (JP); Hiroaki Fukada, Kanagawa (JP); Mitsunori Tokura, Kanagawa (JP); Uno Tagami, Kanagawa (JP); Masayuki Sugiki, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/826,656

(22) Filed: Mar. 23, 2020

(65) Prior Publication Data

US 2020/0263219 A1 Aug. 20, 2020

Related U.S. Application Data

(63) Continuation of application No. PCT/JP2018/035530, filed on Sep. 25, 2018.

(30) Foreign Application Priority Data

Sep. 25, 2017 (JP) ............................ JP2017-184180

(51) Int. Cl.

*C12P 21/00* (2006.01)
*C12N 1/14* (2006.01)
*C12N 9/42* (2006.01)
*C12P 19/12* (2006.01)

(52) U.S. Cl.

CPC ................ *C12P 21/00* (2013.01); *C12N 1/14* (2013.01); *C12N 9/2445* (2013.01); *C12P 19/12* (2013.01); *C12Y 302/01021* (2013.01)

(58) Field of Classification Search

None

See application file for complete search history.

(56) References Cited

U.S. PATENT DOCUMENTS

| | | | |
|---|---|---|---|
| 2010/0136618 A1 | 6/2010 | Fang et al. | |
| 2010/0323426 A1* | 12/2010 | Bower ........... | C12Y 302/01004 435/209 |
| 2012/0148706 A1 | 6/2012 | Yokoyama et al. | |
| 2013/0023014 A1* | 1/2013 | Yokoyama .......... | D06M 16/003 435/99 |
| 2014/0045243 A1* | 2/2014 | Znameroski ......... | C12N 9/2445 435/190 |
| 2015/0132800 A1 | 5/2015 | Ward | |
| 2016/0237466 A1 | 8/2016 | Landowski et al. | |

FOREIGN PATENT DOCUMENTS

| | | |
|---|---|---|
| JP | 9-507386 A | 7/1997 |
| JP | 11-506934 A | 6/1999 |
| JP | 2002-101876 A | 4/2002 |
| JP | 2003-135052 A | 5/2003 |
| JP | 2006-506980 A | 3/2006 |
| JP | 2008-271927 A | 11/2008 |
| JP | 2010-148427 A | 7/2010 |
| JP | 2010-227031 A | 10/2010 |
| JP | 2010-227032 A | 10/2010 |
| JP | 2015-518723 A | 7/2015 |
| JP | 2016-523552 A | 8/2016 |
| WO | WO95/17517 A1 | 6/1995 |
| WO | WO96/40970 A1 | 12/1996 |
| WO | WO2004/035070 A1 | 4/2004 |
| WO | WO2011/021616 A1 | 2/2011 |
| WO | WO2011/054899 A1 | 5/2011 |
| WO | WO2015/093467 A1 | 6/2015 |
| WO | WO2017/217453 A1 | 12/2017 |

OTHER PUBLICATIONS

Alignment of SEQ ID No. 18 of US20130023014 to SEQ ID No. 23 (Year: 2013).*

Kim et al. Biotechnology and Bioprocess Engineering. 2003, vol. 8: 210-212 (Year: 2003).*

Benocci et al. Biotechnol Biofuels. 2017; 10: 152. Published online Jun. 12, 2017. (Year: 2017).*

Inoue et al. Biotechnol Biofuels 7, 151 (2014) (Year: 2014).*

Bornscheuer et al. Curr Protoc Protein Sci. Nov. 2011;Chapter 26:Unit26.7 (Year: 2011).*

Inoue et al. J Ind Microbiol Biotechnol (2013) 40:823-830 (Year: 2013).*

International Preliminary Report on Patentability for PCT Patent App. No. PCT/JP2018/035530 (dated Mar. 31, 2020) with English translation thereof.

Murray, P. G., et al., "Molecular cloning, transcriptional, and expression analysis of the first cellulase gene (cbh2), encoding cellobiohydrolase II, from the moderately thermophilic fungus *Talaromyces emersonii* and structure prediction of the gene product," Biochem. Biophys. Res. Comm. 2003;301:280-286.

Kurasawa, T., et al., "Induction of Cellulase by Gentiobiose and Its Sulfur-Containing Analog in Penicillium purpurogenum," Appl. Environmen. Microbiol. 1992;58(1):106-110.

Pitson, S. M., et al., "Induction and carbon souice control of extracellular beta-glucosidase production in Acremonium persicinum," Mycol. Res. 1999;103(2):161-167.

Collins, C. M., et al., "Molecular cloning and expression analysis of two distinct beta-glucosidase genes, bg1 and aven1, with very different biological roles from the thermophilic, saprophytic fungus *Talaromyces emersonii*," Mycol. Res. 2007;111:840-849.

(Continued)

*Primary Examiner* — Christian L Fronda

(74) *Attorney, Agent, or Firm* — Cermak Nakajima & McGowan LLP; Shelly Guest Cermak

(57) ABSTRACT

A method for producing an objective protein and a method for producing a disaccharide are provided. An objective protein is produced by culturing *Talaromyces cellulolyticus* in a culture medium containing an expression inducer such as gentiobiose. A disaccharide is produced from a saccharide raw material by enzymatic conversion using a disaccharide synthesizing enzyme.

18 Claims, 25 Drawing Sheets

Specification includes a Sequence Listing.

(56) References Cited

OTHER PUBLICATIONS

Sternberg, D., et al., "Induction of Cellulolytic Enzymes in Trichoderma reesei by Sophorose," J. Bacteriol. 1979;139(3):761-769.
Nisizawa, T., et al., "Inductive Formation of Cellulase by Sophorose in Trichoderma viride," J. Biochem. 1971;70:375-385.
Fang, X., et al., "Lactose Enhances Cellulase Production by the Filamentous Fungus *Acremonium cellulolyticus*," J. Biosci. Bioeng. 2008;106(2):115-120.
International Search Report for PCT Patent App. No. PCT/JP2018/035530 (dated Dec. 18, 2018).
Murray, F. R., et al., "Isolation of the glucose oxidase gene from Talaromyces flavus and characterisation of its role in the biocontrol of Verticillium dahliae," Curr. Genet. 1997;32(5):367-375.
Murray, P., et al., "Expression in Trichoderma reesei and characterisation of a thermostable family 3 beta-glucosidase from the moderately thermophilic fungus *Talaromyces emersonii*," Protein Expression and Purification 2004,38(2):248-257.
Communication Pursuant to Rule 164(1) EPC from European Patent App. No. 18858730.7 (dated Jun. 1, 2021).

* cited by examiner

[Fig. 1]
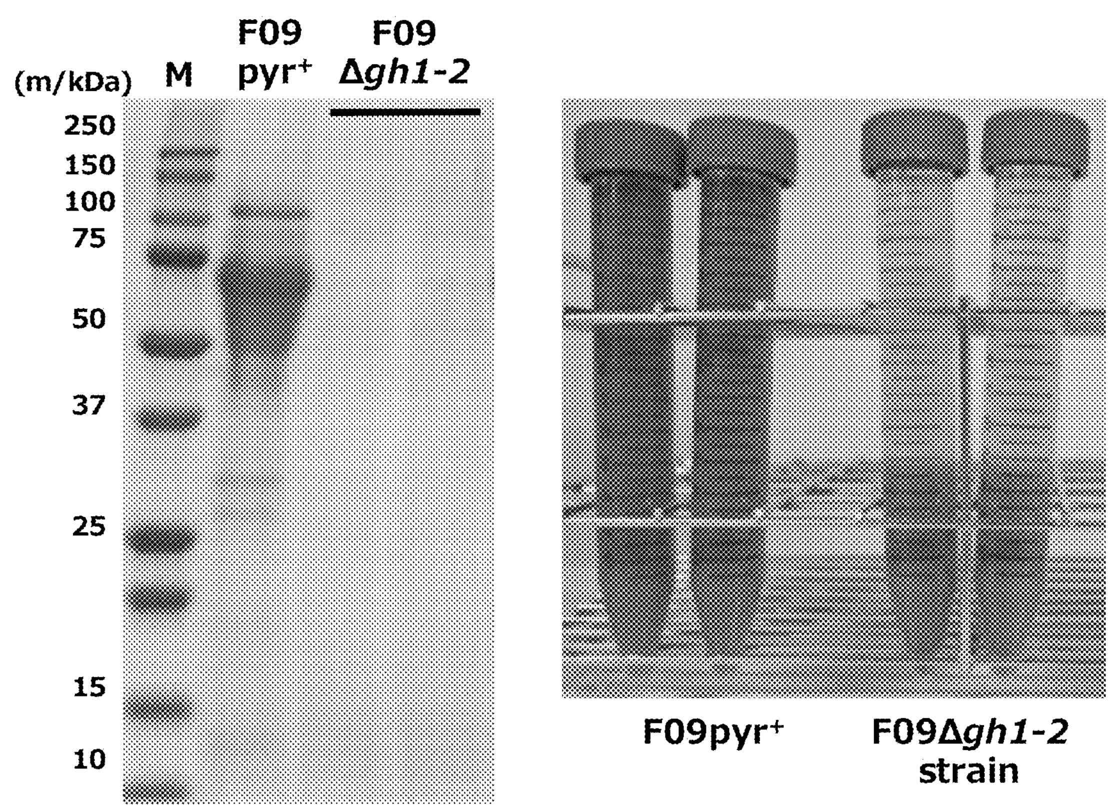

[Fig. 2]
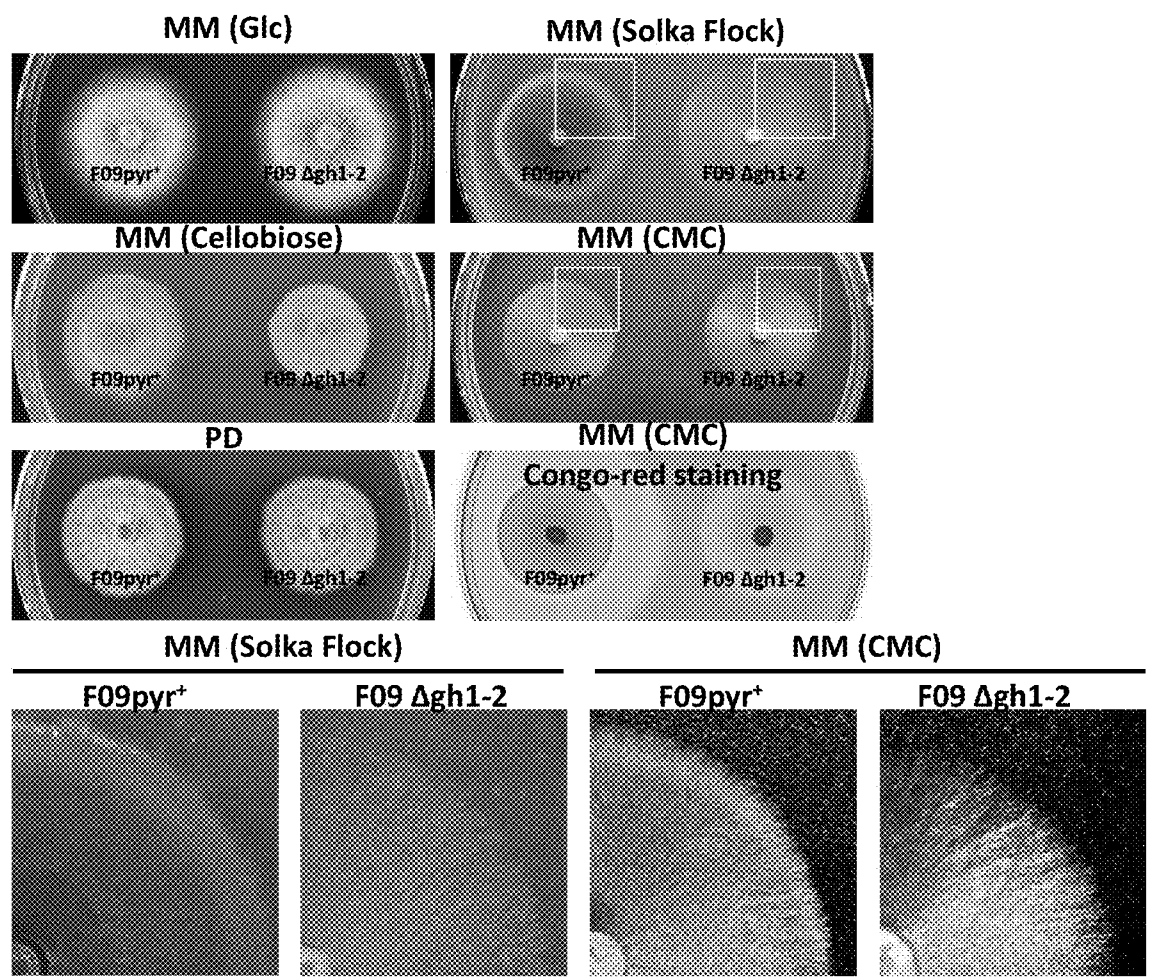

[Fig. 3]
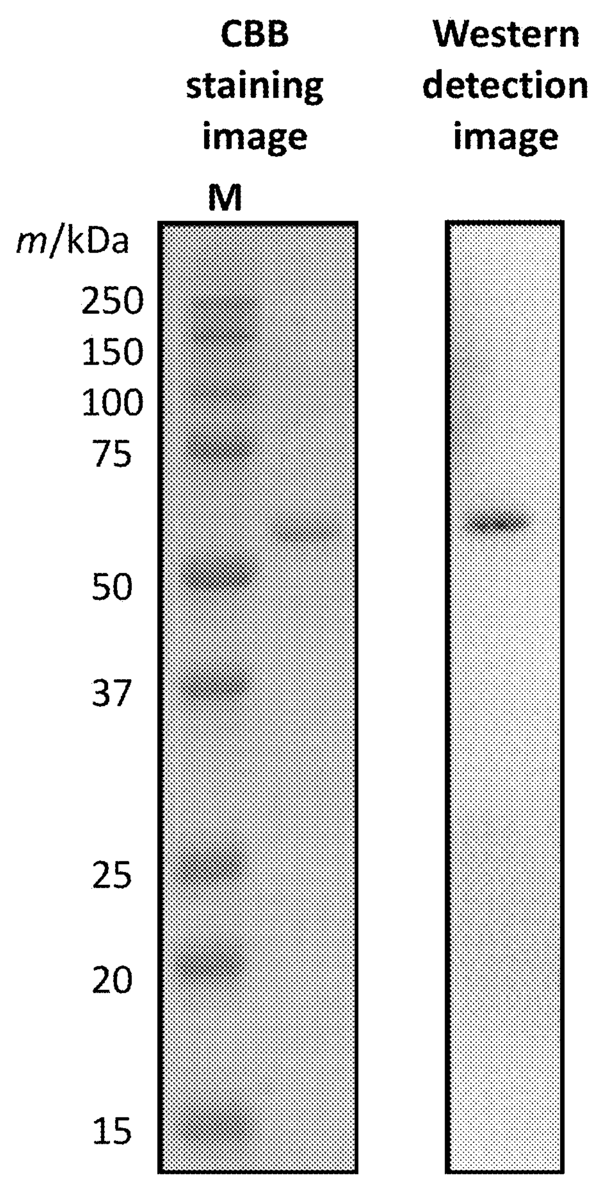

[Fig. 4]
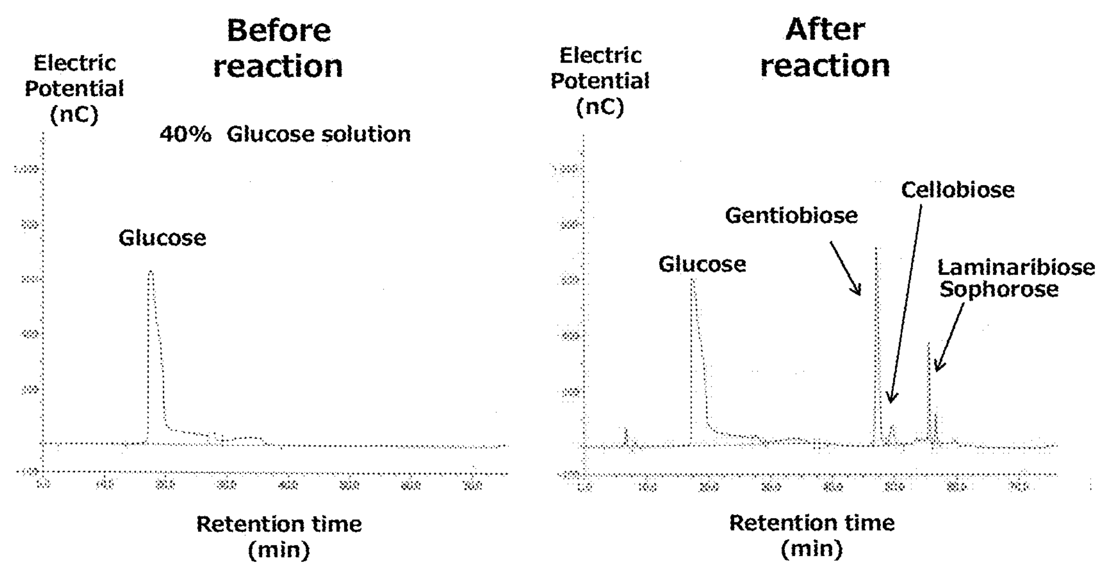

[Fig. 5]
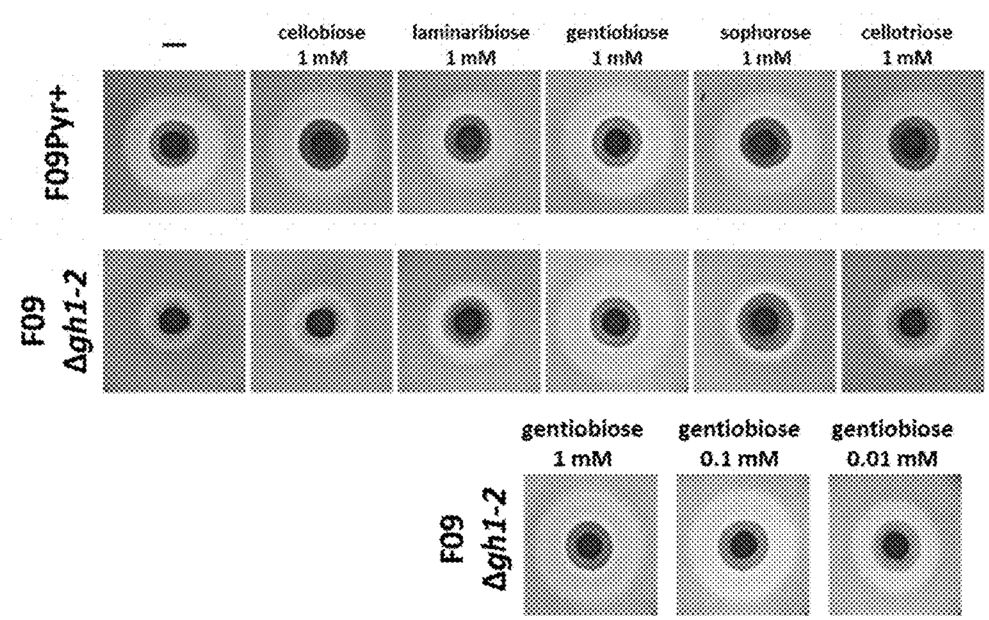

[Fig. 6]
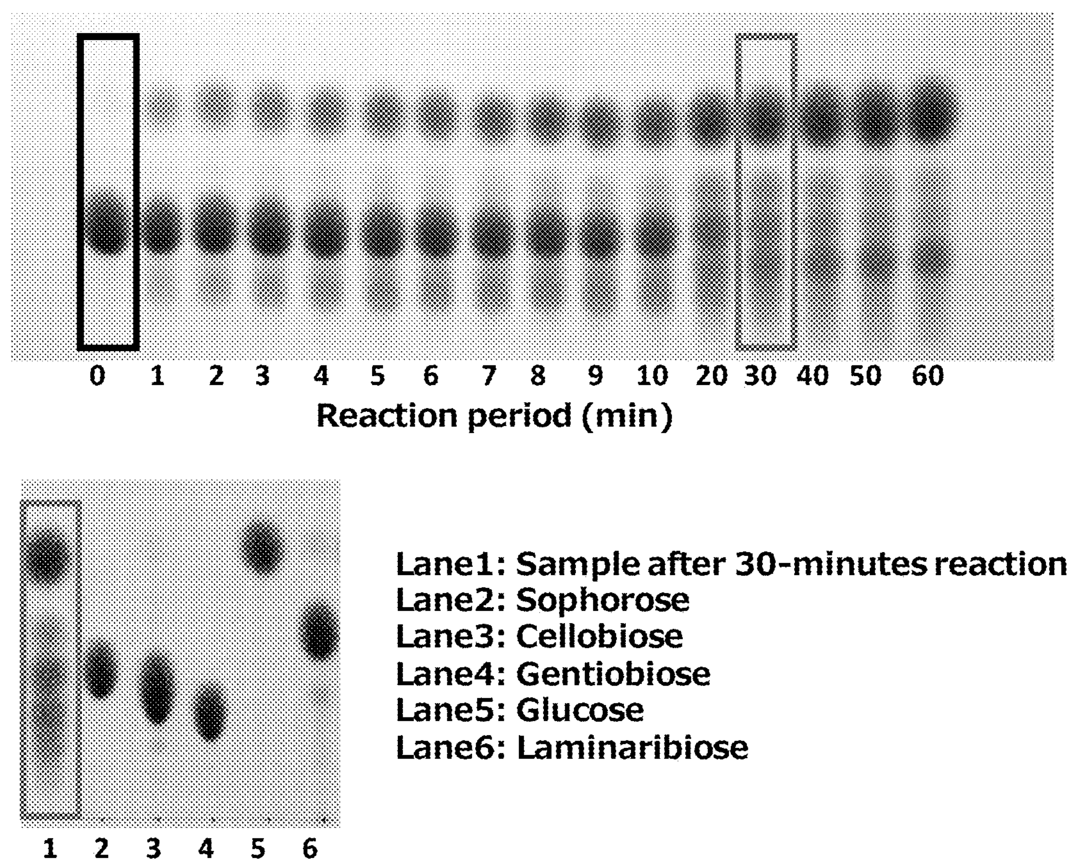

[Fig. 7]
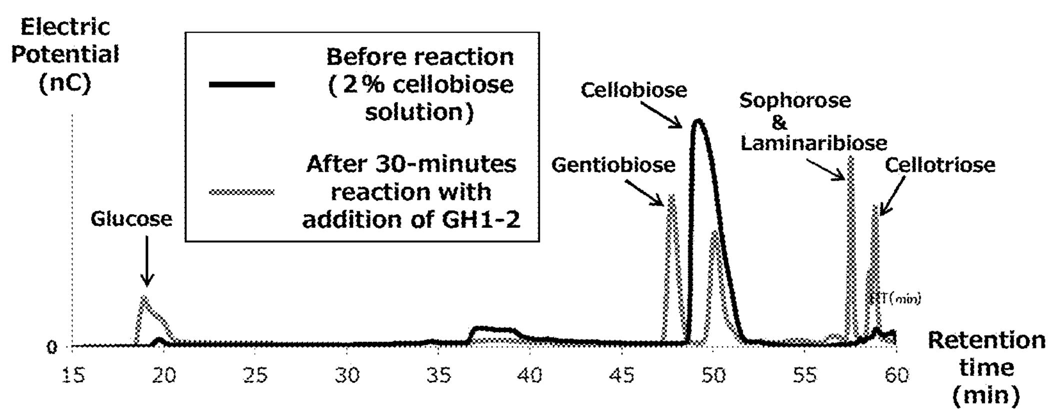

[Fig. 8]
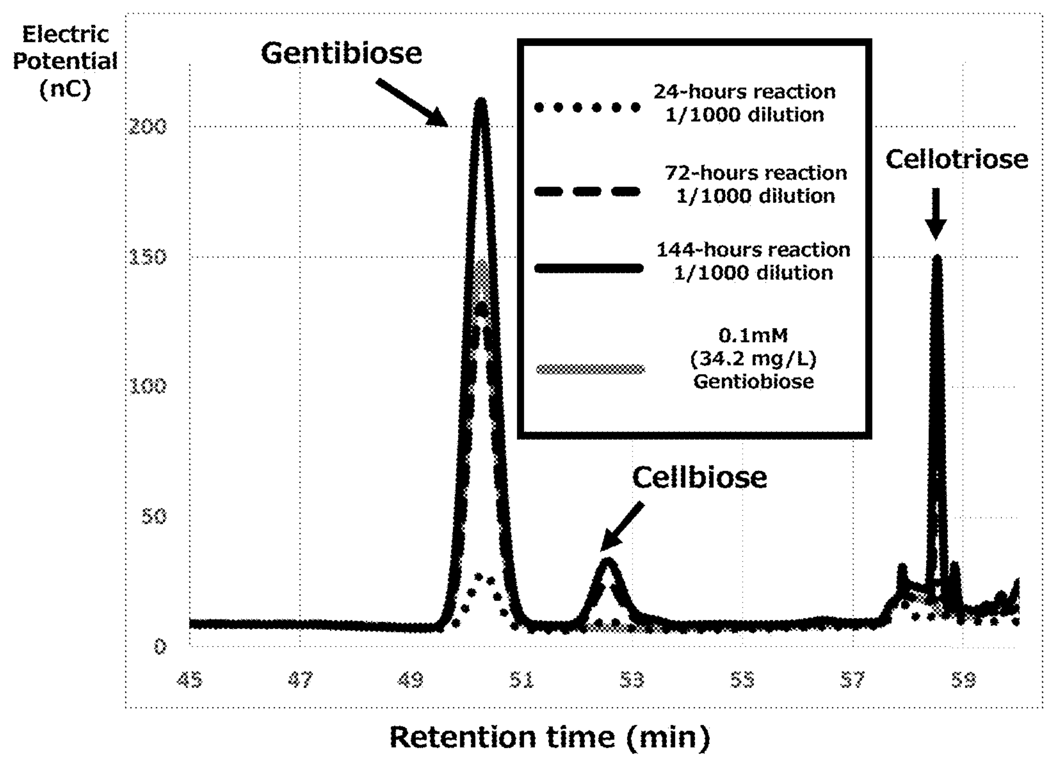
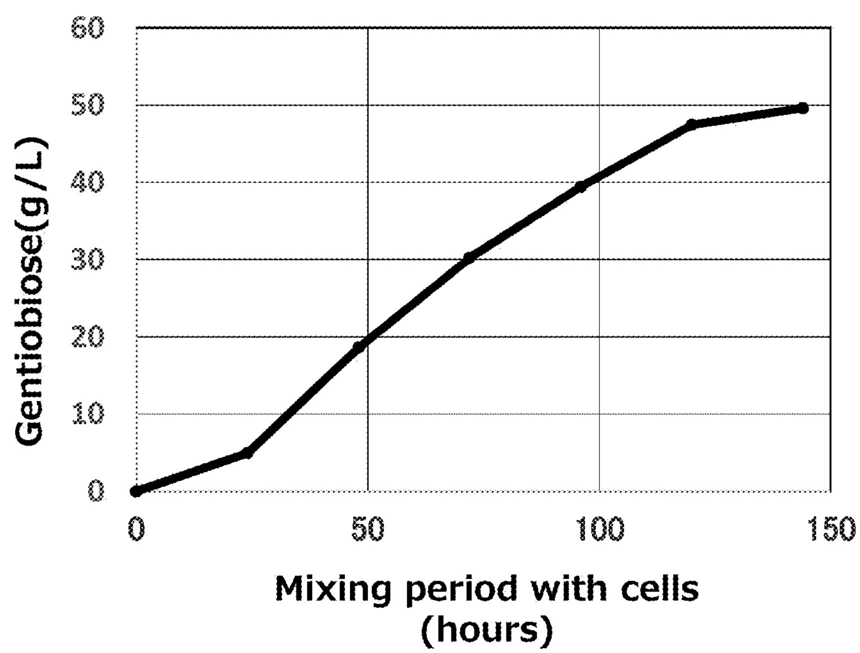

[Fig. 9]
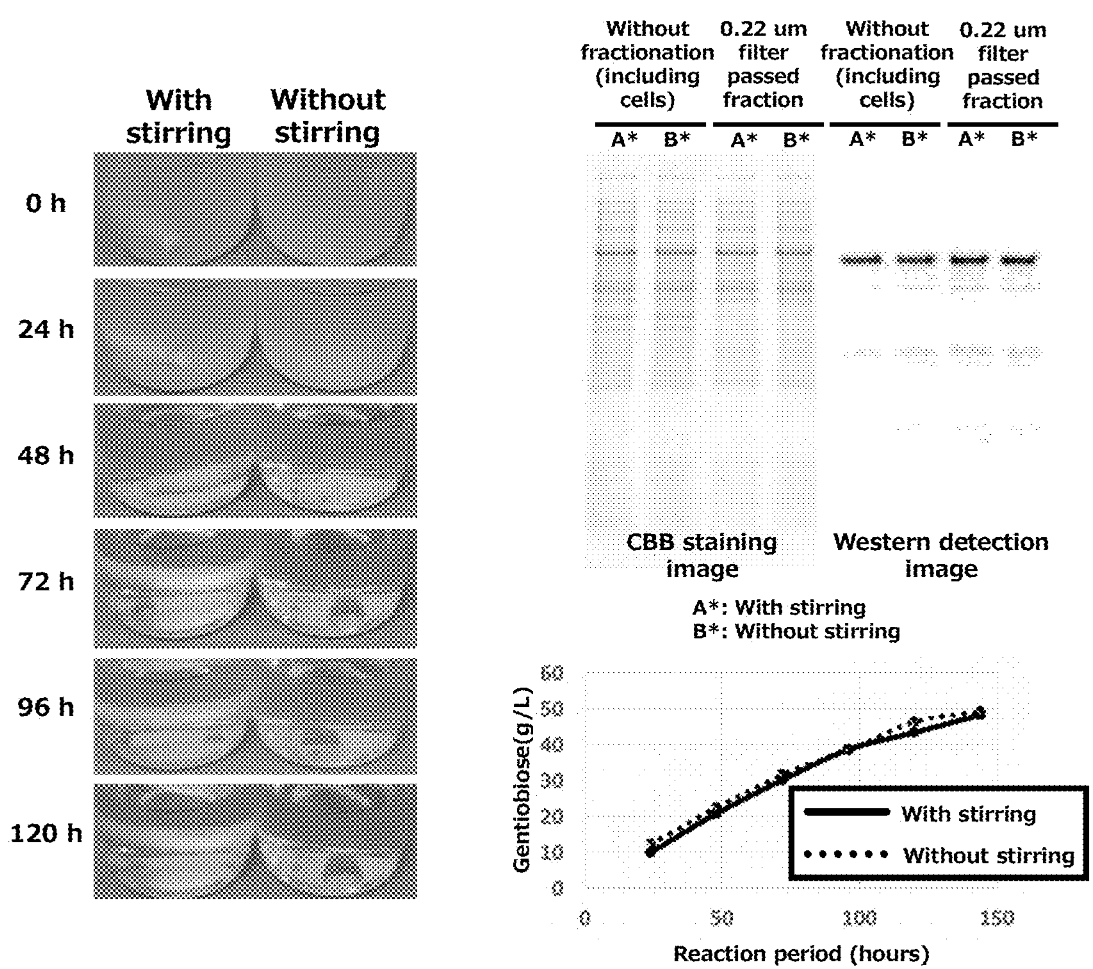

[Fig. 10]
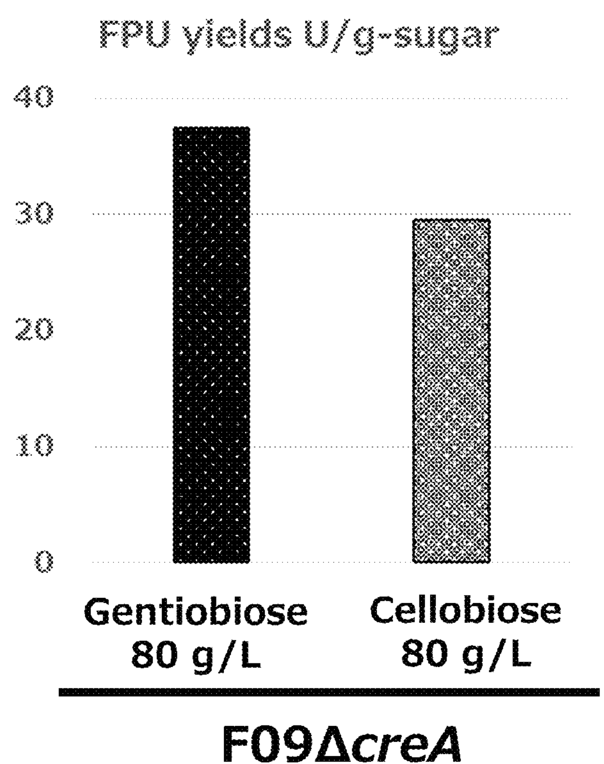

[Fig. 11]
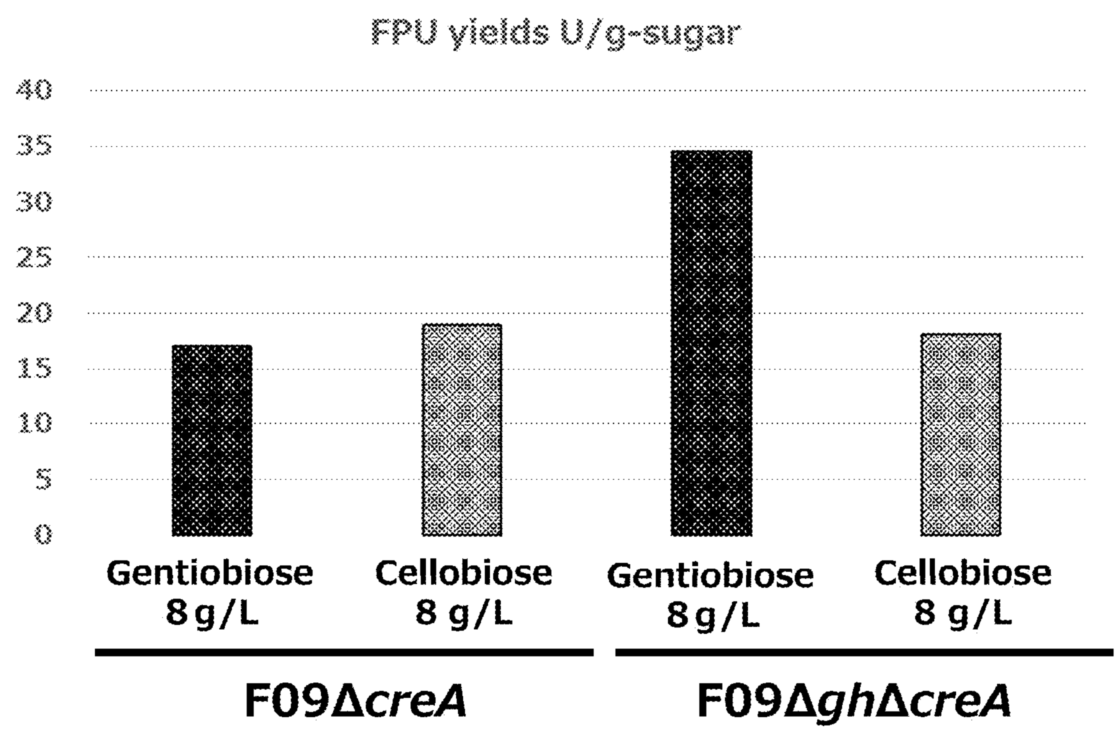

[Fig. 12]
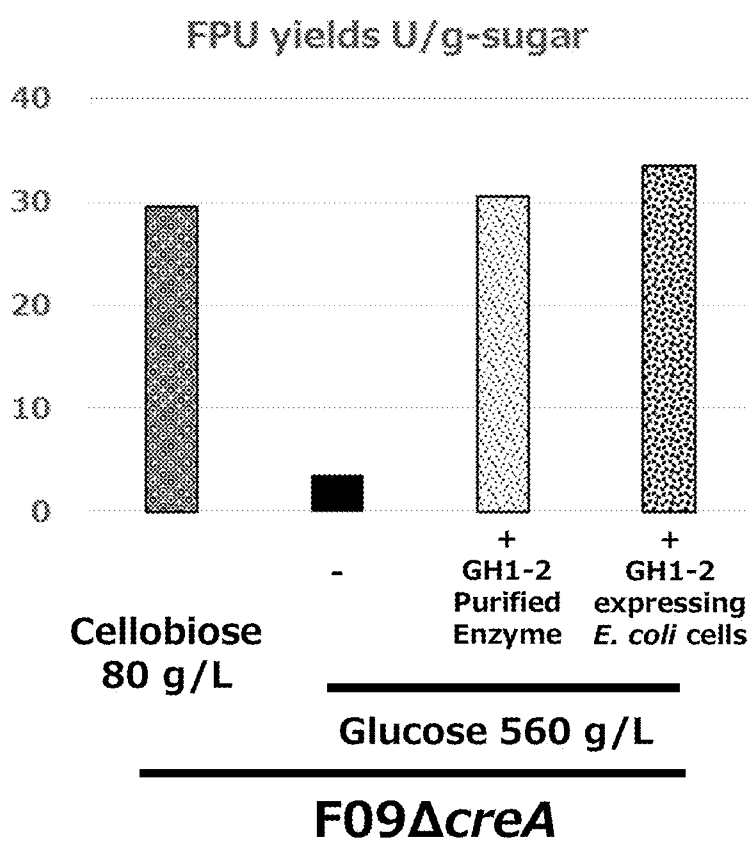

[Fig. 13]
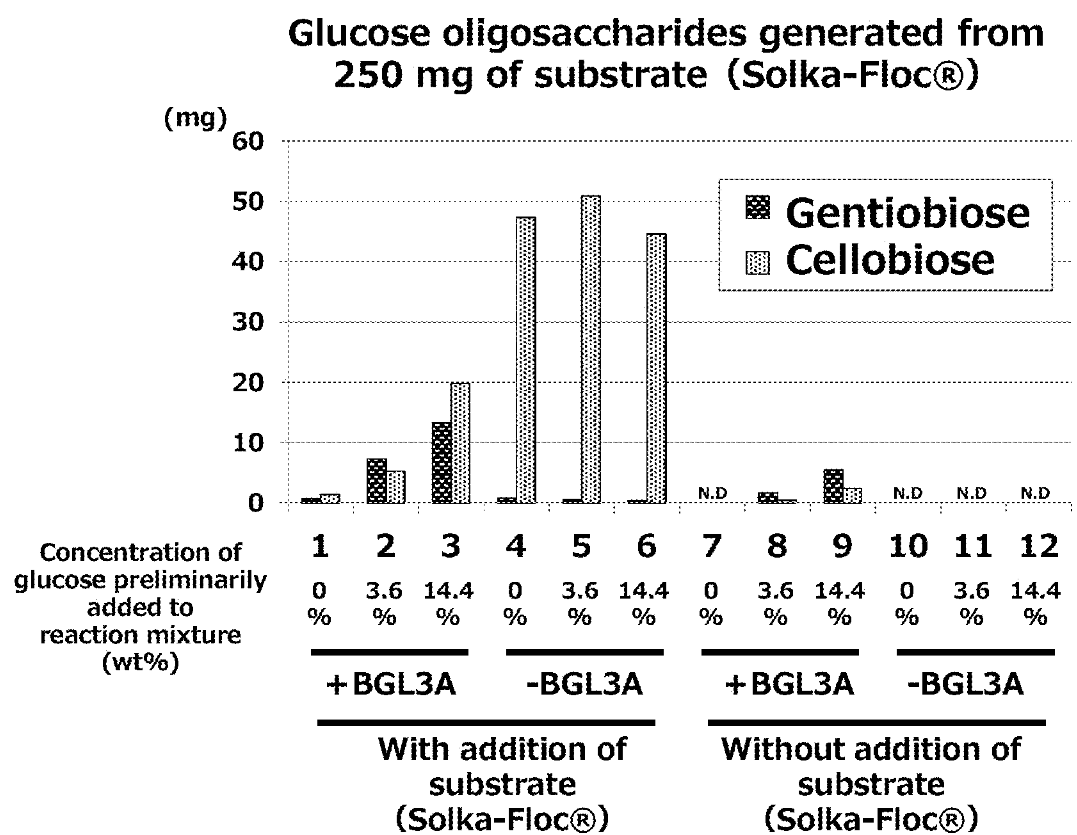

[Fig. 14]
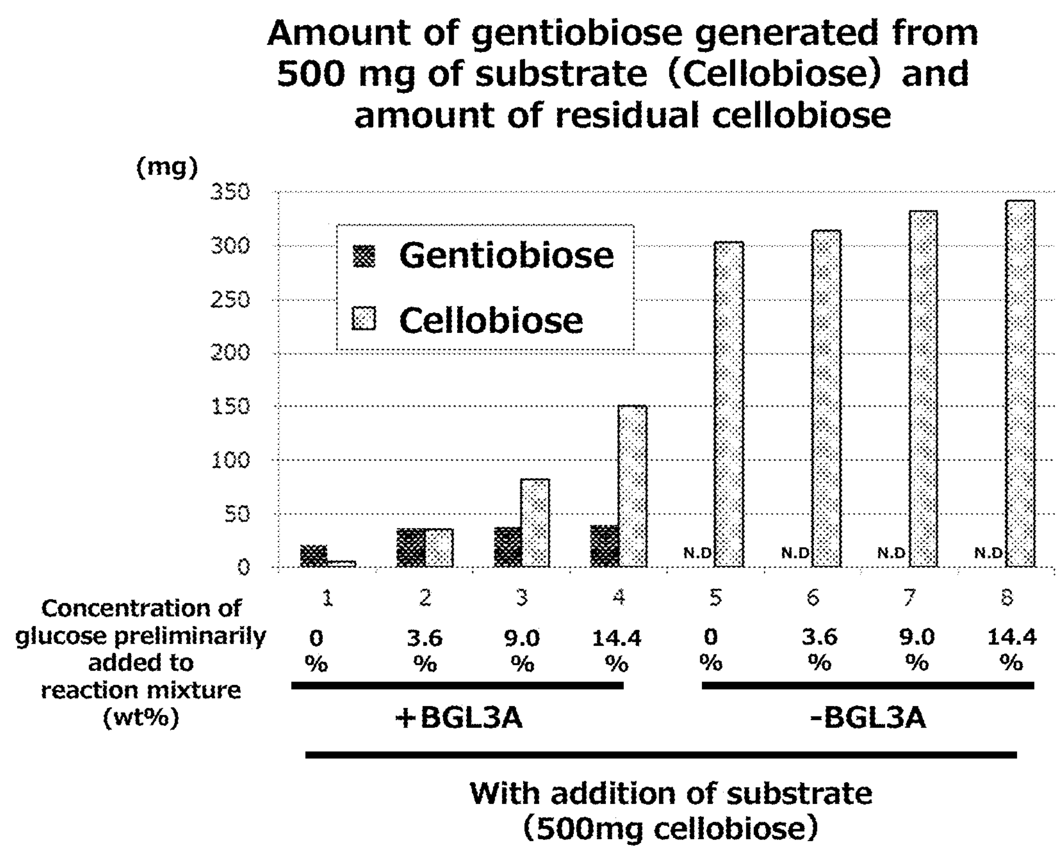

[Fig. 15]
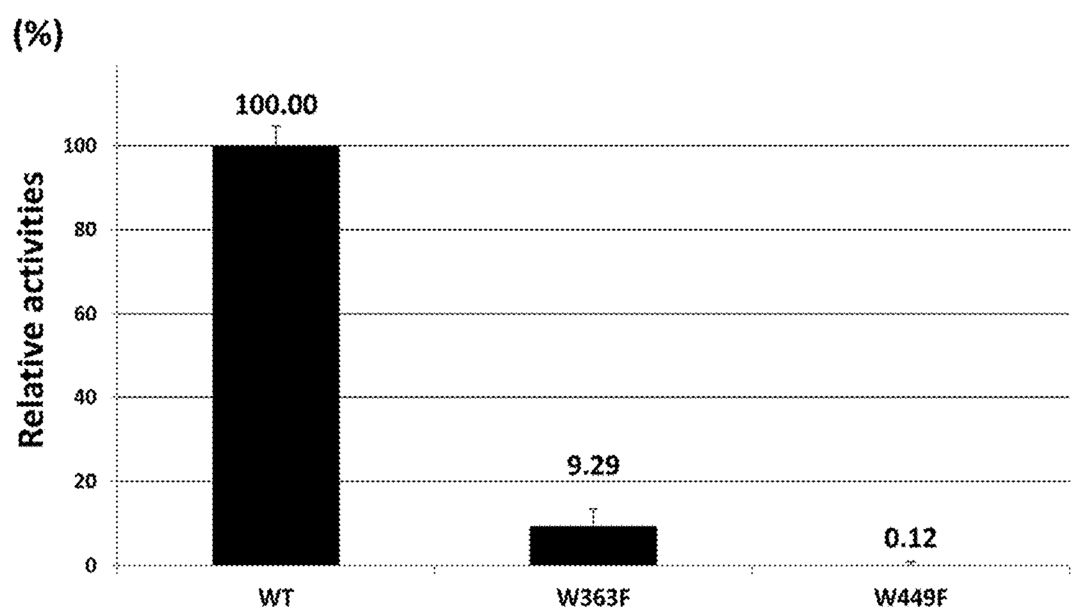

[Fig. 16]
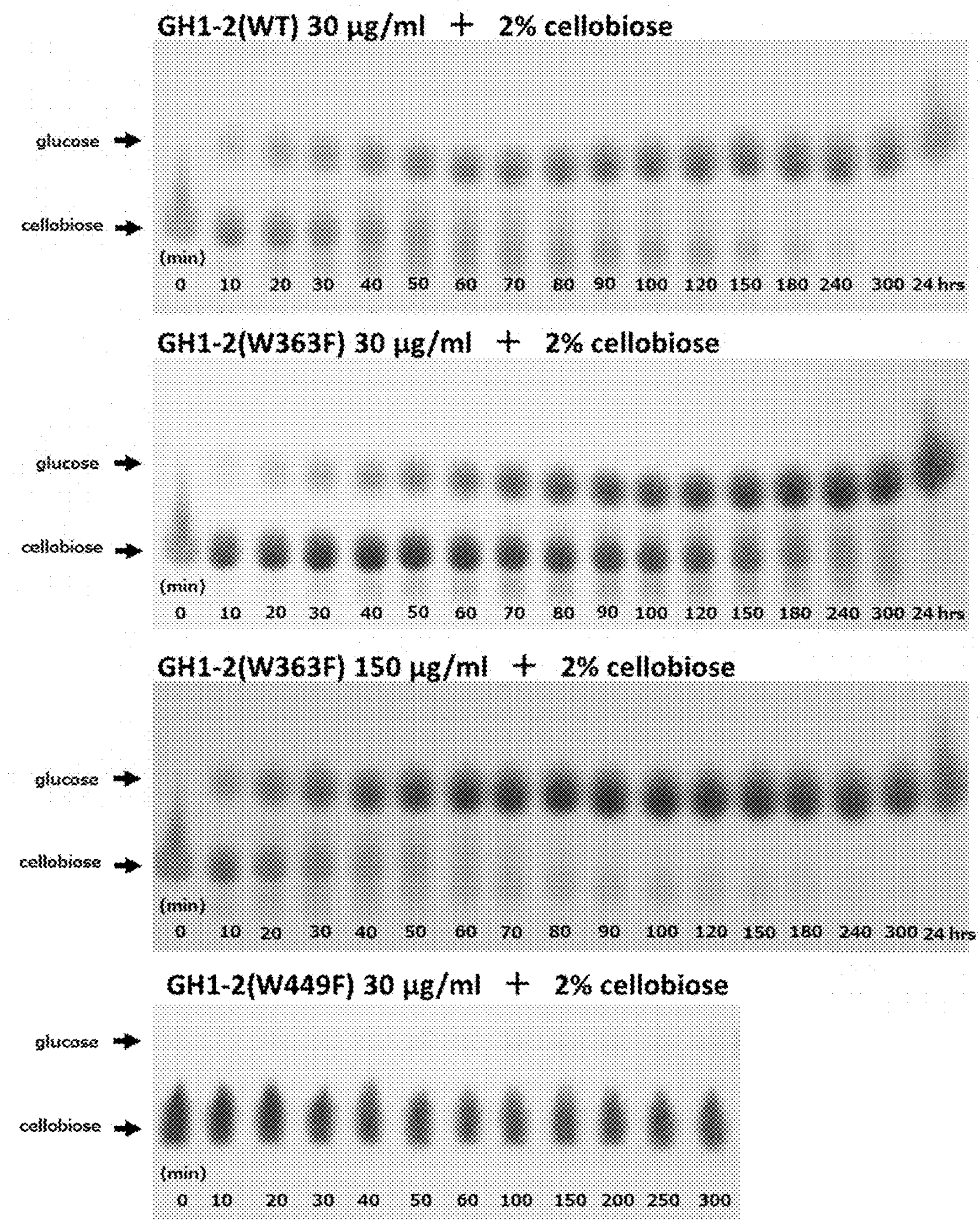

[Fig. 17]
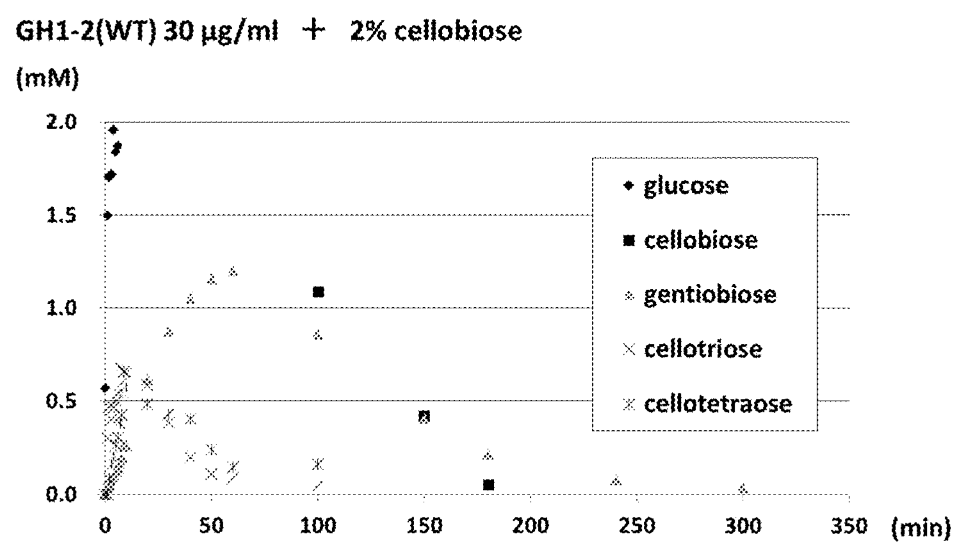

[Fig. 18]
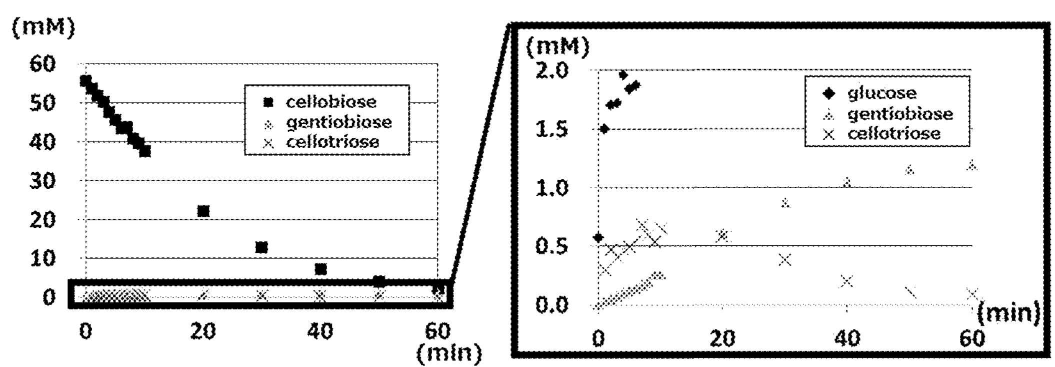
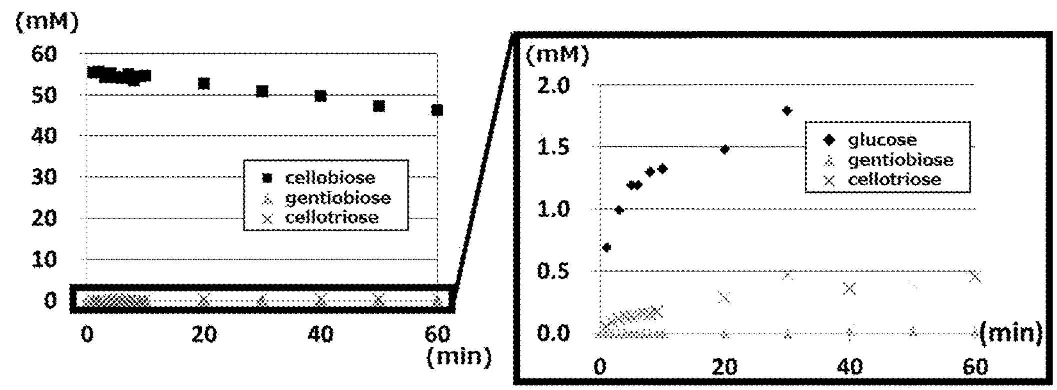

[Fig. 19]
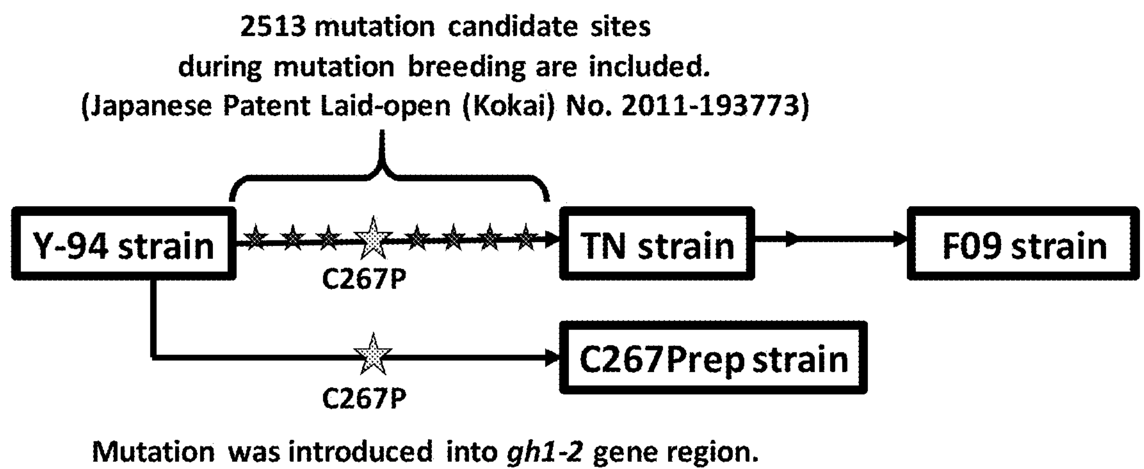

[Fig. 20]
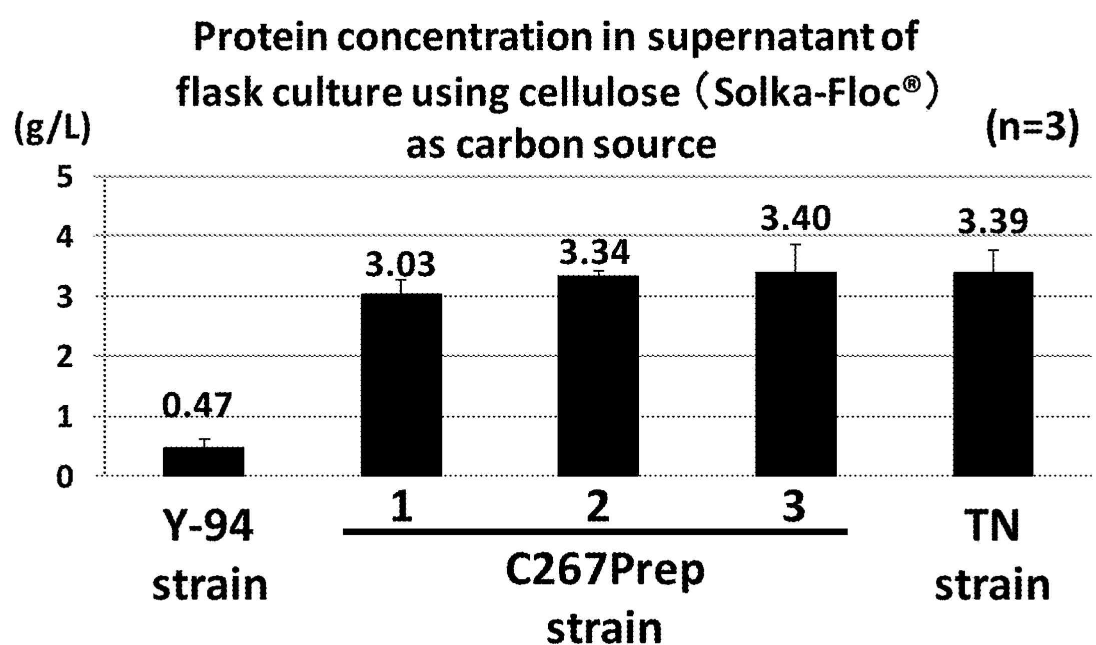

[Fig. 21]
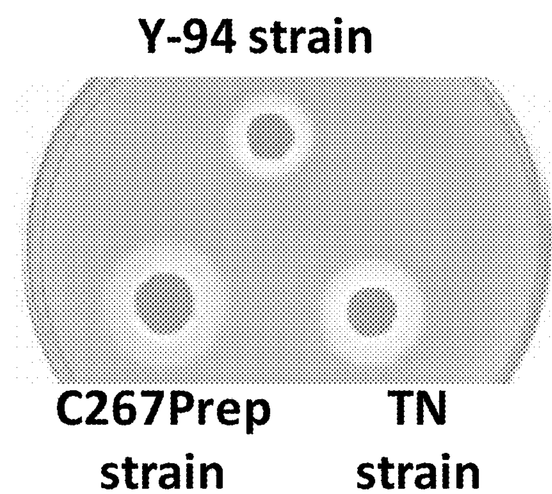

[Fig. 22]
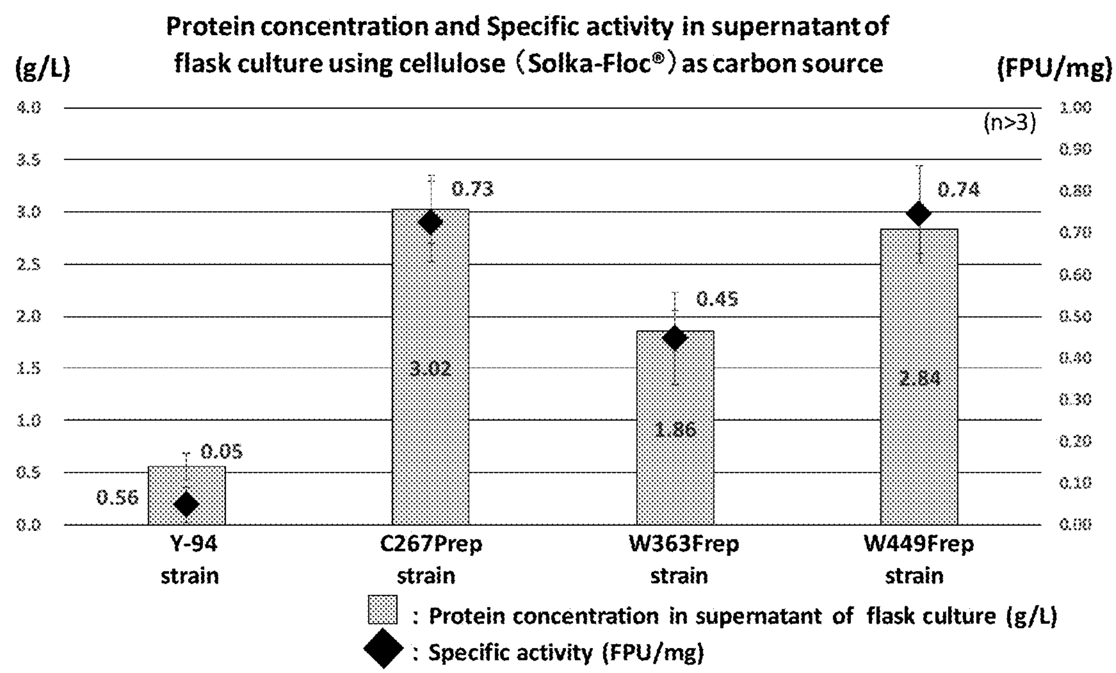

[Fig. 23]
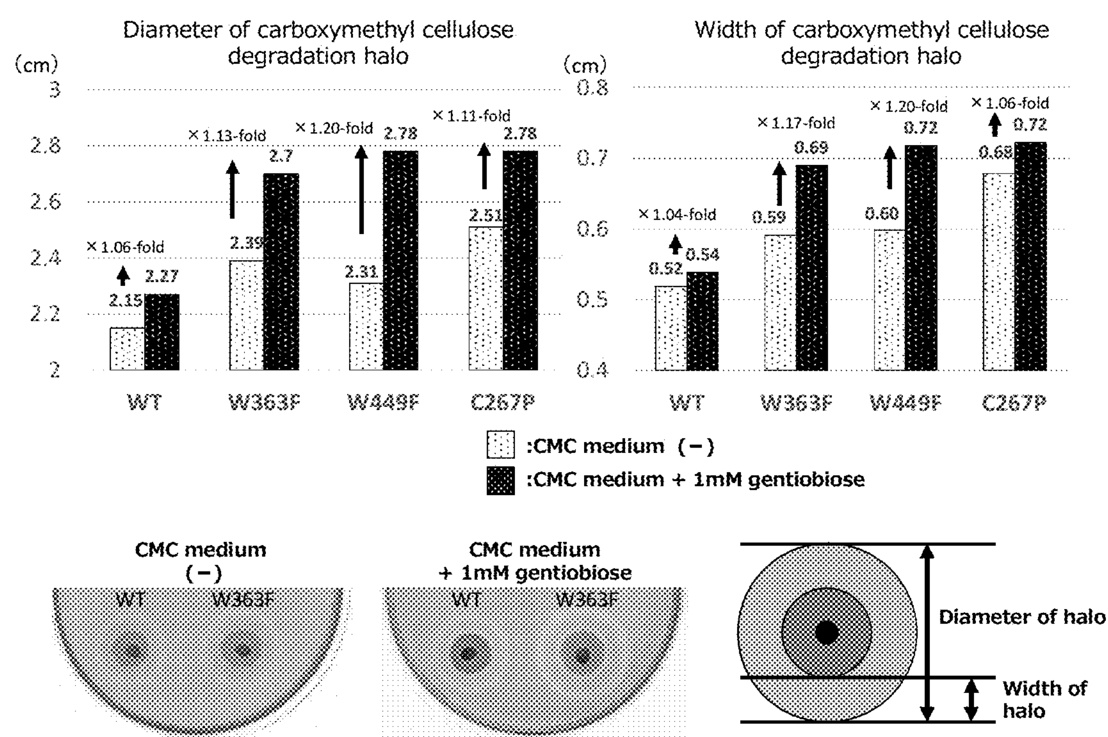

[Fig. 24]
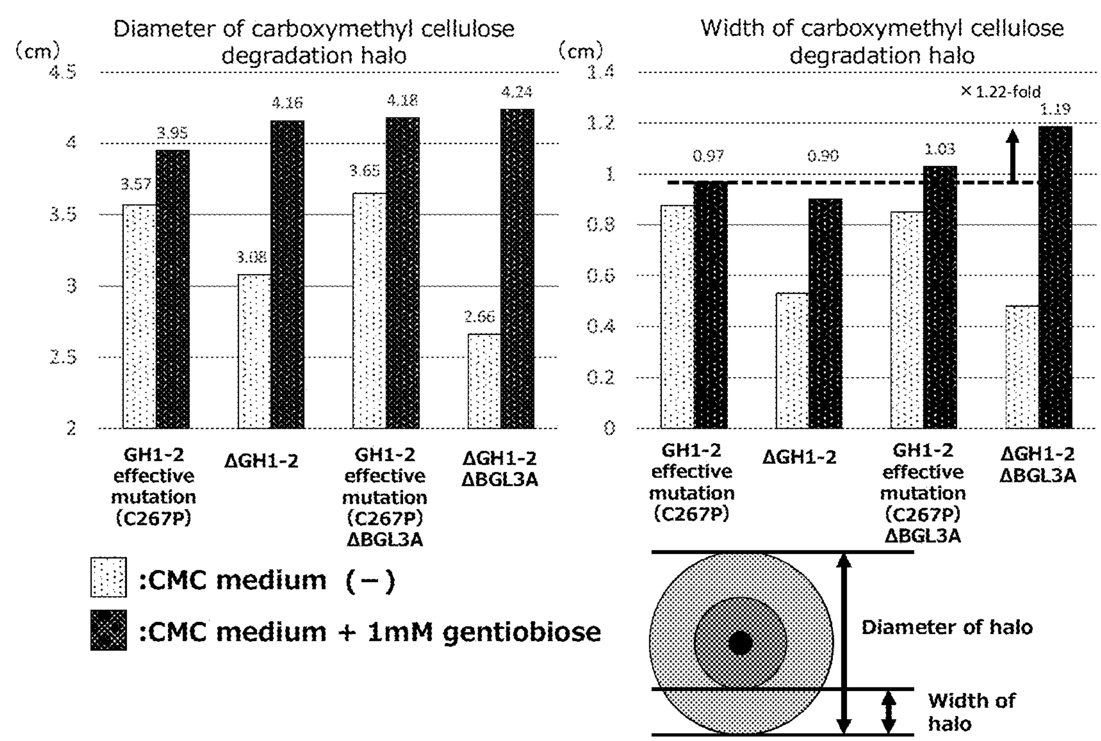

[Fig. 25]
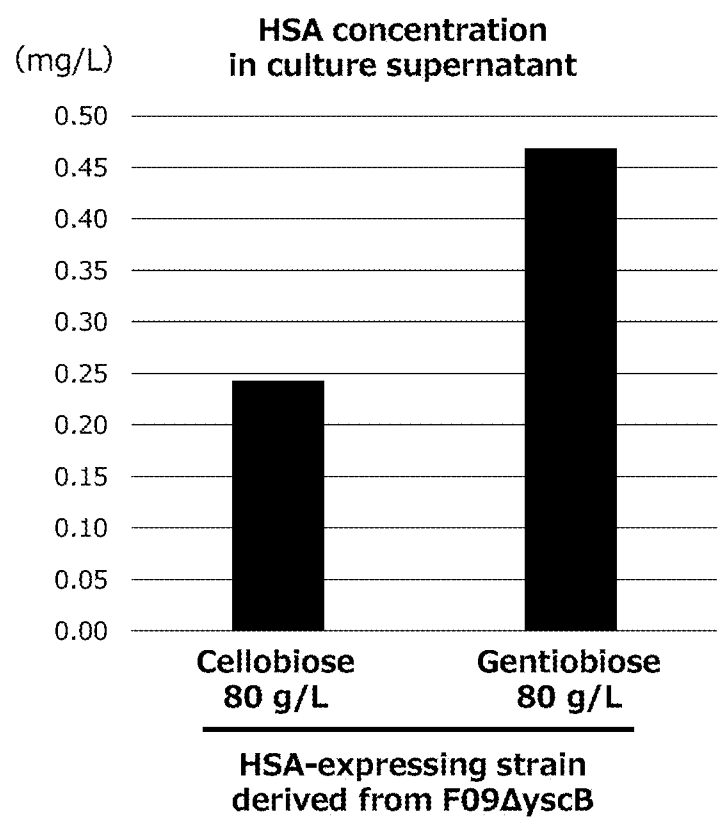

METHOD FOR PRODUCING A PROTEIN AND DISACCHARIDE USING A *TALAROMYCES CELLULOLYTICUS*

This application is a continuation of, and claims priority under 35 U.S.C. § 120 to, International Application No. PCT/JP2018/035530, filed Sep. 25, 2018, and claims priority therethrough under 35 U.S.C. § 119 to Japanese Patent Application No. 2017-184180, filed Sep. 25, 2017, the entireties of which are incorporated by reference herein. Also, the Sequence Listing filed electronically herewith is hereby incorporated by reference (File name: 2020-03-23T_US-607_Seq_List; File size: 53 KB; Date recorded: Mar. 23, 2020).

BACKGROUND

Technical Field

The present invention relates to a method for producing a protein such as cellulase and a method for producing a disaccharide.

Background Art

Traditionally, glucose, fructose, sucrose, blackstrap molasses, starch hydrolysates, and so forth are used as carbon sources in industrial production of objective substances such as L-amino acids by fermentation. However, due to a recent increase in population and improvement in living standards in developing countries, practical use of non-edible biomass raw materials derived from plants instead of those edible materials derived from plants have been investigated.

Such non-edible biomass raw materials derived from plants are composed of cellulose, hemicellulose, lignin, etc. Among them, cellulose and hemicellulose can be converted into pentose and hexose via a pretreatment step using heat, acid, or the like, a saccharification treatment step using a saccharification enzyme such as cellulase and hemicellulase, and so forth, and then used as raw materials for fermentation (Japanese Patent Laid-open (Translation of PCT Application) No. H9-507386 and Japanese Patent Laid-open (Translation of PCT Application) No. H11-506934).

As the saccharification enzyme, enzyme preparations derived from various cellulase-producing microorganisms have been used. As the cellulase-producing microorganisms, fungi such as *Trichoderma reesei* and *Talaromyces cellulolyticus* (formerly, *Acremonium cellulolyticus*) and bacteria such as *Clostridium thermocellum* are known. Specifically, for example, it has been reported that *Talaromyces cellulolyticus* Cl strain (Japanese Patent Laid-open (Kokai) No. 2003-135052) and *Talaromyces cellulolyticus* CF-2612 strain (Japanese Patent Laid-open (Kokai) No. 2008-271927) have a high cellulase-producing ability.

Cellulase production by fungi is typically induced by disaccharides. For example, sophorose can be a strong inducer for cellulase production. In addition, cellulase production induced by gentiobiose has been reported (WO2004/035070; Japanese Patent Laid-open (Translation of PCT Application) No. 2015-518723; Kurasawa T, et. al., Induction of Cellulase by Gentiobiose and Its Sulfur-Containing Analog in *Penicillium purpurogenum*. Appl Environ Microbiol. 1992 January; 58(1):106-10; Stuart M. Pitson, et. al., Induction and carbon source control of extracellular β-glucosidase production in *Acremonium persicinum*. Mycol Res. 1999 February; 103(Pt 2):161-7; Collins C M, et. al., Molecular cloning and expression analysis of two distinct beta-glucosidase genes, bgl and avenl, with very different biological roles from the thermophilic, saprophytic fungus *Talaromyces emersonii*. Mycol Res. 2007 July; 111(Pt 7):840-9; D Sternberg and G R Mandels, Induction of cellulolytic enzymes in *Trichoderma reesei* by sophorose. J Bacteriol. 1979 September; 139(3):761-9; Nisizawa T, et. al., Inductive Formation of Cellulase by Sophorose in *Trichoderma viride*. J Biochem. 1971 70(3):375-85). It has been known, for *Talaromyces cellulolyticus*, that cellulase production is not induced by sophorose but is induced by lactose (Fang X, et. al., Lactose enhances cellulase production by the filamentous fungus *Acremonium cellulolyticus*. J Biosci Bioeng. 2008 August; 106(2):115-20). However, it has not been known whether cellulase production is induced by gentiobiose in *Talaromyces cellulolyticus*.

As methods for producing a disaccharide such as gentiobiose, methods of using an enzyme such as beta-glucosidase have been reported. For example, methods for producing a disaccharide from glucose using beta-glucosidase have been reported (Japanese Patent Laid-open (Kokai) No. 2010-227032) or an enzyme of fungi such as *Trichoderma reesei* (WO2004/035070). However, use of an enzyme of *Talaromyces cellulolyticus* for producing a disaccharide has not previously been reported.

SUMMARY

An aspect of the present invention is to provide a method for producing a protein such as cellulase and a method for producing a disaccharide.

As a result, it has been found that cellulase can be efficiently produced by secretory production by culturing *Talaromyces cellulolyticus* in the presence of gentiobiose, and induced expression of cellulase by an expression inducer such as gentiobiose in *Talaromyces cellulolyticus* can be enhanced by modification of a GH1-2 gene, and a disaccharide such as gentiobiose can be produced from a saccharide raw material such as glucose by using an enzyme of *Talaromyces cellulolyticus*.

It is an aspect of the present invention to provide a method for producing an objective protein, comprising culturing *Talaromyces cellulolyticus* that has an ability to produce an objective protein in a culture medium comprising an expression inducer, wherein the expression inducer is gentiobiose.

It is a further aspect of the present invention to provide the method as described above, wherein the *Talaromyces cellulolyticus* has a feature selected from the group consisting of: (A) the *Talaromyces cellulolyticus* has been modified so that the activity of a GH1-2 protein is reduced as compared with a non-modified *Talaromyces cellulolyticus*; (B) the *Talaromyces cellulolyticus* has been modified so that a gh1-2 gene has a mutation that improves ability to produce the objective protein; and (C) combinations thereof.

It is a further aspect of the present invention to provide the method as described above, comprising culturing *Talaromyces cellulolyticus* that has an ability to produce an objective protein in a culture medium comprising an expression inducer, wherein the *Talaromyces cellulolyticus* has a feature selected from the group consisting of: (A) the *Talaromyces cellulolyticus* has been modified so that the activity of a GH1-2 protein is reduced as compared with a non-modified *Talaromyces cellulolyticus*; (B) the *Talaromyces cellulolyticus* has been modified so that a gh1-2 gene has a mutation that improves the ability to produce the objective protein; (C) combinations thereof, and wherein the expression inducer is a saccharide comprising glucose as a constituent sugar, provided that the expression inducer is gentiobiose when the activity of the GH1-2 protein is completely eliminated.

It is a further aspect of the present invention to provide the method as described above, wherein the expression inducer is gentiobiose, cellobiose, or cellulose.

It is a further aspect of the present invention to provide the method as described above, wherein the expression inducer is gentiobiose.

It is a further aspect of the present invention to provide the method as described above, wherein the activity of the GH1-2 protein is reduced by a means selected from the group consisting of: (A1) reducing the expression of a gh1-2 gene; (A2) disrupting a gh1-2 gene; (A3) modifying a gh1-2 gene so as to have a mutation that improves the objective protein-producing ability of the *Talaromyces cellulolyticus*; and (A4) combinations thereof.

It is a further aspect of the present invention to provide the method as described above, wherein the activity of the GH1-2 protein is reduced by deletion of a gh1-2 gene.

It is a further aspect of the present invention to provide the method as described above, wherein the mutation is a mutation selected from the group consisting of: (A) replacing an amino acid residue corresponding to the cysteine residue at position 267 in SEQ ID NO: 23 with another amino acid residue; (B) replacing an amino acid residue corresponding to the tryptophan residue at position 363 in SEQ ID NO: 23 with another amino acid residue; (C) replacing an amino acid residue corresponding to the tryptophan residue at position 449 in SEQ ID NO: 23 with another amino acid residue; and (D) combinations thereof.

It is a further aspect of the present invention to provide the method as described above, wherein said another amino acid in the (A) mutation is a proline residue; said another amino acid in the (B) mutation is a phenylalanine residue; said another amino acid in the (C) mutation is a phenylalanine residue.

It is a further aspect of the present invention to provide the method as described above, wherein the GH1-2 protein is selected from the group consisting of: (a) a protein comprising the amino acid sequence of SEQ ID NO: 23; (b) a protein comprising the amino acid sequence of SEQ ID NO: 23, but which includes substitution, deletion, insertion, and/or addition of 1 to 10 amino acid residues, and wherein said protein has a disaccharide hydrolysis activity; (c) a protein comprising an amino acid sequence having an identity of 90% or higher to the amino acid sequence of SEQ ID NO: 23, and wherein said protein has a disaccharide hydrolysis activity.

It is a further aspect of the present invention to provide the method as described above, wherein the *Talaromyces cellulolyticus* has a feature selected from the group consisting of: (A) the *Talaromyces cellulolyticus* has been modified so that the activity of a beta-glucosidase other than a GH1-2 protein is reduced as compared with a non-modified strain; (B) the *Talaromyces cellulolyticus* has been modified so that the activity of a CreA protein is reduced as compared with a non-modified *Talaromyces cellulolyticus*; (C) the *Talaromyces cellulolyticus* has been modified so that the activity of a YscB protein is reduced as compared with a non-modified *Talaromyces* celluloyticus; (D) combinations thereof.

It is a further aspect of the present invention to provide the method as described above, wherein the beta-glucosidase is a BGL3A protein.

It is a further aspect of the present invention to provide the method as described above, wherein the *Talaromyces cellulolyticus* is a modified strain derived from *Talaromyces cellulolyticus* strain S6-25 (NITE BP-01685) or Y-94 (FERM BP-5826).

It is a further aspect of the present invention to provide the method as described above, wherein the objective protein is accumulated in the culture medium by the culturing.

It is a further aspect of the present invention to provide the method as described above, wherein the objective protein is expressed under control of a promoter that functions in *Talaromyces cellulolyticus* and is inducible by the expression inducer.

It is a further aspect of the present invention to provide the method as described above, wherein the promoter is a cbhI promoter or a cbhII promoter.

It is a further aspect of the present invention to provide the method as described above, wherein the objective protein is expressed as a fused protein with a signal peptide that functions in *Talaromyces cellulolyticus*.

It is a further aspect of the present invention to provide the method as described above, wherein the objective protein is cellulase.

It is a further aspect of the present invention to provide the method as described above, further comprising producing the gentiobiose by an enzymatic conversion from a saccharide raw material using a disaccharide synthesizing enzyme.

It is a further aspect of the present invention to provide the method as described above, wherein the enzymatic conversion is carried out by bringing *Escherichia coli* cells containing the disaccharide synthesizing enzyme into contact with the saccharide raw material.

It is a further aspect of the present invention to provide the method as described above, wherein the saccharide raw material is selected from the group consisting of glucose, cellobiose, cellulose, and combinations thereof.

It is a further aspect of the present invention to provide a method for producing a disaccharide, comprising bringing *Escherichia coli* cells containing a disaccharide synthesizing enzyme into contact with a saccharide raw material to thereby generate the disaccharide.

It is a further aspect of the present invention to provide the method as described above, wherein the disaccharide synthesizing enzyme is beta-glucosidase.

It is a further aspect of the present invention to provide the method as described above, wherein the beta-glucosidase is a GH1-2 protein or a BGL3A protein.

It is a further aspect of the present invention to provide the method as described above, wherein the disaccharide synthesizing enzyme is a protein selected from the group consisting of: (a) a protein comprising the amino acid sequence of SEQ ID NO: 23 or 38; (b) a protein comprising the amino acid sequence of SEQ ID NO: 23 or 38, but which includes substitution, deletion, insertion, and/or addition of 1 to 10 amino acid residues, and wherein said protein has an activity of synthesizing a disaccharide synthesizing from a saccharide raw material; and (c) a protein comprising an amino acid sequence having an identity of 90% or higher to the amino acid sequence of SEQ ID NO: 23 or 38, and wherein said protein has an activity of synthesizing a disaccharide synthesizing from a saccharide raw material.

It is a further aspect of the present invention to provide the method as described above, wherein the disaccharide is selected from the group consisting of gentiobiose, cellobiose, laminaribiose, sophorose, and combinations thereof.

It is a further aspect of the present invention to provide the method as described above, wherein the disaccharide comprises gentiobiose.

It is a further aspect of the present invention to provide the method as described above, wherein the saccharide raw material is selected from the group consisting of glucose, cellobiose, cellulose, and combinations thereof.

It is a further aspect of the present invention to provide the method as described above, wherein the saccharide raw material comprises glucose.

BRIEF DESCRIPTION OF DRAWINGS

FIG. 1 shows a diagram (photograph) showing a result of cellulase production by T *cellulolyticus* strains F09pyr+ and F09Δgh1-2 using a cellulosic substrate (Solka-Floc) as a carbon source.

FIG. 2 shows a diagram (photograph) showing a result of cellulase halo assay by T *cellulolyticus* strains F09pyr+ and F09Δgh1-2 using a cellulosic substrate (CMC) as a carbon source.

FIG. 3 shows a diagram (photograph) showing a result of heterologous expression of GH1-2 of *T. cellulolyticus* in *E. coli*.

FIG. 4 shows a diagram showing a result of production of beta-linked glucose oligo saccharides from glucose by GH1-2 of *T. cellulolyticus*.

FIG. 5 shows a diagram (photograph) showing a result of induction of cellulase production by beta-linked glucose oligo saccharides in *T. cellulolyticus* strains F09pyr+ and F09Δgh1-2.

FIG. 6 shows a diagram (photograph) showing a result of production of beta-linked glucose oligo saccharides from cellobiose by GH1-2 of *T. cellulolyticus*.

FIG. 7 shows a diagram showing a result of production of beta-linked glucose oligo saccharides from cellobiose by GH1-2 of *T. cellulolyticus*.

FIG. 8 shows a diagram showing a result of production of gentiobiose from glucose by *E. coli* cells expressing GH1-2 of *T. cellulolyticus*.

FIG. 9 shows a diagram (photograph) showing a result of production of gentiobiose from glucose by *E. coli* cells expressing GH1-2 of *T. cellulolyticus*.

FIG. 10 shows a diagram showing a result of induction of cellulase production by gentiobiose in *T. cellulolyticus* strain F09ΔcreA.

FIG. 11 shows a diagram showing a result of induction of cellulase production by gentiobiose in *T. cellulolyticus* strains F09ΔcreA and F09Δgh1-2ΔcreA.

FIG. 12 shows a diagram showing a result of induction of cellulase production by gentiobiose in *T. cellulolyticus* strain F09ΔcreA.

FIG. 13 shows a diagram showing a result of production of gentiobiose from a cellulosic substrate by a culture supernatant containing BGL3A of *T. cellulolyticus*.

FIG. 14 shows a diagram showing a result of production of gentiobiose from cellobiose by a culture supernatant containing BGL3A of *T. cellulolyticus*.

FIG. 15 shows a diagram showing relative values of hydrolysis activity of the wild-type GH1-2 and mutant GH1-2s (W363F and W449F) of *T. cellulolyticus*.

FIG. 16 shows a diagram (photograph) showing change over time of reaction products upon allowing the wild-type GH1-2 and mutant GH1-2s (W363F and W449F) of *T. cellulolyticus* to act on cellobiose.

FIG. 17 shows a diagram showing change over time of reaction products upon allowing the wild-type GH1-2 of *T. cellulolyticus* to act on cellobiose.

FIG. 18 shows a diagram showing change over time of reaction products upon allowing the wild-type GH1-2 and a mutant GH1-2 (W363F) of *T. cellulolyticus* to act on cellobiose.

FIG. 19 shows a diagram showing a bleeding history of *T. cellulolyticus* strains.

FIG. 20 shows a diagram showing a result of cellulase production by *T. cellulolyticus* strains Y-94, C267Prep, and TN using a cellulosic substrate (Solka-Floc) as a carbon source.

FIG. 21 shows a diagram (photograph) showing a result of cellulase halo assay by T *cellulolyticus* strains Y-94, C267Prep, and TN using a cellulosic substrate (CMC) as a carbon source.

FIG. 22 shows a diagram showing a result of cellulase production by *T. cellulolyticus* strains Y-94, C267Prep, W363Frep, and W449Frep using a cellulosic substrate (Solka-Floc) as a carbon source.

FIG. 23 shows a diagram (photograph) showing a result of induction of cellulase production by gentiobiose in *T. cellulolyticus* strains Y-94, W363Frep, W449Frep, and C267Prep.

FIG. 24 shows a diagram showing a result of induction of cellulase production by gentiobiose in *T. cellulolyticus* strains F09pyrF+, F09Δgh1-2, F09Δbgl3A, and F09Δgh1-2Δbgl3A.

FIG. 25 shows a diagram showing a result of induction of HSA production by gentiobiose in *T. cellulolyticus* strain F09ΔyscB.

DETAILED DESCRIPTION

<1> Method for Producing Objective Protein

The method for producing an objective protein is a method using an expression inducer, such as gentiobiose, and *Talaromyces cellulolyticus. Talaromyces cellulolyticus* used in this method is also referred to as "the microorganism of the present invention".

<1-1> Expression Inducer

The expression inducer is not particularly limited so long as it is able to induce the expression of the objective protein in the microorganism. Examples of the expression inducer include saccharides having a length of two residues or longer and containing glucose as a constituent sugar. The expression inducer may typically contain only glucose as a constituent sugar. Specific examples of the expression inducer include disaccharides of glucose, that is, disaccharides constituted by two molecules of glucose, cello-oligosaccharides, and cellulose. Examples of the disaccharides include beta-linked disaccharides. Specific examples of the beta-linked disaccharides include gentiobiose, cellobiose, laminaribiose, and sophorose. Examples of the cello-oligosaccharides include, for example, cellobiose, cellotriose, and cellotetraose. Examples of cellulose include, for example, cellulosic substrates that can be used as carbon sources. Specific examples of the cellulosic substrates include, for example, microcrystalline cellulose (Avicel), filter paper, waste paper, pulp, wood, rice straw, wheat straw, rice husk, rice bran, wheat bran, sugarcane bagasse, coffee grounds, and tea lees. The cellulosic substrate may also be used after being subjected to a pretreatment such as hydrothermal decomposition treatment, acid treatment, alkaline treatment, steaming, blasting, and grinding. Examples of commercially-available cellulosic substrates include Solka-floc (International Fiber Corp, North Tonawanda, N.Y., U.S.A). Particular examples of the expression inducer include gentiobiose, cellobiose, and cellulose. More particular examples of the expression inducer include gentiobiose. As the expression inducer, one kind of substance may be used, or two or more kinds of substances may be used in combination. The expression inducer can be appropriately selected according to various conditions such as the type of promoter used for expression and the type of modification possessed by the microorganism. In any case, as the expression inducer, for example, gentiobiose may be selected. When the microorganism is a modified strain, as the expression inducer, for example, an expression inducer may be selected so that a combination of modification possessed by the microorganism and use of the expression inducer provides an increase in production of the objective protein.

For example, the expression inducer itself may induce the expression of the objective protein, or the expression inducer may be converted to another substance and then may induce the expression of the objective protein. Specifically, for example, the expression inducer may be converted to another substance by an action of a GH1-2 protein or an action of a combination of a GH1-2 protein and another enzyme and then may induce the expression of the objective protein. Examples of the other enzyme include cellulase. Examples of the other substance include disaccharides such as gentiobiose and cellobiose. Particular examples of the other substance include gentiobiose. That is, specifically, for example, an expression inducer other than gentiobiose may be converted to gentiobiose by an action of a GH1-2 protein or an action of a combination of a GH1-2 protein and another enzyme and then may induce the expression of the objective protein.

<1-2> Microorganism

The microorganism can be *Talaromyces cellulolyticus* having an objective protein-producing ability. In the descriptions concerning the microorganism, the microorganism or *Talaromyces cellulolyticus* to be used for constructing the same can also be referred to as a “host”.

<1-2-1>*Talaromyces cellulolyticus*

The microorganism can be *Talaromyces cellulolyticus*. A former name of *Talaromyces cellulolyticus* is *Acremonium cellulolyticus*. That is, *Acremonium cellulolyticus* was reclassified to *Talaromyces cellulolyticus* due to revision of phylogenetic taxonomy (FEMS Microbiol. Lett., 2014, 351: 32-41). Specific examples of *Talaromyces cellulolyticus* include strains C1 (Japanese Patent Laid-open (Kokai) No. 2003-135052), CF-2612 (Japanese Patent Laid-open (Kokai) No. 2008-271927), TN (FERM BP-685), S6-25 (NITE BP-01685), Y-94 (FERM BP-5826), and derivative strains thereof. The phrase “*Talaromyces cellulolyticus*” collectively refers to fungi classified at any time as *Talaromyces cellulolyticus* That is, a fungus once classified to *Talaromyces cellulolyticus* should be regarded as *Talaromyces cellulolyticus* even if phylogenetic taxonomy thereof is changed in future.

The strain S6-25 was originally deposited at the independent administrative agency, National Institute of Technology and Evaluation, Patent Microorganisms Depositary (#122, 2-5-8 Kazusakamatari, Kisarazu-shi, Chiba-ken, 292-0818, Japan) on Aug. 8, 2013, and then converted to an international deposit under the provisions of the Budapest Treaty on Nov. 15, 2013, and assigned an accession number of NITE BP-01685. This strain was obtained from the strain TN (FERM BP-685) and has a high cellulase-producing ability. The strain Y-94 was originally deposited at the National Institute of Bioscience and Human Technology, Agency of Industrial Science and Technology, Ministry of International Trade and Industry (currently, independent administrative agency, National Institute of Technology and Evaluation, International Patent Organism Depositary, #120, 2-5-8 Kazusakamatari, Kisarazu-shi, Chiba-ken, 292-0818, Japan) on Jan. 12, 1983, and then converted to an international deposit under the provisions of the Budapest Treaty on Feb. 19, 1997, and assigned an accession number of FERM BP-5826.

These strains can be obtained from, for example, the depositories at which the strains were deposited.

*Talaromyces cellulolyticus* such as the strains exemplified above can be used as is, or after being modified as required. That is, the microorganism may be any of the strains exemplified above, or may be a modified strain derived from any of the strains exemplified above. The microorganism may specifically be, for example, a modified strain derived from the strain S6-25 or Y-94.

<1-2-2> Ability to Produce an Objective Protein

The microorganism has an ability to produce an objective protein. The phrase “a microorganism having an ability to produce an objective protein-” refers to a microorganism having an ability to produce an objective protein in the presence of an expression inducer. The phrase “a microorganism having an ability to produce an objective protein” may specifically refer to a microorganism having an ability to express an objective protein and accumulate an objective protein in a culture broth to such a degree that the objective protein can be collected therefrom, when the microorganism is cultured in a culture medium including an expression inducer. The phrase “accumulation in a culture broth” may specifically refer to, for example, accumulation in a culture medium, on a cell surface layer, in microbial cells, or in/on a combination thereof. A case where the objective protein is accumulated outside microbial cells, for example, in a culture medium or on a cell surface layer, can also be referred to as “secretion” or “secretory production” of the objective protein. That is, the microorganism may have a secretory production ability of the objective protein, that is, an ability to produce the objective protein by secretory production. The objective protein may be accumulated particularly in a culture medium. The accumulation amount of the objective protein may be, for example, 10 μg/L or more, 1 mg/L or more, 100 mg/L or more, or 1 g/L or more, in terms of the accumulation amount in a culture broth. The microorganism may have an ability to produce a single kind of objective protein, or two or more kinds of objective proteins.

The microorganism may inherently have the ability to produce an objective protein, or may be a microorganism modified so as to have an ability to produce an objective protein. The microorganism can typically inherently have an ability to produce cellulase, that is, an ability to produce cellulase in the presence of an expression inducer. The microorganism may also be modified so that an ability to produce an objective protein inherently possessed by the microorganism has been enhanced. The microorganism having an ability to produce an objective protein can be obtained by, for example, imparting an ability to produce an objective protein to such *Talaromyces cellulolyticus* as mentioned above, or enhancing an ability to produce an objective protein of such *Talaromyces cellulolyticus* as mentioned above. The ability to produce an objective protein can be imparted or enhanced by, for example, introduction of a genetic construct for expression of the objective protein, introduction of another modification for improving the ability to produce an objective protein, or both.

The microorganism has an ability to produce an objective protein at least on the basis of possession of a genetic construct for expression of the objective protein. The microorganism may have an ability to produce an objective protein specifically on the basis of possession of a genetic construct for expression of the objective protein or on the basis of a combination of possession of a genetic construct for expression of the objective protein and another characteristic. That is, the microorganism has a genetic construct for expression of the objective protein. The microorganism may have one copy or two or more copies of the genetic construct for expression of the objective protein. The microorganism may have a single kind of genetic construct for expression of the objective protein, or may have two or more kinds of genetic constructs for expression of the objective protein. The copy number and the number of kinds of the genetic construct for expression of the objective protein may be read as, respectively, the copy number and the number of kinds of the objective protein.

In the microorganism, the genetic construct for expression of the objective protein may be present on a vector autonomously replicable out of the chromosome such as a plasmid, or may have been introduced into the chromosome. That is, the microorganism may have the genetic construct for expression of the objective protein on a vector, and in other words, may have a vector containing the genetic construct for expression of the objective protein. Also, the microorganism may have the genetic construct for expression of the objective protein on the chromosome. When the microorganism has two or more genetic constructs for expression of the objective protein, it is sufficient that those genetic constructs are possessed by the microorganism so that the objective protein can be produced. For example, all of those genetic constructs may be carried by a single expression vector, or may be carried by the chromosome. Alternatively, those genetic constructs may be separately carried by a plurality of expression vectors, or may be separately carried by a single or a plurality of expression vectors and the chromosome.

The microorganism may inherently having a genetic construct for expression of the objective protein, or may be modified so as to have a genetic construct for expression of the objective protein. The microorganism can typically inherently have a genetic construct for expression of cellulase. The microorganism may also be a microorganism introduced with a genetic construct for expression of the objective protein, in addition to or instead of a genetic construct for expression of the objective protein inherently possessed by the microorganism. The microorganism having a genetic construct for expression of the objective protein can be obtained by introducing the genetic construct for expression of the objective protein into such *Talaromyces cellulolyticus* as mentioned above.

The phrase "a genetic construct for expression of an objective protein" refers to a gene expression system configured to be able to express an objective protein in the presence of an expression inducer. The genetic construct for expression of the objective protein can also be referred to as an "expression system for an objective protein" or an "expression unit for an objective protein". The genetic construct for expression of the objective protein includes, in the direction from 5' to 3', a promoter sequence inducible by an expression inducer and a nucleotide sequence encoding the objective protein. A promoter sequence can also be referred to simply as a "promoter". A nucleotide sequence encoding an amino acid sequence can also be referred to as a "gene". For example, A nucleotide sequence encoding the objective protein can also be referred to as a "gene encoding an objective protein" or an "objective protein gene". It is sufficient that the objective protein gene is ligated downstream from the promoter so that the objective protein is expressed under the control of the promoter. The genetic construct for expression of the objective protein may also include a regulatory sequence effective for expression of the objective protein, such as an operator and a terminator, at an appropriate position so that it can function. The phrases "expression of an objective protein gene", "expression of an objective protein", "generation of an objective protein", and "production of an objective protein" can be used synonymously, unless otherwise stated. The genetic construct for expression of the objective protein can be appropriately designed according to various conditions such as the type of objective protein.

The promoter is not particularly limited so long as it functions in *Talaromyces cellulolyticus* and is inducible by an expression inducer. The promoter may be inducible by a single kind of expression inducer, or may be inducible by two or more kinds of expression inducers. As the promoter, a promoter inducible at least by the chosen expression inducer can be used. The phrase "a promoter that functions in *Talaromyces cellulolyticus*" refers to a promoter having a promoter activity, i.e. a gene transcription activity, in *Talaromyces cellulolyticus*. The phrase "a promoter inducible by an expression inducer" refers to a promoter inducibly expressing a gene ligated immediately downstream of the promoter in the presence of an expression inducer. The phrase "in the presence of an expression inducer" may specifically refer to conditions where an expression inducer is present in a culture medium. The phrase "a gene is inducibly expressed in the presence of an expression inducer" means that the expression amount of a gene in the presence of an expression inducer is higher than the expression amount of the gene in the absence of the expression inducer. The phrase "a gene is inducibly expressed in the presence of an expression inducer" may specifically mean that the expression amount of a gene in the presence of an expression inducer is 2 times or more, 3 times or more, or 4 times or more of the expression amount of the gene in the absence of the expression inducer. The phrase "a gene is inducibly expressed in the presence of an expression inducer" also includes when a gene is expressed in the presence of an expression inducer whereas the gene is not expressed in the absence of the expression inducer. Gene expression from the promoter may be directly induced by the expression inducer, or may be indirectly induced by another substance generated from the expression inducer.

The promoter may be derived from the host, or may be a heterologous promoter. The promoter may be the native promoter of the objective protein gene, or may be a promoter of another gene. Examples of the promoter include promoters of cellulase genes of microorganisms of which cellulase production is induced by an expression inducer. Specific examples of the promoter include promoters of cellulase genes of *Talaromyces cellulolyticus*. Examples of the cellulase genes include a cbhI gene (also referred to as cbh1 gene) and a cbhII gene (also referred to as cbh2 gene). That is, examples of the promoter include a promoter of the cbhI gene and a promoter of the cbhII gene. The promoter of the cbh1 gene is also referred to as a "cbhI promoter" or a "cbh1 promoter". The promoter of the cbhII gene is also referred to as a "cbhII promoter" or a "cbh2 promoter". These promoters each may function as, for example, a promoter inducible by one or more kinds of substances selected from the expression inducers exemplified above. These promoters each may function as, specifically, a promoter inducible at least by gentiobiose, cellobiose, and/or cellulose. These promoters each may function as, more specifically, a promoter inducible at least by gentiobiose, i.e. gentiobiose-inducible promoter. The nucleotide sequences of the cbhI and cbhII promoters of *Talaromyces cellulolyticus* are shown in SEQ ID NOS: 49 and 50, respectively. That is, the promoter may be, for example, a promoter having any of the nucleotide sequences of the promoters exemplified above, e.g. the nucleotide sequence of SEQ ID NO: 49 or 50. The promoter may also be, for example, a conservative variant of any of the promoters exemplified above, e.g. a conservative variant of the promoter having the nucleotide sequence of SEQ ID NO: 49 or 50. That is, for example, each of the promoters exemplified above can be used as it is, or after being modified as required. The phrases "cbhI promoter" and "cbhII promoter" include not only the cbhI and cbhII promoters exemplified above, but also include conservative variants thereof. The descriptions concerning conservative variants of the gh1-2 gene below can be similarly applied to conservative variants of the promoter. For example, the promoter may be a DNA having a nucleotide sequence having a homology of 80% or higher, 90% or higher, 95% or higher, 97% or higher, or 99% or higher, to the nucleotide sequence of SEQ ID NO: 49 or 50, so long as the original function is maintained. The term "original function" used for the promoter inducible by an expression inducer refers to a function of inducibly expressing a gene ligated immediately downstream of the promoter in the presence of the expression inducer. The function of the promoter inducible by an expression inducer can be confirmed by, for example, confirming an induced expression of a gene by supplying the expression inducer to a culture medium. The induced expression of a gene can be confirmed by, for example, using a reporter gene.

The objective protein is not particularly limited. The objective protein may be derived from the host, or may be a heterologous protein. The phrase "heterologous protein" refers to an exogenous protein relative to *Talaromyces cellulolyticus* that produces the protein. The objective protein may be, for example, a protein derived from a microorganism, a protein derived from a plant, a protein derived from an animal, a protein derived from a virus, or a protein of which the amino acid sequence is artificially designed. The objective protein may particularly be a derived from human. The objective protein may be a monomeric protein or a multimeric protein. The term "multimeric protein" refers to a protein having two or more subunits. In the multimer, the subunits may be linked by covalent bonds such as disulfide bonds, linked by non-covalent bonds such as hydrogen bonds and hydrophobic interaction, or linked by a combination thereof. The multimer can include one or more intermolecular disulfide bonds. The multimer may be a homo-multimer having a single kind of subunit, or may be a hetero-multimer having two or more kinds of subunits. The phrase "an objective protein is a heterologous protein" may mean that, in cases where the objective protein is a hetero-multimer, at least one subunit is a heterologous protein. That is, all the subunits may be heterologous, or only some of the subunits may be heterologous. The objective protein may be a secretory protein or a non-secretory protein. Although the objective protein may be a secretory protein in nature, or may be a non-secretory protein in nature, it is preferred that the objective protein is a secretory protein in nature. The phrase "protein" also includes substances called "peptide", such as oligopeptides and polypeptides.

Examples of the objective protein include, for example, enzymes, physiologically active proteins, receptor proteins, antigenic proteins to be used as vaccines, and any other proteins.

Examples of the enzymes include, for example, cellulase, transglutaminase, protein glutaminase, isomaltodextranase, protease, endopeptidase, exopeptidase, aminopeptidase, carboxypeptidase, collagenase, chitinase, and so forth.

The phrase "cellulase" collectively refers to enzymes catalyzing a reaction of hydrolyzing a glycoside bond contained in cellulose. Examples of cellulase include endo-type cellulase (endoglucanase; EC 3.2.1.4), exo-type cellulase (cellobiohydrolase; EC 3.2.1.91), and cellobiase (beta-glucosidase; EC 3.2.1.21). Cellulase is also referred to as Avicelase, filter paper cellulase (FPase), carboxymethylcellulase (CMCase), or the like depending on the substrate used for activity measurement. Examples of cellulase include, for example, cellulases of fungi such as *Trichoderma reesei* and *Talaromyces cellulolyticus* and cellulases of bacteria such as *Clostridium thermocellum*.

Examples of transglutaminase include, for example, secretory-type transglutaminases of Actinomycetes such as *Streptoverticillium mobaraense* IFO 13819 (WO01/23591), *Streptoverticillium cinnamoneum* IFO 12852, *Streptoverticillium griseocarneum* IFO 12776, and *Streptomyces lydicus* (WO96/06931), and of filamentous fungi such as Oomycetes (WO96/22366). Examples of protein glutaminase include, for example, protein glutaminase of *Chryseobacterium proteolyticum* (WO2005/103278). Examples of isomaltodextranase include, for example, isomaltodextranase of *Arthrobacter globiformis* (WO2005/103278).

Examples of the physiologically active proteins include, for example, growth factors, hormones, cytokines, and antibody-related molecules.

Specific examples of the growth factors include, for example, epidermal growth factor (EGF), insulin-like growth factor-1 (IGF-1), transforming growth factor (TGF), nerve growth factor (NGF), brain-derived neurotrophic factor (BDNF), vesicular endothelial growth factor (VEGF), granulocyte-colony stimulating factor (G-CSF), granulocyte-macrophage-colony stimulating factor (GM-CSF), platelet-derived growth factor (PDGF), erythropoietin (EPO), thrombopoietin (TPO), acidic fibroblast growth factor (aFGF or FGF1), basic fibroblast growth factor (bFGF or FGF2), keratinocyte growth factor (KGF-1 or FGF7, and, KGF-2 or FGF10), and hepatocyte growth factor (HGF).

Specific examples of the hormones include, for example, insulin, glucagon, somatostatin, human growth hormone (hGH), parathyroid hormone (PTH), calcitonin, and exenatide.

Specific examples of the cytokines include, for example, interleukins, interferons, and tumor necrosis factors (TNFs).

The growth factors, hormones, and cytokines may not be strictly distinguished from one another. For example, a physiologically active protein may be a growth factor, hormone, and/or cytokine.

Furthermore, a physiologically active protein may be an intact protein, or may be a part of a protein. Examples of a part of a protein include, for example, a part having physiological activity. Specific examples of a part having physiological activity include, for example, Teriparatide, a physiologically active peptide consisting of the N-terminal 34 amino acid residues of parathyroid hormone (PTH).

The phrase "antibody-related molecule" refers to a protein containing a molecular species having a single domain or a combination of two or more domains such as the domains constituting a complete antibody. Examples of the domains constituting a complete antibody include heavy chain domains VH, CH1, CH2, and CH3, and light chain domains VL and CL. The antibody-related molecule may be a monomeric protein, or may be a multimeric protein, so long as it contains the above-mentioned molecular species. When the antibody-related molecule is a multimeric protein, it may be a homo-multimer having a single kind of subunit, or may be a hetero-multimer having two or more kinds of subunits. Specific examples of the antibody-related molecules include, for example, complete antibody, Fab, F(ab'), F(ab')2, Fc, dimer having a heavy chain (H chain) and a light chain (L chain), Fc-fusion protein, heavy chain (H chain), light chain (L chain), light chain Fv (scFv), sc(Fv)$_2$, disulfide-bonded Fv (sdFv), diabody, and VHH fragment (Nanobody (registered trademark)). More specific examples of the antibody-related molecules include, for example, Trastuzumab and Nivolumab.

The receptor proteins are not particularly limited. A receptor protein may be, for example, a receptor protein for any physiologically active protein and other physiologically active substances. Examples of the other physiologically active substances include, for example, neurotransmitters such as dopamine. Furthermore, a receptor protein may be an orphan receptor of which the corresponding ligand is not known.

The antigen proteins to be used as vaccines are not particularly limited, so long as they are proteins that can induce an immune response. An antigen protein can be appropriately selected depending on the intended object of the immune response.

In addition, examples of other proteins include Liver-type fatty acid-binding protein (LFABP), fluorescent protein, immunoglobulin-binding protein, albumin, and extracellular protein. Examples of the fluorescent protein include Green Fluorescent Protein (GFP). Examples of the immunoglobulin-binding protein include Protein A, Protein G, and Protein L. Examples of albumin include human serum albumin.

Examples of the extracellular protein include fibronectin, vitronectin, collagen, osteopontin, laminin, and partial sequences thereof. Laminin is a protein having a heterotrimeric structure having an a chain, a (3 chain, and a γ chain. Examples of laminin include laminin of mammals. Examples of the mammals include primates such as human, monkey, and chimpanzee; rodents such as mouse, rat, hamster, and guinea pig; and other various mammals such as rabbit, horse, cattle, sheep, goat, pig, dog, and cat. Particular examples of the mammals include human. Examples of the subunit chains of laminin (i.e. α, β, and γ chains) include 5 kinds of α chains (α1 to α5), 3 kinds of β chains (β1 to β3), and 3 kinds of γ chains (γ1 to γ3). Laminin constitutes various isoforms depending on combinations of these subunits. Specific examples of laminin include, for example, laminin 111, laminin 121, laminin 211, laminin 213, laminin 221, laminin 311, laminin 321, laminin 332, laminin 411, laminin 421, laminin 423, laminin 511, laminin 521, and laminin 523. Examples of the partial sequence of laminin include laminin E8, which is an E8 fragment of laminin. Laminin E8 is a protein having a heterotrimeric structure consisting of an E8 fragment of a chain (a chain E8), an E8 fragment of β chain (β chain E8), and an E8 fragment of γ chain (γ chain E8). The subunit chains of laminin E8 (i.e. a chain E8, β chain E8, and γ chain E8) are also collectively referred to as "E8 subunit chains". Examples of the E8 subunit chains include E8 fragments of the laminin subunit chains exemplified above. Laminin E8 constitutes various isoforms depending on combinations of these E8 subunit chains. Specific examples of laminin E8 include, for example, laminin 111E8, laminin 121E8, laminin 211E8, laminin 221E8, laminin 332E8, laminin 421E8, laminin 411E8, laminin 511E8, and laminin 521E8.

The objective protein gene can be used as it is, or after being modified as required. The objective protein gene can be modified, for example, for obtaining a desired activity. The descriptions concerning conservative variants of the gh1-2 gene and the GH1-2 protein below can be similarly applied to variants of the objective protein gene and the objective protein. For example, the objective protein gene may be modified so that the amino acid sequence of the encoded objective protein includes substitution, deletion, insertion, and/or addition of one or several amino acid residues. A protein specified with the type of organism from which the protein is derived is not limited to proteins per se found in that organism, and shall also include proteins having any of the amino acid sequences of proteins found in that organism and variants thereof. That is, for example, the term "protein derived from human" is not limited to proteins per se found in human, and shall also include proteins having any of the amino acid sequences of proteins found in human and variants thereof. Furthermore, in the objective protein gene, any codon(s) may be replaced with respective equivalent codon(s) thereof. For example, the objective protein gene may be modified so that it has optimal codons according to codon frequencies in the chosen host.

The objective protein may have another amino acid sequence in addition to such an amino acid sequence of the objective protein as exemplified above. That is, the objective protein may be a fusion protein with another amino acid sequence. The "another amino acid sequence" is not particularly limited, so long as an objective protein having a desired characteristic can be obtained. The "another amino acid sequence" can be appropriately selected depending on various conditions such as its intended use or purpose. Examples of the "another amino acid sequence" include, for example, a signal peptide (also referred to as "signal sequence"), a peptide tag, and a recognition sequence of a protease. The "another amino acid sequence" may be bound to, for example, either one or both of the N-terminus and C-terminus of the objective protein. As the "another amino acid sequence", one kind of amino acid sequence may be used, or two or more kinds of amino acid sequences may be used in combination.

The signal peptide can be used for, for example, secretory production of the objective protein. The signal peptide may be bound to the N-terminus of the objective protein. That is, in an embodiment, the construct can include, in the direction from 5' to 3', a promoter sequence inducible by an expression inducer, a nucleotide sequence encoding the signal peptide, and a nucleotide sequence encoding the objective protein. In this case, it is sufficient that the nucleotide sequence encoding the objective protein is ligated downstream from the nucleotide sequence encoding the signal peptide so that the objective protein is expressed as a fusion protein with the signal peptide. In such a fusion protein, the signal peptide and the objective protein may be or may not be adjacent to each other. That is, the phrase "an objective protein is expressed as a fusion protein with a signal peptide" includes not only when an objective protein is expressed as a fusion protein with a signal peptide in which the signal peptide and the objective protein are adjacent to each other, but also includes when an objective protein is expressed as a fusion protein in which the signal peptide and the objective protein are fused with each other via another amino acid sequence. When producing an objective protein by secretory production using a signal peptide, typically, the signal peptide may be cleaved at the time of secretion, and the objective protein without the signal peptide may be secreted outside microbial cells. That is, the phrase "an objective protein is expressed as a fusion protein with a signal peptide" or the phrase "an objective protein includes a signal peptide" means that it is sufficient that the objective protein constitutes a fusion protein with a signal peptide at the time of expression, and it does not necessarily mean that the eventually-obtained objective protein constitutes a fusion protein with a signal peptide.

The signal peptide is not particularly limited so long as it functions in *Talaromyces cellulolyticus*. The phrase "a signal peptide that functions in *Talaromyces cellulolyticus*" refers to a signal peptide providing secretion of the objective protein when the signal peptide is ligated to the N-terminus of the objective protein.

The signal peptide may be a signal peptide derived from the host, or may be a heterologous signal peptide. The signal peptide may be the native signal peptide of the objective protein, or may be a signal peptide of another protein. Examples of the signal peptide include signal peptides of secretory cellulases of microorganisms. Specific examples of the signal peptide include signal peptides of secretory cellulases of *Talaromyces cellulolyticus*. Examples of the secretory cellulases include a CbhI protein encoded by a cbhI gene (also referred to as Cbh1 protein) and a CbhI protein encoded by a cbhII gene (also referred to as Cbh2 protein). That is, examples of the signal peptide include a signal peptide of the CbhI protein and a signal peptide of the CbhII protein. The signal peptide of the CbhI protein is also referred to as a "CbhI signal peptide" or a "Cbh1 signal peptide". The signal peptide of the CbhII protein is also referred to as a "CbhII signal peptide" or a "Cbh2 signal peptide". The amino acid sequence of the CbhI signal peptide of *Talaromyces cellulolyticus* is shown in SEQ ID NO: 51. That is, the signal peptide may be, for example, a signal peptide having any of the amino acid sequences of the signal peptides exemplified above, e.g. the amino acid sequence of SEQ ID NO: 51. The signal peptide may also be, for example, a conservative variant of any of the signal peptides exemplified above, e.g. a conservative variant of the signal peptide having the amino acid sequence of SEQ ID NO: 51. That is, for example, each of the signal peptides exemplified above can be used as it is, or after being modified as required. The phrases "CbhI signal peptide" and "CbhII signal peptide" include not only the CbhI and CbhII signal peptides exemplified above, but also include conservative variants thereof. The descriptions concerning conservative variants of the GH1-2 protein below can be similarly applied to conservative variants of the signal peptide. For example, the signal peptide may be a peptide having the amino acid sequence of SEQ ID NO: 51, but which includes substitution, deletion, insertion, and/or addition of one or several amino acid residues at one or several positions, so long as the original function is maintained. The term "one or several" mentioned above in the variant of the signal peptide is, specifically, for example, 1 to 7, 1 to 5, 1 to 3, or 1 to 2. For example, the signal peptide may also be a peptide having an amino acid sequence having a homology of 80% or higher, 90% or higher, 95% or higher, 97% or higher, or 99% or higher, to the amino acid sequence of SEQ ID NO: 51, so long as the original function is maintained. The term "original function" used for the signal peptide refers to a function of providing secretion of the objective protein when the signal peptide is ligated to the N-terminus of the objective protein. The function of the signal peptide can be confirmed by, for example, confirming secretion of a protein due to ligation of the signal peptide to the N-terminus of the protein.

Specific examples of the peptide tag include His tag, FLAG tag, GST tag, Myc tag, MBP (maltose binding protein), CBP (cellulose binding protein), TRX (thioredoxin), GFP (green fluorescent protein), HRP (horseradish peroxidase), ALP (alkaline phosphatase), and Fc region of antibody. The peptide tag can be utilized for, for example, detection and purification of the expressed objective protein.

Specific examples of the recognition sequence of a protease include the recognition sequence of the HRV3C protease, the recognition sequence of the Factor Xa protease, and the recognition sequence of the proTEV protease. The recognition sequence of a protease can be used for, for example, cleavage of the expressed objective protein. Specifically, for example, when the objective protein is expressed as a fusion protein with a peptide tag, if a recognition sequence of a protease is introduced into the connection part of the objective protein and the peptide tag, the peptide tag can be cleaved from the expressed objective protein by using a protease to obtain the objective protein not having the peptide tag.

The N-terminal region of the eventually-obtained objective protein may be the same as that of the natural protein, or may not be the same as that of the natural protein. For example, the N-terminal region of the eventually-obtained objective protein may be that of the natural protein including addition or deletion of one or several amino acid residues. Although the number of the "one or several" amino acid residues may differ depending on the full length or structure of the objective protein, specifically, it is 1 to 20, 1 to 10, 1 to 5, or 1 to 3.

Furthermore, the objective protein may also be expressed as a protein including a pro-structure moiety (proprotein). When the objective protein is expressed as a proprotein, the eventually-obtained objective protein may be or may not be the proprotein. That is, the proprotein may be processed into the mature protein by cleavage of the pro-structure moiety. The cleavage can be attained with, for example, a protease. When a protease is used, generally, the proprotein can be cleaved at a position substantially the same as that of the natural protein, or at exactly the same position as that of the natural protein so that the same mature protein as the natural mature protein is obtained, in view of the activity of the eventually-obtained protein. Therefore, generally, a specific protease that cleaves the proprotein at such a position that the same protein as the naturally occurring mature protein is generated is a particular example. However, the N-terminal region of the eventually-obtained objective protein may not be the same as that of the natural protein as described above. For example, depending on type, purpose of use etc. of the objective protein to be produced, a protein having an N-terminus longer or shorter by one to several amino acid residues compared with the natural protein may have more appropriate activity. Proteases usable in the method as described herein include, for example, commercially available proteases such as Dispase (produced by Boehringer Mannheim) as well as those obtainable from culture broth of a microorganism such as culture broth of actinomycetes. Such proteases may be used in an un-purified state, or may be used after purification to an appropriate purity as required.

The objective protein gene can be obtained by, for example, cloning. For cloning, for example, nucleotides, such as genomic DNA and cDNA, containing the objective protein gene can be used. Furthermore, the objective protein gene can also be obtained by, for example, total synthesis based on the nucleotide sequence thereof (Gene, 60(1), 115-127 (1987)). The obtained objective protein gene can be used as is, or after being modified as required. That is, a variant of an objective protein gene may be obtained by modifying the objective protein gene. A gene can be modified by a known technique. For example, an objective mutation can be introduced into an objective site of DNA by the site-specific mutation method. Examples of the site-specific mutation method include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a variant of an objective protein gene may be totally synthesized. Furthermore, the obtained objective protein gene can be subject to modification such as introduction of a promoter sequence as required, to thereby obtain the genetic construct for expression of the objective protein. Incidentally, other elements of the genetic construct for expression of the objective protein, such as a promoter sequence, and the genetic construct for expression of the objective protein can be obtained in a similar manner to that for obtaining the objective protein gene.

Genes can be modified by known methods. For example, an objective mutation can be introduced into a target site of DNA by the site-specific mutagenesis method. Examples of the site-specific mutagenesis method includes using PCR (Higuchi, R., 61, in PCR Technology, Erlich, H. A. Eds., Stockton Press (1989); Carter P., Meth. In Enzymol., 154, 382 (1987)), and a method of using a phage (Kramer, W. and Frits, H. J., Meth. in Enzymol., 154, 350 (1987); Kunkel, T. A. et al., Meth. in Enzymol., 154, 367 (1987)).

Methods for introducing the genetic construct for expression of the objective protein into *Talaromyces cellulolyticus* are not particularly limited. The phrase "introduction of a genetic construct for expression of an objective protein" refers to making a host harbor the genetic construct, and may specifically refer to introducing an objective protein gene into a host so that the objective protein can be expressed. The phrase "introduction of a genetic construct for expression of an objective protein" includes not only when the genetic construct for expression of the objective protein that has been preliminarily constructed is introduced into a host at at the same time, but also includes when a part of the genetic construct for expression of the objective protein is introduced into a host and the genetic construct for expression of the objective protein is constructed in the host, unless otherwise stated. For example, the promoter of an objective protein gene inherently possessed by a host may be replaced with a promoter inducible by an expression inducer to thereby construct the genetic construct for expression of the objective protein on the chromosome of the host. Also, for example, an objective protein gene may be introduced downstream of a promoter inducible by an expression inducer inherently possessed by a host to thereby construct the genetic construct for expression of the objective protein on the chromosome of the host.

The genetic construct for expression of the objective protein can be introduced into a host by using, for example, a vector containing the genetic construct for expression of the objective protein. A vector containing the genetic construct for expression of the objective protein is also referred to as an "expression vector of an objective protein". The vector containing the genetic construct for expression of the objective protein can be constructed by, for example, ligating the genetic construct for expression of the objective protein with a vector. Also, for example, when a vector contains a promoter inducible by an expression inducer, the vector containing the genetic construct for expression of the objective protein can also be constructed by ligating an objective protein gene downstream the promoter. By introducing an expression vector of the objective protein, a transformant transformed with the vector can be obtained, and that is, the genetic construct for expression of the objective protein can be introduced into the host. The vector is not particularly limited so long as it is autonomously replicable in cells of the host. The vector may be a single copy vector, a low copy vector, or a high copy vector. The vector may contain a marker gene for selection of transformants. The vector may contain a promoter inducible by an expression inducer and a terminator for expressing the introduced gene.

Furthermore, the genetic construct for expression of the objective protein may be introduced into the chromosome of a host. Introduction of a gene into the chromosome can be carried out by homologous recombination. Specifically, the genetic construct for expression of the objective protein can be introduced into the chromosome of a host by transforming the host with a recombinant DNA containing the genetic construct to thereby induce homologous recombination between the genetic construct and a target region of the chromosome of the host. The structure of the recombinant DNA to be used for homologous recombination is not particularly limited as long as it causes homologous recombination in a desired manner. For example, a host can be transformed with a linear DNA containing the genetic construct for expression of the objective protein and further containing upstream and downstream sequences of the substitution target region on the chromosome at the respective ends, so that homologous recombination occurs at each of the upstream and downstream sides of the target region, to thereby replace the target region with the genetic construct. The recombinant DNA to be used for homologous recombination may contain a marker gene for selection of transformants. Incidentally, introduction of a part of the genetic construct for expression of the objective protein, such as an objective protein gene and a promoter inducible by an expression inducer, into the chromosome can be carried out in a similar manner to that for introduction of the whole of the genetic construct for expression of the objective protein into the chromosome.

The marker gene can be appropriately selected according to the phenotype such as auxotrophy of the host. For example, when the host shows uracil auxotrophy due to mutation in a pyrF or pyrG gene, a strain introduced with a desired modification can be selected by using a pyrF or pyrG gene as a marker gene and using complementation of uracil auxotrophy, i.e. using uracil prototroph, as an indicator. Furthermore, as the marker gene, a drug resistance gene such as hygromycin resistance gene can be used.

Transformation can be carried out by, for example, a method generally used for transformation of eukaryotic microorganisms such fungi and yeasts. Examples of such a method include the protoplast method.

<1-2-3> Other Characteristics

The microorganism may have a desired characteristic, such as modification, so long as the ability to produce the objective protein is not spoiled. The microorganism having a desired characteristic can be obtained by, for example, modifying *Talaromyces cellulolyticus* such as the strains exemplified above. Examples of the modification include a modification for improving the ability of the produce objective protein of *Talaromyces cellulolyticus*. Specific examples of the modification include modification of reducing the activity of a GH1-2 protein, modification of introducing a mutation into the GH1-2 protein, modification of reducing the activity of beta-glucosidase, modification of reducing the activity of a CreA protein, and modification of reducing the activity of a YscB protein. These modifications can be used alone or in any appropriate combination. The order of carrying out modifications for constructing the microorganism is not particularly limited.

The microorganism may have been modified so that, for example, the activity of a GH1-2 protein is reduced and/or a gh1-2 gene has a "specific mutation". The microorganism may have been modified so that, specifically, the activity of the GH1-2 protein is reduced as compared with a non-modified strain. The microorganism may have been modified so that, more specifically, for example, the expression of the gh1-2 gene is reduced or the gh1-2 gene is disrupted. By modifying *Talaromyces cellulolyticus* so that the activity of the GH1-2 protein is reduced and/or the gh1-2 gene has the "specific mutation", the ability to produce the objective protein of *Talaromyces cellulolyticus* can be improved, and that is, production of the objective protein by *Talaromyces cellulolyticus* in the presence of the expression inducer can be increased. By modifying *Talaromyces cellulolyticus* so that the activity of the GH1-2 protein is reduced and/or the gh1-2 gene has the "specific mutation", specifically, induction of expression of the objective protein by the expression inducer may be enhanced. The phrase "induction of expression of an objective protein by an expression inducer is enhanced by modification" may mean that, for example, the degree, such as amount and ratio, of increase in production of the objective protein by the expression inducer in a modified strain is higher than the degree, such as amount and ratio, of increase in production of the objective protein by the expression inducer in a non-modified strain.

Hereinafter, the GH1-2 protein and the gh1-2 gene encoding the same will be described. The descriptions below are also applicable to the GH1-2 protein to be used for the method for producing a disaccharide, as well as the GH1-2 protein of which the activity is reduced in the microorganism. The GH1-2 protein of which the activity is reduced in the microorganism is a GH1-2 protein possessed by *Talaromyces cellulolyticus* to be modified.

The GH1-2 protein is a beta-glucosidase. The GH1-2 protein may specifically be a beta-glucosidase classified in the glucoside hydrolase family 1 (GH1). Also, the GH1-2 protein may specifically be an intracellular beta-glucosidase. The GH1-2 protein has an activity of catalyzing a reaction of synthesizing (generating) a disaccharide from a saccharide raw material and/or an activity of catalyzing a reaction of hydrolyzing a disaccharide to generate glucose. The former activity is also referred to as a "disaccharide synthesizing activity (disaccharide generating activity)" or a "transglycosylation activity". The latter activity is also referred to as a "disaccharide hydrolysis activity". The GH1-2 protein may typically have both the disaccharide synthesizing activity and the disaccharide hydrolysis activity.

The phrase "disaccharide" referred to herein refers to a disaccharide of glucose (a disaccharide constituted by two molecules of glucose). Examples of the disaccharide include beta-linked disaccharides. Specific examples of the disaccharide include gentiobiose, cellobiose, laminaribiose, and sophorose. Particular examples of the disaccharide include gentiobiose.

The phrase "saccharide raw material" referred to herein refers to a saccharide containing glucose as a constituent sugar, and includes glucose itself. The saccharide raw material may typically contain only glucose as a constituent sugar. Examples of the saccharide raw material include, for example, glucose, cello-oligosaccharides, and cellulose. Examples of the cello-oligosaccharides include, for example, cellobiose, cellotriose, and cellotetraose. Examples of cellulose include, for example, such cellulosic substrates as mentioned above. Particular examples of the saccharide raw material include glucose, cellobiose, and cellulose. More particular examples of the saccharide raw material include glucose.

The GH1-2 protein may have an activity of catalyzing a reaction of synthesizing a single kind of saccharide or two or more kinds of saccharides from a saccharide raw material. The GH1-2 protein may have an activity of catalyzing a reaction of synthesizing a saccharide from a single kind of saccharide raw material or from two or more kinds of saccharide raw material. The GH1-2 protein may have, for example, at least an activity of catalyzing a reaction of synthesizing gentiobiose from a saccharide raw material. Also, the GH1-2 protein may have, for example, at least an activity of catalyzing a reaction of synthesizing a saccharide from glucose and/or cellobiose. The GH1-2 protein may have, particularly, at least an activity of catalyzing a reaction of synthesizing a saccharide from glucose. The GH1-2 protein may have, more particularly, at least an activity of catalyzing a reaction of synthesizing gentiobiose from glucose and/or cellobiose. The GH1-2 protein may have, more particularly, at least an activity of catalyzing a reaction of synthesizing gentiobiose from glucose.

The GH1-2 protein may have an activity of catalyzing a reaction of synthesizing a saccharide from a saccharide raw material alone, or may have an activity of catalyzing a reaction of synthesizing a saccharide from a saccharide raw material when used in combination with another enzyme. Hence, the phrase "saccharide raw material" referred to in the descriptions concerning the activity of the GH1-2 protein is not limited to the saccharide raw material itself, but also includes, for example, substances converted from the saccharide raw material by another enzyme, such as degradation products of the saccharide raw material. That is, in an embodiment, the phrase "disaccharide synthesizing activity" may refer to an activity of catalyzing a reaction of synthesizing a disaccharide from a saccharide raw material or a degradation product thereof. Examples of the other enzyme include cellulase. Specifically, for example, when using cellulose as the saccharide raw material and using the GH1-2 protein and cellulase in combination, the saccharide raw material may be degraded by cellulase and a disaccharide may be generated by the GH1-2 protein from the degradation product of the saccharide raw material.

The GH1-2 protein may have an activity of catalyzing a reaction of hydrolyzing a single kind of disaccharide or two or more kinds of disaccharides. The GH1-2 protein may have, for example, at least an activity of catalyzing a reaction of hydrolyzing gentiobiose and/or cellobiose. The GH1-2 protein may have, particularly, at least an activity of catalyzing a reaction of hydrolyzing gentiobiose.

The phrase "the activity of a GH1-2 protein is reduced" referred to in the descriptions concerning the microorganism means that at least the disaccharide hydrolysis activity of the GH1-2 protein is reduced, unless otherwise stated. That is, the GH1-2 protein of which the activity is reduced in the microorganism at least has the disaccharide hydrolysis activity. When the disaccharide hydrolysis activity of the GH1-2 protein is reduced, the disaccharide synthesizing activity of the GH1-2 protein may be or may not be reduced. When the disaccharide hydrolysis activity of the GH1-2 protein is reduced, the disaccharide synthesizing activity of the GH1-2 protein can also typically be reduced together. That is, "the activity of a GH1-2 protein is reduced" may also typically mean that both the disaccharide hydrolysis activity and disaccharide synthesizing activity of the GH1-2 protein are reduced.

By modifying *Talaromyces cellulolyticus* so that the activity of the GH1-2 protein is completely eliminated, particularly, production of the objective protein by *Talaromyces cellulolyticus* in the presence of gentiobiose can be increased. By modifying *Talaromyces cellulolyticus* so that the activity of the GH1-2 protein is completely eliminated, specifically, induction of expression of the objective protein by gentiobiose may be enhanced. By modifying *Talaromyces cellulolyticus* so that the activity of the GH1-2 protein is completely eliminated, more specifically, induction of expression of the objective protein by gentiobiose may be selectively enhanced. Hence, when the microorganism has been modified so that the activity of the GH1-2 protein is completely eliminated, for example, gentiobiose may be selected as the expression inducer. The phrase "the activity of a GH1-2 protein is completely eliminated" referred to in the descriptions concerning the microorganism means that at least the disaccharide synthesizing activity of the GH1-2 protein is completely eliminated, unless otherwise stated. When the disaccharide synthesizing activity of the GH1-2 protein is completely eliminated, the disaccharide hydrolysis activity of the GH1-2 protein may be or may not be completely eliminated. When the disaccharide synthesizing activity of the GH1-2 protein is completely eliminated, the disaccharide hydrolysis activity of the GH1-2 protein can also typically be completely eliminated together. That is, the phrase "the activity of a GH1-2 protein is completely eliminated" may also typically mean that both the disaccharide synthesizing activity and disaccharide hydrolysis activity of the GH1-2 protein are completely eliminated.

Examples of the gh1-2 gene and the GH1-2 protein include those of various organisms including fungi such as *Talaromyces cellulolyticus* and other microorganisms. The nucleotide sequences of gh1-2 genes possessed by various organisms and the amino acid sequences of GH1-2 proteins encoded by them can be obtained from, for example, public databases such as NCBI (National Center for Biotechnology Information). The nucleotide sequence of the gh1-2 gene (including introns) of *Talaromyces cellulolyticus* strain Y-94 is shown as SEQ ID NO: 1, and the amino acid sequence of the GH1-2 protein encoded by this gene is shown as SEQ ID NO: 23. In addition, the nucleotide sequence of cDNA of the gh1-2 gene of *Talaromyces cellulolyticus* strain Y-94 is shown as SEQ ID NO: 22. That is, the gh1-2 gene may be, for example, a gene having the nucleotide sequence shown as SEQ ID NO: 1 or 22. Also, the GH1-2 protein may be, for example, a protein having the amino acid sequence shown as SEQ ID NO: 23. The expression "a gene or protein has a nucleotide or amino acid sequence" includes when a gene or protein includes the nucleotide or amino acid sequence unless otherwise stated, and when a gene or protein includes only the nucleotide or amino acid sequence.

The gh1-2 gene may be a variant of any of the gh1-2 genes exemplified above (such as a gene having the nucleotide sequence shown as SEQ ID NO: 1 or 22), so long as the original function thereof is maintained. Similarly, the GH1-2 protein may be a variant of any of the GH1-2 proteins exemplified above, such as a protein having the amino acid sequence shown as SEQ ID NO: 23, so long as the original function thereof is maintained. Such a variant is also referred to as "conservative variant". The term "gh1-2 gene" includes not only the gh1-2 genes exemplified above, but also includes conservative variants thereof. Similarly, the term "GH1-2 protein" includes not only the GH1-2 proteins exemplified above, but also includes conservative variants thereof. Examples of the conservative variants include, for example, homologues and artificially modified versions of the gh1-2 genes and GH1-2 proteins exemplified above.

The expression "the original function is maintained" means that a variant of a gene or protein has a function, such as activity or property, corresponding to the function, such as activity or property, of the original gene or protein. That is, the expression "the original function is maintained" used for the gh1-2 gene means that a variant of the gene encodes a protein that maintains the original function. Furthermore, the expression "the original function is maintained" used in reference to the GH1-2 protein means that a variant of the protein has the disaccharide synthesizing activity and/or the disaccharide hydrolysis activity. Incidentally, the disaccharide synthesized or hydrolyzed and the saccharide raw material used as the substrate each may be or may not be the same between a GH1-2 protein and a variant thereof.

The disaccharide synthesizing activity can be measured by incubating the enzyme with a substrate, that is, a saccharide raw material such as glucose, and measuring the enzyme- and substrate-dependent generation of a product, that is, a disaccharide such as gentiobiose. The disaccharide hydrolysis activity can be measured by incubating the enzyme with a substrate, that is, a disaccharide such as gentiobiose, and measuring the enzyme- and substrate-dependent generation of a product, such as glucose. Generation of products can be confirmed by known methods used for detection or identification of compounds, such as ion-exchange chromatography.

Hereinafter, examples of the conservative variants will be described.

Homologues of the gh1-2 genes and homologues of the GH1-2 proteins can be easily obtained from public databases by, for example, BLAST search or FASTA search using any of the nucleotide sequences of the gh1-2 genes exemplified above or any of the amino acid sequences of the GH1-2 proteins exemplified above as a query sequence. Furthermore, homologues of the gh1-2 genes can be obtained by, for example, PCR using a chromosome of organisms such as *Talaromyces cellulolyticus* as the template, and oligonucleotides prepared on the basis of any of the nucleotide sequences of these known gh1-2 genes as primers.

The gh1-2 gene may be a gene encoding a protein having any of the amino acid sequences of the GH1-2 proteins exemplified above, such as the amino acid sequence shown as SEQ ID NO: 23, but which includes substitution, deletion, insertion, and/or addition of one or several amino acid residues at one or several positions, so long as the original function thereof is maintained. Although the number meant by the term "one or several" mentioned above may differ depending on the positions of amino acid residues in the three-dimensional structure of the protein or the types of amino acid residues, specifically, it is, for example, 1 to 50, 1 to 40, 1 to 30, 1 to 20, 1 to 10, 1 to 5, or 1 to 3.

The aforementioned substitution, deletion, insertion, and/or addition of one or several amino acid residues is a conservative mutation that maintains the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, or addition of amino acid residues as mentioned above includes a naturally occurring mutation due to an individual difference, or a difference of species of the organism from which the gene is derived (mutant or variant).

The gh1-2 gene may also be a gene encoding a protein having an amino acid sequence having a homology of, for example, 80% or more, 90% or more, 95% or more, 97% or more, or 99% or more, to the total amino acid sequence of any of the amino acid sequences of the GH1-2 proteins exemplified above, such as the amino acid sequence shown as SEQ ID NO: 23, so long as the original function thereof is maintained. In this description, “homology” means “identity”.

The gh1-2 gene may also be DNA that is able to hybridize under stringent conditions with a complementary sequence of any of the nucleotide sequences of the gh1-2 genes exemplified above, such as the nucleotide sequence shown as SEQ ID NO: 1 or 22, or with a probe that can be prepared from the complementary sequence, so long as the original function thereof is maintained. The term “stringent conditions” refers to conditions under which a so-called specific hybrid is formed, and a non-specific hybrid is not formed. Examples of the stringent conditions include those under which highly homologous DNAs hybridize to each other, for example, DNAs not less than 80% homologous, less than 90% homologous, not less than 95% homologous, not less than 97% homologous, or not less than 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

The probe may be, for example, a part of a sequence that is complementary to the gene as described above. Such a probe can be prepared by PCR using oligonucleotides prepared on the basis of the nucleotide sequences of known genes as primers and a DNA fragment containing any of these nucleotide sequences as a template. As the probe, for example, a DNA fragment having a length of about 300 bp can be used. In such a case, the washing conditions of the hybridization may be, for example, 50° C., 2×SSC and 0.1% SDS.

Furthermore, the gh1-2 gene may be a gene in which any codon(s) is/are replaced with respective equivalent codon(s). That is, the gh1-2 gene may be a variant of any of the gh1-2 genes exemplified above due to the degeneracy of the genetic code. For example, the gh1-2 gene may have been modified so that it has optimal codons according to codon frequencies in a chosen host.

The percentage of the sequence identity between two sequences can be determined by, for example, using a mathematical algorithm. Non-limiting examples of such a mathematical algorithm include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program include, but are not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244, Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST (BLAST 2.0) can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other. The term “identity” between amino acid sequences may mean an identity calculated by blastp with default scoring parameters (i.e. Matrix, BLOSUM62; Gap Costs, Existence=11, Extension=1; Compositional Adjustments, Conditional compositional score matrix adjustment), unless otherwise stated. The term “identity” between nucleotide sequences may mean an identity calculated by blastn with default scoring parameters (i.e. Match/Mismatch Scores=1, −2; Gap Costs=Linear), unless otherwise stated.

The aforementioned descriptions concerning variants of the genes and proteins can also be similarly applied to any proteins such as the objective protein, and genes encoding them.

The activity of the GH1-2 protein can be reduced by, for example, attenuating the expression of the gh1-2 gene or disrupting the gh1-2 gene. Furthermore, in an embodiment, the activity of the GH1-2 protein may also be reduced by, for example, modifying the gh1-2 gene so as to have the "specific mutation". Such methods for reducing the activity of the GH1-2 protein may be used independently or in any combination.

The microorganism may have been modified so that the gh1-2 gene has the "specific mutation".

The "specific mutation" is a mutation that improves the objective protein-producing ability of *Talaromyces cellulolyticus*. The term "specific mutation" in reference to the gh1-2 gene can refer to a change in the nucleotide sequence of the gh1-2 gene. The "specific mutation" can provide a change in the amino acid sequence of the encoded the GH1-2 protein. Hence, the term "specific mutation" may also be used for the GH1-2 protein as a term referring to a change in the amino acid sequence of the GH1-2 protein provided by the "specific mutation" in the gh1-2 gene. That is, the expression "a gh1-2 gene has the "specific mutation"" may be read as that the GH1-2 protein encoded by the gene has the "specific mutation".

A GH1-2 protein having the "specific mutation" can also be referred to as a "mutant GH1-2 protein". A gene encoding a mutant GH1-2 protein, that is, a gh1-2 gene having the "specific mutation", can also be referred to as a "mutant gh1-2 gene".

A GH1-2 protein not having the "specific mutation" can also be referred to as a "wild-type GH1-2 protein". A gene encoding a wild-type GH1-2 protein, that is, a gh1-2 gene not having the "specific mutation", can also be referred to as a "wild-type gh1-2 gene". Examples of the wild-type gh1-2 gene or the wild-type GH1-2 protein include, for example, the gh1-2 genes or the GH1-2 proteins exemplified above and conservative variants thereof.

The "specific mutation" is not particularly limited, so long as the mutation improves the objective protein-producing ability of *Talaromyces cellulolyticus*. The "specific mutation" may be, for example, a mutation that reduces the activity of the GH1-2 protein. The "specific mutation" may be, for example, a mutation that reduces at least the disaccharide hydrolysis activity of the GH1-2 protein. Also, the "specific mutation" may be, for example, a mutation that does not completely eliminate the activity of the GH1-2 protein, i.e. the activity of the GH1-2 protein may remain after introduction of the mutation. The "specific mutation" may be, for example, a mutation that does not completely eliminate the disaccharide hydrolysis activity of the GH1-2 protein, i.e. the disaccharide hydrolysis activity of the GH1-2 protein may remain after introduction of the mutation.

Specific examples of the "specific mutation" include the following mutations:

(A) a mutation of replacing the cysteine residue at position 267 (C267) of the wild-type GH1-2 protein with another amino acid residue;

(B) a mutation of replacing the tryptophan residue at position 363 (W363) of the wild-type GH1-2 protein with another amino acid residue;

(C) a mutation of replacing the tryptophan residue at position 449 (W449) of the wild-type GH1-2 protein with another amino acid residue.

In each of the aforementioned mutations, the amino acid residue after the modification may be any amino acid residue other than the amino acid residue before the modification, so long as the mutation improves the objective protein-producing ability of *Talaromyces cellulolyticus*. Examples of the amino acid residue after modification include K (Lys), R (Arg), H (His), A (Ala), V (Val), L (Leu), I (Ile), G (Gly), S (Ser), T (Thr), P (Pro), F (Phe), W (Trp), Y (Tyr), C (Cys), M (Met), D (Asp), E (Glu), N (Asn), and Q (Gln). Particular examples of the amino acid residue after modification include P(Pro) for C267, F (Phe) for W363, and F(Phe) for W449. That is, particular examples of the "specific mutation" include a mutation of replacing C267 with P(Pro) (C267P mutation), a mutation of replacing W363 with F(Phe) (W363F mutation) and a mutation of replacing W449 with F(Phe) (W449F mutation).

The terms "C267", "W363", and "W449" in any chosen wild-type GH1-2 protein can refer to "an amino acid residue corresponding to the cysteine residue at position 267 in SEQ ID NO: 23", "an amino acid residue corresponding to the tryptophan residue at position 363 in SEQ ID NO: 23", and "an amino acid residue corresponding to the tryptophan residue at position 449 in SEQ ID NO: 23", respectively. The positions of these amino acid residues represent relative positions, and their absolute positions may shift due to deletion, insertion, addition, and so forth of amino acid residue(s). For example, if one amino acid residue is deleted or inserted at a position on the N-terminus side of position X in the amino acid sequence shown as SEQ ID NO: 23, the amino acid residue originally at position X is relocated to position X-1 or X+1, however, it is still regarded as the "amino acid residue corresponding to the amino acid residue at position X of the amino acid sequence shown as SEQ ID NO: 23". Furthermore, although "C267", "W363", and "W449" are typically a cysteine residue, a tryptophan residue, and a tryptophan residue, respectively, it is also acceptable that they are not a cysteine residue, a tryptophan residue, and a tryptophan residue, respectively. That is, when "C267", "W363", and "W449" are not a cysteine residue, a tryptophan residue, and a tryptophan residue, respectively, the "specific mutation" may include a mutation that those amino acid residues each are replaced with any of the aforementioned amino acid residues after mutation.

In the amino acid sequence of any chosen GH1-2 protein, which amino acid residue is the amino acid residue corresponding to "C267", "W363", or "W449" can be determined by aligning the amino acid sequence of the chosen GH1-2 protein and the amino acid sequence of SEQ ID NO: 23. The alignment can be performed by, for example, using known gene analysis software. Specific examples of such software include DNASIS produced by Hitachi Solutions, GENETYX produced by Genetyx, and so forth (Elizabeth C. Tyler et al., Computers and Biomedical Research, 24 (1) 72-96, 1991; Barton G J et al., Journal of Molecular Biology, 198 (2), 327-37, 1987).

A mutant gh1-2 gene can be obtained by, for example, modifying a wild-type gh1-2 gene so that the GH1-2 protein encoded thereby has the "specific mutation". The wild-type gh1-2 gene to be modified can be obtained by, for example, cloning from an organism having the wild-type gh1-2 gene, or chemical synthesis. Alternatively, a mutant gh1-2 gene can also be obtained without using a wild-type gh1-2 gene. For example, a mutant gh1-2 gene may be directly obtained by, for example, cloning from an organism having the mutant gh1-2 gene, or chemical synthesis. The obtained mutant gh1-2 gene may be used as it is, or may be further modified before use. Genes can be modified by known methods. For example, an objective mutation can be introduced into a target site of DNA by the site-specific mutagenesis method. The wild-type gh1-2 gene to be modified or the mutant gh1-2 gene may be or may not be derived from the host.

Methods for modifying *Talaromyces cellulolyticus* so that the gh1-2 gene has the "specific mutation" are not particularly limited. The phrase "*Talaromyces cellulolyticus* is modified so that a gene encoding the GH1-2 protein has the "specific mutation"" may specifically mean that *Talaromyces cellulolyticus* is modified so as to have a mutant gh1-2 gene instead of a native wild-type gh1-2 gene. The phrase "*Talaromyces cellulolyticus* has a mutant gh1-2 gene instead of a native wild-type gh1-2 gene" can mean that *Talaromyces cellulolyticus* has the mutant gh1-2 gene while it no longer has the normally-functional native wild-type gh1-2 gene, that is, the native wild-type gh1-2 gene has been modified so as not to normally function. The phrase "native wild-type gh1-2 gene" can refer to a wild-type gh1-2 gene inherently present in *Talaromyces cellulolyticus. Talaromyces cellulolyticus* can be modified so that the gh1-2 gene has the "specific mutation" by, for example, introducing a mutant gh1-2 gene into *Talaromyces cellulolyticus*. In such a case, the native wild-type gh1-2 gene on the chromosome or the like of *Talaromyces cellulolyticus* should be modified, e.g. disrupted or deleted, in such a manner that the objective protein-producing ability of *Talaromyces cellulolyticus* is improved in combination with the introduction of the mutant gh1-2 gene. For example, the native wild-type gh1-2 gene may be replaced with the mutant gh1-2 gene, or may be disrupted or deleted independently from the introduction of the mutant gh1-2 gene. Alternatively, *Talaromyces cellulolyticus* can also be modified so that the gh1-2 gene has the "specific mutation" by, for example, introducing the "specific mutation" into a wild-type gh1-2 gene, such as the native wild-type gh1-2 gene, on the chromosome or the like of *Talaromyces cellulolyticus*. A mutation can be introduced into a gene on a chromosome or the like by, for example, natural mutation, mutagenesis treatment, or genetic engineering.

Furthermore, the microorganism may have been modified so that, for example, the activity of a beta-glucosidase is reduced. The microorganism may have been modified so that, specifically, the activity of the beta-glucosidase is reduced as compared with a non-modified strain. The microorganism may have been modified so that, more specifically, for example, the expression of a beta-glucosidase gene is reduced or a beta-glucosidase gene is disrupted. The phrase "beta-glucosidase" refers to a protein (enzyme) having a disaccharide synthesizing activity and/or a disaccharide hydrolysis activity. The beta-glucosidase may typically have both the disaccharide synthesizing activity and the disaccharide hydrolysis activity. The description concerning the activity of the GH1-2 protein can be similarly applied to the activity of the beta-glucosidase. For example, the phrase "the activity of a beta-glucosidase is reduced" referred to in the descriptions concerning the microorganism means that at least the disaccharide hydrolysis activity of the beta-glucosidase is reduced, unless otherwise stated. That is, the beta-glucosidase of which the activity is reduced in the microorganism at least has the disaccharide hydrolysis activity. By modifying *Talaromyces cellulolyticus* so that the activity of the beta-glucosidase is reduced, it is expected that the objective protein-producing ability of *Talaromyces cellulolyticus* can be improved, and that is, production of the objective protein by *Talaromyces cellulolyticus* in the presence of the expression inducer can be increased.

The beta-glucosidase may be an intracellular-type enzyme or an extracellular-secretion-type enzyme. Examples of the beta-glucosidase include beta-glucosidases other than the GH1-2 protein. Examples of the beta-glucosidases other than the GH1-2 protein include a BGL3A protein. The BGL3A protein may specifically be a beta-glucosidase classified to glucoside hydrolase family 3 (GH3). Also, the BGL3A protein may specifically be an extracellular-secretion-type beta-glucosidase.

Examples of the beta-glucosidase gene and the beta-glucosidase include those of various organisms including fungi such as *Talaromyces cellulolyticus* and other microorganisms. The nucleotide sequences of beta-glucosidase genes possessed by various organisms and the amino acid sequences of beta-glucosidases encoded by them can be obtained from, for example, public databases such as NCBI (National Center for Biotechnology Information). The nucleotide sequence of cDNA of the bgl3A gene of *Talaromyces cellulolyticus* is shown as SEQ ID NO: 48, and the amino acid sequence of the BGL3A protein encoded by this gene is shown as SEQ ID NO: 38. That is, the beta-glucosidase gene may be, for example, a gene having the nucleotide sequence shown as SEQ ID NO: 48. Also, the beta-glucosidase may be, for example, a protein having the amino acid sequence shown as SEQ ID NO: 38. The beta-glucosidase gene and the beta-glucosidase may be a conservative variant of any of the beta-glucosidase genes and beta-glucosidases exemplified above, such as a variant of the bgl3A genes and BGL3A proteins exemplified above, respectively. The descriptions concerning conservative variants of the gh1-2 gene and the GH1-2 protein can be applied similarly to conservative variants of the beta-glucosidase gene and the beta-glucosidase. Incidentally, the expression "the original function is maintained" used in reference to the beta-glucosidase means that a variant of the protein has the disaccharide synthesizing activity and/or the disaccharide hydrolysis activity.

The descriptions concerning the beta-glucosidase are also applicable to the beta-glucosidase to be used for the method for producing a disaccharide, as well as the beta-glucosidase of which the activity is reduced in the microorganism. The beta-glucosidase of which the activity is reduced in the microorganism is a beta-glucosidase possessed by *Talaromyces cellulolyticus* to be modified.

Furthermore, the microorganism may have been modified so that, for example, the activity of a CreA protein is reduced. The microorganism may have been modified so that, specifically, the activity of the CreA protein is reduced as compared with a non-modified strain. The microorganism may have been modified so that, more specifically, for example, the expression of a creA gene is reduced or a creA gene is disrupted. The creA gene is a gene encoding a transcription factor involved in catabolite repression. The creA gene is known to be involved in the expression of cellulase (Mol Gen Genet. 1996 Jun. 24; 251(4):451-60, Biosci Biotechnol Biochem. 1998 December; 62(12):2364-70) in filamentous fungi. By modifying *Talaromyces cellulolyticus* so that the activity of the CreA protein is reduced, it is expected that the objective protein-producing ability of *Talaromyces cellulolyticus* can be improved, and that is, production of the objective protein by *Talaromyces cellulolyticus* in the presence of the expression inducer can be increased.

The nucleotide sequence of the creA gene of *Talaromyces cellulolyticus* strain S6-25 is shown as SEQ ID NO: 47. That is, the creA gene may be, for example, a gene having the nucleotide sequence shown as SEQ ID NO: 47. Also, the CreA protein may be, for example, a protein having the amino acid sequence encoded by the nucleotide sequence shown as SEQ ID NO: 47. The creA gene and the CreA protein may be a conservative variant of the creA gene and CreA protein exemplified above, respectively. The descriptions concerning conservative variants of the gh1-2 gene and the GH1-2 protein can be applied similarly to conservative variants of the creA gene and the CreA protein. Incidentally, the expression "the original function is maintained" used for the CreA protein means that a variant of the protein has a function as a transcription factor involved in catabolite repression.

Furthermore, the microorganism may have been modified so that, for example, the activity of a YscB protein is reduced. The microorganism may have been modified so that, specifically, the activity of the YscB protein is reduced as compared with a non-modified strain. The microorganism may have been modified so that, more specifically, for example, the expression of a yscB gene is reduced or a yscB gene is disrupted. The YscB protein is a protease. The phrase "protease" refers to a protein having an activity of catalyzing a reaction of hydrolyzing a protein. This activity is also referred to as a "protease activity". By modifying *Talaromyces cellulolyticus* so that the activity of the YscB protein is reduced, it is expected that the objective protein-producing ability of *Talaromyces cellulolyticus* can be improved, and that is, production of the objective protein by *Talaromyces cellulolyticus* in the presence of the expression inducer can be increased.

The nucleotide sequence of the yscB gene (including introns) of *Talaromyces cellulolyticus* strain S6-25 is shown as SEQ ID NO: 62, and the amino acid sequence of the YscB protein encoded by this gene is shown as SEQ ID NO: 69. That is, the yscB gene may be, for example, a gene having the nucleotide sequence shown as SEQ ID NO: 62. Also, the YscB protein may be, for example, a protein having the amino acid sequence shown as SEQ ID NO: 69. The yscB gene and the YscB protein may be a conservative variant of the yscB gene and YscB protein exemplified above, respectively. The descriptions concerning conservative variants of the gh1-2 gene and the GH1-2 protein can be applied similarly to conservative variants of the yscB gene and the YscB protein. Incidentally, the expression "the original function is maintained" used for the YscB protein means that a variant of the protein has the protease activity.

The protease activity can be measured by incubating the enzyme with a substrate (a protein), and measuring the enzyme-dependent degradation of the substrate. The protease activity can also be measured by using a commercial kit for measuring the protease activity.

<1-2-4> Method for Reducing Activity of Protein

Hereinafter, methods for reducing the activity of a protein including the beta-glucosidase such as the GH1-2 and BGL3A proteins, the CreA protein, and the YscB protein, will be described. The methods for reducing the activity of a protein described below can also be utilized for disruption of the wild-type PhoS protein.

The expression "the activity of a protein is reduced" means that the activity of the protein is reduced as compared with a non-modified strain. Specifically, the expression "the activity of a protein is reduced" means that the activity of the protein per cell is reduced as compared with that of a non-modified strain. The term "non-modified strain" used herein refers to a control strain that has not been modified so that the activity of an objective protein is reduced. Examples of the non-modified strain include a wild-type strain and parent strain. Specific examples of the non-modified strain include strains exemplified above in relation to the description of *Talaromyces cellulolyticus*. That is, in an embodiment, the activity of a protein may be reduced as compared with *Talaromyces cellulolyticus* strain S6-25. In another embodiment, the activity of a protein may also be reduced as compared with *Talaromyces cellulolyticus* strain Y-94. The phrase that "the activity of a protein is reduced" also includes when the activity of the protein has completely disappeared. More specifically, the expression "the activity of a protein is reduced" may mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the gene (i.e. the amount of the protein). The expression "the number of molecules of the protein per cell is reduced" also includes when the protein does not exist at all. The expression "the function of each molecule of the protein is reduced" also includes when the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The expression "the expression of a gene is reduced" means that the expression of the gene is reduced as compared with a non-modified strain. Specifically, the expression "the expression of a gene is reduced" means that the expression of the gene per cell is reduced as compared with that of a non-modified strain. More specifically, the expression "the expression of a gene is reduced" may mean that the transcription amount of the gene, i.e. the amount of mRNA, is reduced, and/or the translation amount of the gene, i.e. the amount of the protein expressed from the gene, is reduced. The expression "the expression of a gene is reduced" also includes when the gene is not expressed at all. The expression "the expression of a gene is reduced" is also referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or both. The expression of a gene can be reduced by modifying an expression control sequence of the gene. The term "expression control sequence" collectively refers to sites that affect the expression of a gene, such as a promoter. Expression control sequences can be identified by, for example, using a promoter search vector or gene analysis software such as GENETYX. When an expression control sequence is modified, one or more nucleotides, two or more nucleotides, three or more nucleotides, of the expression control sequence are modified. The transcription efficiency of a gene can be reduced by, for example, replacing the promoter of the gene on a chromosome with a weaker promoter. The term "weaker promoter" means a promoter providing an attenuated transcription of a gene compared with an inherent wild-type promoter of the gene. Examples of weaker promoters include, for example, inducible promoters. That is, an inducible promoter may function as a weaker promoter under a non-induced condition, such as in the absence of the corresponding inducer. Furthermore, a partial region or the whole region of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described herein.

The modification for reducing the activity of a protein can also be attained by, for example, disrupting a gene encoding the protein. The expression "a gene is disrupted" means that a gene is modified so that a protein that can normally function is not produced. The expression that "a protein that normally functions is not produced" includes when the protein is not produced at all from the gene, and when the protein with reduced or eliminated function, such as activity or property, per molecule is produced from the gene.

Disruption of a gene can be attained by, for example, deleting the gene on a chromosome. The term "deletion of a gene" refers to deletion of a partial or entire region of the coding region of the gene. Furthermore, the whole of a gene including sequences upstream and downstream from the coding region of the gene on a chromosome may be deleted. The sequences upstream and downstream from the coding region of the gene may include, for example, an expression control sequence of the gene. The region to be deleted may be any region such as an N-terminal region, that is a region encoding an N-terminal region of a protein, an internal region, or a C-terminal region, that is a region encoding a C-terminal region of a protein, so long as the activity of the protein can be reduced. Deletion of a longer region can usually more surely inactivate the gene. The region to be deleted may be, for example, a region having a length of 10% or more, 20% or more, 30% or more, 40% or more, 50% or more, 60% or more, 70% or more, 80% or more, 90% or more, or 95% or more of the total length of the coding region of the gene. Furthermore, it is preferred that reading frames of the sequences upstream and downstream from the region to be deleted are not the same. Inconsistency of reading frames may cause a frameshift downstream of the region to be deleted. In the case of the creA gene, specifically, for example, this gene can be disrupted by deleting a region corresponding to positions 3262 to 4509 of SEQ ID NO: 47.

Disruption of a gene can also be attained by, for example, introducing a mutation for an amino acid substitution (missense mutation), a stop codon (nonsense mutation), addition or deletion of one or two nucleotide residues (frame shift mutation), or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another nucleotide sequence into a coding region of the gene on a chromosome. Site of the insertion may be in any region of the gene, and insertion of a longer nucleotide sequence can usually more surely inactivate the gene. It is preferred that reading frames of the sequences upstream and downstream from the insertion site are not the same. Inconsistency of reading frames may cause a frameshift downstream of the region to be deleted. The other nucleotide sequence is not particularly limited so long as a sequence that reduces or eliminates the activity of the encoded protein is chosen, and examples thereof include, for example, marker genes and genes useful for production of the objective protein.

Particularly, disruption of a gene may be carried out so that the amino acid sequence of the encoded protein is deleted. In other words, the modification for reducing the activity of a protein can be attained by, for example, deleting the amino acid sequence, such as a partial or the entire region of the amino acid sequence, of the protein, specifically, modifying a gene so as to encode a protein of which the amino acid sequence, such as a partial or the entire region of the amino acid sequence, is deleted. The term "deletion of the amino acid sequence of a protein" refers to deletion of a partial or entire region of the amino acid sequence of the protein. In addition, the term "deletion of the amino acid sequence of a protein" means that the original amino acid sequence disappears in the protein, and also includes when the original amino acid sequence is changed to another amino acid sequence. That is, for example, a region that was changed to another amino acid sequence by frameshift may be regarded as a deleted region. When the amino acid sequence of a protein is deleted, the total length of the protein is typically shortened, but there can also be cases where the total length of the protein is not changed or is extended. For example, by deletion of a partial or entire region of the coding region of a gene, a region encoded by the deleted region can be deleted in the encoded protein. In addition, for example, by introduction of a stop codon into the coding region of a gene, a region encoded by the downstream region of the introduction site can be deleted in the encoded protein. In addition, for example, by frameshift in the coding region of a gene, a region encoded by the frameshift region can be deleted in the encoded protein. The aforementioned descriptions concerning the position and length of the region to be deleted in deletion of a gene can be applied similarly to the position and length of the region to be deleted in deletion of the amino acid sequence of a protein.

Such modification of a gene on a chromosome as described above can be attained by, for example, preparing a disruption-type gene modified so that it is unable to produce a protein that normally functions, and transforming a host with a recombinant DNA containing the disruption-type gene to cause homologous recombination between the disruption-type gene and the wild-type gene on a chromosome and thereby substitute the disruption-type gene for the wild-type gene on the chromosome. In this procedure, if a marker gene selected according to the characteristics of the host such as auxotrophy is included in the recombinant DNA, the operation becomes easier. Examples of the disruption-type gene include a gene of which a partial or entire region of the coding region is deleted, gene including a missense mutation, gene including a nonsense mutation, gene including a frame shift mutation, and gene inserted with an insertion sequence such as a transposon or marker gene. The protein encoded by the disruption-type gene has a conformation different from that of the wild-type protein, even if it is produced, and thus the function thereof is reduced or eliminated.

The structure of the recombinant DNA to be used for homologous recombination is not particularly limited as long as it causes homologous recombination in a desired manner. For example, a host can be transformed with a linear DNA containing any chosen sequence and further containing upstream and downstream sequences of the substitution target region on the chromosome at the respective ends, so that homologous recombination occurs at each of upstream and downstream sides of the substitution target region, to thereby replace the substitution target region with the chosen sequence in one step. As such a chosen sequence, for example, a sequence containing a marker gene can be used.

The marker gene can be appropriately selected according to the phenotype such as auxotrophy of the host. For example, when the host shows uracil auxotrophy due to mutation in a pyrF or pyrG gene, a strain introduced with a desired modification can be selected by using a pyrF or pyrG gene as marker gene and using complementation of uracil auxotrophy, i.e. using uracil prototroph, as an indicator. Also, for example, when the host shows methionine auxotrophy due to mutation in a sC gene (sulfate permease gene), a strain introduced with a desired modification can be selected by using a sC gene as a marker gene and using complementation of methionine auxotrophy, i.e. using methionine prototroph, as an indicator. Furthermore, as the marker gene, a drug resistance gene such as hygromycin resistance gene can be used.

Modification for reducing activity of a protein can also be attained by, for example, a mutagenesis treatment. Examples of the mutagenesis treatment include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

A reduction in the activity of a protein can be confirmed by measuring the activity of the protein. The activity of the beta-glucosidase such as the GH1-2 and BGL3A proteins and the activity of the YscB protein can be measured, for example, as described above. The activity of the CreA protein can be measured by, for example, measuring the degree of catabolite repression. The degree of catabolite repression can be measured by, for example, measuring cellulase production under culture conditions containing glucose as a carbon source. That is, specifically, a reduction in the activity of the CreA protein can be confirmed, for example, on the basis of, as an indicator, improvement in cellulase production under culture conditions containing glucose as a carbon source.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridization, RT-PCR, microarray, RNA-seq, and so forth (Sambrook, J., et al., Molecular Cloning A Laboratory Manual/Third Edition, Cold Spring Harbor Laboratory Press, Cold Spring Harbor (USA), 2001). The amount of mRNA, such as the number of molecules of the mRNA per cell, may be reduced to, for example, 50% or less, 20% or less, 10% or less, 5% or less, or 0% of that of a non-modified strain.

A reduction in the amount of a protein can be confirmed by Western blotting using antibodies (Sambrook, J., et al., Molecular Cloning A Laboratory Manual/Third Edition, Cold Spring Harbor Laboratory Press, Cold Spring Harbor (USA) 2001). The amount of the protein, such as the number of molecules of the protein per cell, may be reduced to, for example, 50% or less, 20% or less, 10% or less, 5% or less, or 0% of that of a non-modified strain.

Disruption of a gene can be confirmed by determining nucleotide sequence of a part or the whole of the gene, restriction enzyme map, full length, or the like of the gene depending on the means used for the disruption. Transformation can be carried out by, for example, a method generally used for transformation of eukaryotic microorganisms such fungi and yeasts. Examples of such a method include the protoplast method.

<1-3> Method for Producing Objective Protein

By using the expression inducer and the microorganism, the objective protein can be produced. Specifically, by culturing the microorganism in the presence of the expression inducer, the objective protein can be produced. That is, the method for producing the objective protein may specifically include the step of culturing the microorganism in a culture medium containing the expression inducer. Production of the objective protein by the microorganism can be induced by the expression inducer.

The culture medium to be used is not particularly limited, so long as it contains the expression inducer, the microorganism can proliferate, and the objective protein is produced. As the culture medium, for example, a liquid culture medium containing a carbon source, nitrogen source, phosphate source, sulfur source, and ingredients selected from other various organic and inorganic ingredients as required in addition to the expression inducer can be used. The types and concentrations of the culture medium components can be appropriately chosen by those skilled in the art. Regarding specific culture medium compositions, for example, culture medium compositions disclosed in prior reports concerning *Talaromyces cellulolyticus* (Japanese Patent Laid-open (Kokai) No. 2003-135052, Japanese Patent Laid-open (Kokai) No. 2008-271826, Japanese Patent Laid-open (Kokai) No. 2008-271927, etc.) or culture medium compositions used for culturing other various cellulase-producing microorganisms such as *Trichoderma reesei* can be used as a reference.

The carbon source is not particularly limited, so long as the microorganism can utilize it and produce the objective protein. Examples of the carbon source include, for example, saccharides and cellulosic substrates. Specific examples of the saccharides include, for example, glucose, fructose, galactose, xylose, arabinose, sucrose, lactose, cellobiose, blackstrap molasses, hydrolysate of starch, and hydrolysate of biomass. Specific examples of the cellulosic substrates include, for example, microcrystalline cellulose (Avicel), filter paper, waste paper, pulp, wood, rice straw, wheat straw, rice husk, rice bran, wheat bran, sugarcane bagasse, coffee grounds, and tea lees. The cellulosic substrate may also be used after being subject to a pretreatment such as hydrothermal decomposition treatment, acid treatment, alkaline treatment, steaming, blasting, and grinding. Examples of commercially-available cellulosic substrates include Solka-floc (International Fiber Corp, North Tonawanda, N.Y., U.S.A). As the carbon source, one kind of carbon source may be used, or two or more kinds of carbon sources may be used in combination. Incidentally, the expression inducer itself can be used as a carbon source. When the expression inducer is used as a carbon source, the expression inducer may be or may not be used as the sole carbon source. The expression inducer can be used in combination with another carbon source.

Specific examples of the nitrogen source include, for example, ammonium salts such as ammonium sulfate, ammonium chloride, and ammonium phosphate, organic nitrogen sources such as peptone, yeast extract, meat extract, corn steep liquor, and soybean protein decomposition product, ammonia, and urea. As the nitrogen source, one kind of nitrogen source may be used, or two or more kinds of nitrogen sources may be used in combination.

Specific examples of the phosphate source include, for example, phosphate salts such as potassium dihydrogenphosphate and dipotassium hydrogenphosphate, and phosphoric acid polymers such as pyrophosphoric acid. As the phosphate source, one kind of phosphate source may be used, or two or more kinds of phosphate sources may be used in combination.

Specific examples of the sulfur source include, for example, inorganic sulfur compounds such as sulfates, thiosulfates, and sulfites, and sulfur-containing amino acids such as cysteine, cystine, and glutathione. As the sulfur source, one kind of sulfur source may be used, or two or more kinds of sulfur sources may be used in combination.

Specific examples of the other various organic and inorganic components include, for example, inorganic salts such as sodium chloride, and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing these such as peptone, casamino acid, yeast extract, and soybean protein decomposition product. As the other various organic and inorganic components, one kind of component may be used, or two or more kinds of components may be used in combination.

Culture conditions are not particularly limited, so long as the microorganism can proliferate, and the objective protein is produced. The culture can be performed with, for example, conditions typically used for the culture of microorganisms such as filamentous fungi. Regarding specific culture conditions, for example, culture conditions disclosed in prior reports concerning *Talaromyces cellulolyticus* (Japanese Patent Laid-open (Kokai) No. 2003-135052, Japanese Patent Laid-open (Kokai) No. 2008-271826, Japanese Patent Laid-open (Kokai) No. 2008-271927, etc.) or culture conditions used for culturing other various cellulase-producing microorganisms such as *Trichoderma reesei* can be used as a reference.

The culture can be performed, for example, under aerobic conditions using a liquid medium. The culture under aerobic conditions can be performed, specifically, as a culture with aeration, shaking, and/or stirring. The culture temperature may be, for example, 15 to 43° C., and may particularly be approximately 30° C. The culture period may be, for example, 2 hours to 20 days. The culture can be performed as batch culture, fed-batch culture, continuous culture, or a combination of these. The culture medium used at the start of the culture can also be referred to as "starting medium". The culture medium supplied to the culture system (e.g. fermentation tank) in the fed-batch culture or the continuous culture can also be referred to as "feed medium". To supply a feed medium to the culture system in the fed-batch culture or the continuous culture can also be referred to as "feed". The culture may also be performed separately as a seed culture and a main culture. For example, the seed culture may be performed using a solid medium such as an agar medium, and the main culture may be performed using a liquid medium. The culture may be continued, for example, until the carbon source present in the culture medium is consumed, or until the activity of the microorganism is lost.

The culture medium components each may be present in the starting medium, the feed medium, or both. The types of the components present in the starting medium may be or may not be the same as those of the components present in the feed medium. Furthermore, the concentrations of the components present in the starting medium may be or may not be the same as the concentrations of the components present in the feed medium. Furthermore, two or more kinds of feed media having components of different types and/or different concentrations may be used. For example, when feeding is intermittently performed two or more times, the types and/or concentrations of components contained in the feed medium may be or may not be the same for each feeding.

The expression inducer may be present in the culture medium over the whole period of the culture, or may be present in the culture medium during only a partial period of the culture. That is, the phrase "cultivating the microorganism in a culture medium containing an expression inducer" does not necessarily mean that the expression inducer is present in the culture medium over the whole period of the culture. For example, the expression inducer may be or may not be present in the culture medium from the start of the culture. When the expression inducer is not present in the culture medium at the time of the start of the culture, the expression inducer is supplied to the culture medium after the start of the culture. The timing of the supply can be appropriately determined according to various conditions such as the length of the culture period. For example, the expression inducer may be supplied to the culture medium after growth of microbial cells. The timing of the supply may specifically be a time point on or after 3 hours, 6 hours, 10 hours, or 20 hours after the start of the culture. Furthermore, the phrase "a partial period" may refer to, for example, a period of 10% or longer, 20% or longer, 30% or longer, 40% or longer, 50% or longer, 60% or longer, 70% or longer, 80% or longer, 90% or longer, or 95% or longer of the whole period of the culture. The expression inducer may be or may not be consumed during the culture. In any cases, expression inducer may be additionally supplied to the culture medium. Means for supplying the expression inducer to the culture medium are not particularly limited. For example, the expression inducer can be supplied to the culture medium by feeding a feed medium containing the expression inducer to the culture medium. Such a feed medium may or may not contain only the expression inducer. Such a feed medium may contain, for example, a carbon source such as glucose in addition to the expression inducer. The concentration of the expression inducer in the culture medium is not particularly limited so long as expression of the objective protein is induced. The concentration of the expression inducer in the culture medium, for example, may be 0.0005 g/L or higher, 0.001 g/L or higher, 0.003 g/L or higher, 0.005 g/L or higher, 0.01 g/L or higher, 0.05 g/L or higher, 0.1 g/L or higher, 0.5 g/L or higher, 1 g/L or higher, 5 g/L or higher, or 10 g/L or higher, or may be 100 g/L or lower, 50 g/L or lower, 10 g/L or lower, 5 g/L or lower, 2 g/L or lower, 1 g/L or lower, or 0.5 g/L or lower, or may be within a range defined by a non-contradictory combination thereof. The expression inducer may be or may not be present in the culture medium at a concentration within the range exemplified above over the whole period of the culture. For example, the expression inducer may be present in the culture medium at a concentration within the range exemplified above at the time of the start of the culture, or it may be supplied to the culture medium so that a concentration within the range exemplified above is attained after the start of the culture. When the culture is performed separately as a seed culture and a main culture, it is sufficient that the objective protein is produced at least during the main culture. Hence, it is sufficient that the expression inducer is present in the culture medium at least during the main culture, i.e. over the whole period of the main culture or during a partial period of the main culture, and that is, the expression inducer may be or may not be present in the culture medium during the seed culture. In such cases, phrases regarding the culture, such as the phrases “culture period (period of culture)” and “start of culture”, can be read as those regarding the main culture.

As the expression inducer, a commercial product may be used, or one appropriately prepared and obtained may be used. Methods for producing the expression inducer are not particularly limited. The expression inducer can be produced by, for example, chemical synthesis, enzymatic conversion, or both. Specifically, for example, a disaccharide such as gentiobiose may be one produced from a saccharide raw material by enzymatic conversion. That is, the method for producing the objective protein may further include producing a disaccharide such as gentiobiose from a saccharide raw material by enzymatic conversion. Methods for producing a disaccharide such as gentiobiose from a saccharide raw material by enzymatic conversion are described below.

The concentrations of various components such as the expression inducer can be measured by gas chromatography (Hashimoto, K. et al. 1996. Biosci. Biotechnol. Biochem. 70:22-30) or HPLC (Lin, J. T. et al. 1998. J. Chromatogr. A. 808: 43-49).

By culturing the microorganism as described above, the objective protein is expressed and a culture broth containing the objective protein is obtained. The objective protein may be accumulated in a culture medium, on a cell surface layer, in microbial cells, or in/on a combination thereof. The objective protein may be accumulated particularly in microbial cells.

Production of the objective protein can be confirmed by known methods used for detection or identification of proteins. Examples of such methods include, for example, SDS-PAGE, Western blotting, mass spectrometry, N-terminal amino acid sequence analysis, and enzyme activity measurement. One of these methods may be used alone, or two or more of these methods may be used in combination as required. Hereinafter, the case of a cellulase is exemplified. Production of a cellulase can be confirmed by, for example, measuring the cellulase activity in an appropriate fraction such as a culture broth and a culture supernatant. The cellulase activity can be measured by known methods. Specifically, for example, an enzymatic reaction using cellulose, such as microcrystalline cellulose (Avicel) and a filter paper, as a substrate can be carried out, and then the cellulase activity corresponding to the substrate, such as the Avicelase activity, that is an activity for degrading Avicel, and the FPase activity, that is an activity for degrading a filter paper, can be calculated using the amount of a reducing sugar generated as an indicator. The amount of a reducing sugar can be measured by known methods such as dinitrosalicylic acid (DNS) method and Somogyi-Nelson method.

The objective protein generated can be collected as required. That is, the method for producing the objective protein may include collecting the objective protein generated. Specifically, the objective protein can be collected as an appropriate fraction containing the objective protein. Examples of such a fraction include, for example, a culture broth, a culture supernatant, microbial cells, and a processed product of microbial cells, such as a disruption product, a lysate, and an extract, such as a cell-free extract. The microbial cells may also be provided, for example, in a form of immobilized cells immobilized on a carrier such as acrylamide and carrageenan.

Furthermore, the objective protein may be separated and purified to a desired extent. The objective protein may be provided in a form of a free enzyme, or may be provided in a form of an immobilized enzyme immobilized on a solid phase such as a resin.

When the objective protein is accumulated in the culture medium, for example, solids such as microbial cells can be removed from the culture broth by centrifugation or the like, and then the objective protein can be separated and purified from the culture supernatant.

When the objective protein is accumulated in microbial cells, for example, the microbial cells can be subject to a treatment such as disruption, lysis, or extraction, and then the objective protein can be separated and purified from the treated product. The microbial cells can be collected from the culture broth by centrifugation or the like. The treatment such as disruption, lysis, or extraction can be performed by known methods. Examples of such methods include, for example, disruption by ultrasonication, disruption in Dyno-Mill, disruption in bead mill, disruption with French press, and lysozyme treatment. One of these methods may be used alone, or two or more of these methods may be used in combination as required.

When the objective protein is accumulated on a cell surface layer, for example, the objective protein can be solubilized and then separated and purified from the solubilized product. Solubilization can be performed by known methods. Examples of such methods include, for example, an increase in a salt concentration and use of a surfactant. One of these methods may be used alone, or two or more of these methods may be used in combination as required.

Purification of the objective protein, such as purification of the objective protein from such a supernatant, treated product, or solubilized product as described above, can be performed by known methods used for purification of proteins. Examples of such methods include, for example, ammonium sulfate fractionation, ion exchange chromatography, hydrophobic chromatography, affinity chromatography, gel filtration chromatography, and isoelectric precipitation. One of these methods may be used alone, or two or more of these methods may be used in combination as required.

In the culture broth, enzyme(s) other than the objective protein, including cellulases, and hemicellulases such as xylanase, xylobiase (beta-xylosidase), and arabinofuranosidase, may also be produced and accumulated together with the objective protein. The objective protein may be collected as a mixture with such other enzyme(s), or may be collected separately from such other enzyme(s).

The objective protein collected may be made into a formulation as required. The dosage form of the formulation is not particularly limited, and can be appropriately chosen according to various conditions such as use purpose of the objective protein. Examples of the dosage form include, for example, solution, suspension, powder, tablet, pill, and capsule. For preparing such a formulation, for example, pharmaceutically acceptable additives such as excipients, binders, disintegrating agents, lubricants, stabilizers, corrigents, odor-masking agents, perfumes, diluents, and surfactants can be used.

The use of the objective protein is not particularly limited. Hereinafter, a cellulase is exemplified. A cellulase can be used for degradation of cellulose. For example, by saccharification of a cellulose component contained in plant biomass by using the cellulase, a saccharification solution containing glucose is obtained. In addition, when a cellulase has a hemicellulase activity such as xylanase activity, e.g. when a cellulase is obtained as a mixture with a hemicellulase, the cellulase can also be used for degradation of hemicellulose. For example, by saccharification of a hemicellulose component contained in plant biomass by using the cellulase, a saccharification solution containing xylose or arabinose is obtained. The thus-obtained saccharification solution can be used for, for example, culturing a microorganism as a carbon source. Furthermore, in an embodiment, for example, an objective substance such as an L-amino acid can be produced by culturing a microorganism. Regarding saccharification of plant biomass by a cellulase and use of the obtained saccharification solution, for example, the descriptions of Japanese Patent Laid-open (Kokai) No. 2016-131533 can be used as a reference.

<2> Method for Producing Disaccharide

The method for producing a disaccharide can use a disaccharide synthesizing enzyme. The method for producing a disaccharide may be, specifically, a method for producing a disaccharide from a saccharide raw material by enzymatic conversion using a disaccharide synthesizing enzyme. That is, in other words, the method for producing a disaccharide may be a method for producing a disaccharide including the step of converting a saccharide raw material into the disaccharide by using a disaccharide synthesizing enzyme. The enzymatic conversion can be carried out, specifically, by bringing the disaccharide synthesizing enzyme into contact with the saccharide raw material. That is, the method for producing a disaccharide may be, more specifically, a method for producing a disaccharide including bringing a disaccharide synthesizing enzyme into contact with a saccharide raw material to thereby generate the disaccharide. A reaction of generating a disaccharide from a saccharide raw material by enzymatic conversion is also referred to as "conversion reaction".

The phrase "disaccharide" referred to herein refers to a disaccharide of glucose, that is a disaccharide constituted by two molecules of glucose. Examples of the disaccharide include beta-linked disaccharides. Specific examples of the disaccharide include gentiobiose, cellobiose, laminaribiose, and sophorose. Particular examples of the disaccharide include gentiobiose. A single kind of disaccharide may be produced, or two or more kinds of disaccharides may be produced. The disaccharide may include, for example, at least gentiobiose. In other words, for example, gentiobiose may be produced alone, or a combination of gentiobiose and one or more kinds of other disaccharides may be produced.

The phrase "saccharide raw material" referred to herein refers to a saccharide containing glucose as a constituent sugar, and include glucose itself. The saccharide raw material may typically contain only glucose as a constituent sugar. The saccharide raw material can be saccharides other than the disaccharides to be produced. Examples of the saccharide raw material include, for example, glucose, cello-oligosaccharides, and cellulose. Examples of the cello-oligosaccharides include, for example, cellobiose, cellotriose, and cellotetraose. Examples of cellulose include, for example, such cellulosic substrates as mentioned above. Particular examples of the saccharide raw material include glucose, cellobiose, and cellulose. More particular examples of the saccharide raw material include glucose. As the saccharide raw material, a single kind of saccharide raw material may be used, or two or more kinds of saccharide raw materials may be used in combination. The saccharide raw material may include, for example, at least glucose. In other words, as the saccharide raw material, for example, glucose may be used alone, or glucose and one or more kinds of other saccharide raw materials may be used in combination.

<2-1> Disaccharide Synthesizing Enzyme and Production of the Same

The phrase "disaccharide synthesizing enzyme" refers to a protein (enzyme) having an activity of catalyzing a reaction of synthesizing a disaccharide from a saccharide raw material. This activity is also referred to as a "disaccharide synthesizing activity". A gene encoding a disaccharide synthesizing enzyme is also referred to as a "disaccharide synthesizing enzyme gene". The disaccharide synthesizing enzyme is not particularly limited so long as it has an activity of catalyzing a reaction of synthesizing a desired disaccharide from a saccharide raw material. The disaccharide synthesizing enzyme may have an activity of catalyzing a reaction of synthesizing a single kind of saccharide or two or more kinds of saccharides from a saccharide raw material. The disaccharide synthesizing enzyme may have an activity of catalyzing a reaction of synthesizing a saccharide from a single kind of saccharide raw material or from two or more kinds of saccharide raw material. The disaccharide synthesizing enzyme may have, for example, at least an activity of catalyzing a reaction of synthesizing gentiobiose from a saccharide raw material. Also, the disaccharide synthesizing enzyme may have, for example, at least an activity of catalyzing a reaction of synthesizing a saccharide from glucose and/or cellobiose. The disaccharide synthesizing enzyme may have, particularly, at least an activity of catalyzing a reaction of synthesizing a saccharide from glucose. The disaccharide synthesizing enzyme may have, more particularly, at least an activity of catalyzing a reaction of synthesizing gentiobiose from glucose and/or cellobiose. The disaccharide synthesizing enzyme may have, more particularly, at least an activity of catalyzing a reaction of synthesizing gentiobiose from glucose. As the disaccharide synthesizing enzyme, a single kind of disaccharide synthesizing enzyme may be used, or two or more kinds of disaccharide synthesizing enzymes may be used in combination. Examples of the disaccharide synthesizing enzyme include beta-glucosidase. Examples of the beta-glucosidase include a GH1-2 protein and a BGL3A protein. The GH1-2 protein and the BGL3A protein are described above. These beta-glucosidases can be found in, for example, fungi such *Talaromyces cellulolyticus*. Examples of the beta-glucosidase also include those described in Japanese Patent Laid-open (Kokai) No. 2010-227032 and WO2004/035070. The amino acid sequences of beta-glucosidases of various organisms the nucleotide sequences of beta-glucosidase genes encoding them can be obtained from, for example, public databases such as NCBI.

The disaccharide synthesizing enzyme gene and the disaccharide synthesizing enzyme may have any of the nucleotide sequences and amino acid sequences of known genes and proteins, such as the genes and proteins exemplified above, respectively. The disaccharide synthesizing enzyme gene and the disaccharide synthesizing enzyme may also be a conservative variant of any of known genes and proteins, such as the genes and proteins exemplified above, respectively. The descriptions concerning conservative variants of the gh1-2 gene and the GH1-2 protein can be applied similarly to conservative variants of the disaccharide synthesizing enzyme gene and the disaccharide synthesizing enzyme. Incidentally, the expression "the original function is maintained" used for the disaccharide synthesizing enzyme means that a variant of the protein has the disaccharide synthesizing activity. The disaccharide synthesized and the saccharide raw material used as the substrate each may be or may not be the same between a disaccharide synthesizing enzyme and a variant thereof.

The disaccharide synthesizing enzyme may have an activity of catalyzing a reaction of synthesizing a saccharide from a saccharide raw material alone, or may have an activity of catalyzing a reaction of synthesizing a saccharide from a saccharide raw material upon being used in combination with another enzyme. Hence, the phrase "saccharide raw material" referred to in the descriptions concerning the activity of the disaccharide synthesizing enzyme is not limited to the saccharide raw material itself, but also includes, for example, substances converted from the saccharide raw material by another enzyme, such as degradation products of the saccharide raw material. That is, in an embodiment, the phrase "disaccharide synthesizing activity" may refer to an activity of catalyzing a reaction of synthesizing a disaccharide from a saccharide raw material or a degradation product thereof. The disaccharide synthesizing enzyme may be used alone or in combination with another enzyme so long as a disaccharide can be produced from a saccharide raw material. The disaccharide synthesizing enzyme may be used in combination with another enzyme so that, for example, a disaccharide can be produced from a saccharide raw material. Specifically, for example, when using cellulose as the saccharide raw material and using the disaccharide synthesizing enzyme and cellulase in combination, the saccharide raw material may be degraded by cellulase and a disaccharide may be generated by the disaccharide synthesizing enzyme from the degradation product of the saccharide raw material.

The disaccharide synthesizing enzyme can be produced by making a host having the disaccharide synthesizing enzyme gene express the gene. The expression of a disaccharide synthesizing enzyme gene is also referred to as "expression of a disaccharide synthesizing enzyme". It is sufficient that the host having the disaccharide synthesizing enzyme gene has the disaccharide synthesizing enzyme gene so that the disaccharide synthesizing enzyme gene can be expressed. The host having the disaccharide synthesizing enzyme gene may have one copy or two or more copies of the disaccharide synthesizing enzyme gene. The host having the disaccharide synthesizing enzyme gene may have a single kind of disaccharide synthesizing enzyme gene, or may have two or more kinds of disaccharide synthesizing enzyme genes.

The disaccharide synthesizing enzyme can also be produced by expressing the disaccharide synthesizing enzyme gene in a cell-free protein synthesis system.

The host having the disaccharide synthesizing enzyme gene may be a host inherently having the disaccharide synthesizing enzyme gene, or may be a host modified so as to have the disaccharide synthesizing enzyme gene.

Examples of the host inherently having the disaccharide synthesizing enzyme gene include organisms from which such disaccharide synthesizing enzymes as mentioned above are derived, e.g. fungi such as *Talaromyces cellulolyticus*.

Examples of the host modified so as to have the disaccharide synthesizing enzyme gene include hosts introduced with the disaccharide synthesizing enzyme gene. By introducing the disaccharide synthesizing enzyme gene into a host inherently not having the disaccharide synthesizing enzyme gene, the activity of the disaccharide synthesizing enzyme of the host can be increased (the activity of the disaccharide synthesizing enzyme can be imparted to the host).

Also, the host inherently having the disaccharide synthesizing enzyme gene can be used after being modified so that the activity of the disaccharide synthesizing enzyme is increased. That is, the host having the disaccharide synthesizing enzyme gene may be a host modified so that the activity of the disaccharide synthesizing enzyme is increased.

The host is not particularly limited, so long as it can express a functional disaccharide synthesizing enzyme. Examples of the host include, for example, bacteria, fungi, plant cells, insect cells, and animal cells. Preferred examples of the host include microorganisms such as bacteria and fungi.

Examples of the bacteria include gram-negative bacteria and gram-positive bacteria. Examples of the gram-negative bacteria include, for example, bacteria belonging to the family Enterobacteriaceae, such as *Escherichia* bacteria, *Enterobacter* bacteria, and *Pantoea* bacteria. Examples of the gram-positive bacteria include *Bacillus* bacteria, coryneform bacteria such as *Corynebacterium* bacteria, and actinomycetes. Examples of the *Escherichia* bacteria include, for example, *Escherichia coli*. Specific examples of *Escherichia coli* include, for example, *Escherichia coli* K-12 strains such as W3110 strain (ATCC 27325) and MG1655 strain (ATCC 47076); *Escherichia coli* K5 strain (ATCC 23506); *Escherichia coli* B strains such as BL21(DE3) strain and Rosetta 2(DE3)pLysS strain; and derivative strains thereof. Examples of the *Corynebacterium* bacteria include, for example, *Corynebacterium glutamicum* and *Corynebacterium ammoniagenes* (*Corynebacterium* stationis).

These strains are available from, for example, the American Type Culture Collection (Address: P.O. Box 1549, Manassas, Va. 20108, United States of America). That is, registration numbers are given to the respective strains, and the strains can be ordered by using these registration numbers (refer to atcc.org). The registration numbers of the strains are listed in the catalogue of the American Type Culture Collection. These strains can also be obtained from, for example, the depositories at which the strains were deposited. In addition, these strains are available as commercial products.

Hereafter, methods for increasing the activity of a protein such as the disaccharide synthesizing enzyme, including methods for introduction of a gene such as the disaccharide synthesizing enzyme gene, will be described.

The expression "the activity of a protein is increased" means that the activity of the protein is increased as compared with a non-modified strain. Specifically, the expression "the activity of a protein is increased" may mean that the activity of the protein per cell is increased as compared with that of a non-modified strain. The term "non-modified strain" used herein refers to a control strain that has not been modified so that the activity of an objective protein is increased. Examples of the non-modified strain include a wild-type strain and parent strain. Specific examples of the non-modified strain include strains exemplified above in relation to the description of the host. The phrase that "the activity of a protein is increased" may also be expressed as "the activity of a protein is enhanced". More specifically, the expression "the activity of a protein is increased" may mean that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene (i.e. the amount of mRNA) encoding the protein, or the translation amount of the protein (i.e. the amount of the protein). Furthermore, the phrase that "the activity of a protein is increased" includes not only when the activity of an objective protein is increased in a strain inherently having the activity of the objective protein, but also when the activity of an objective protein is imparted to a strain not inherently having the activity of the objective protein. Furthermore, so long as the activity of the protein is eventually increased, the activity of an objective protein inherently contained in a host may be attenuated and/or eliminated, and then an appropriate type of the objective protein may be imparted to the host.

The degree of the increase in the activity of a protein is not particularly limited, so long as the activity of the protein is increased as compared with a non-modified strain. The activity of the protein may be increased to, for example, 1.5 times or more, 2 times or more, or 3 times or more of that of a non-modified strain. Furthermore, when the non-modified strain does not have the activity of the objective protein, it is sufficient that the protein is produced as a result of introduction of the gene encoding the protein, and for example, the protein may be produced to such an extent that the enzymatic activity thereof can be measured.

The modification for increasing the activity of a protein can be attained by, for example, increasing the expression of a gene encoding the protein. The expression "the expression of a gene is increased" means that the expression of the gene is increased as compared with a non-modified strain such as a wild-type strain or parent strain. Specifically, the expression "the expression of a gene is increased" may mean that the expression amount of the gene per cell is increased as compared with that of a non-modified strain. More specifically, the expression "the expression of a gene is increased" may mean that the transcription amount of the gene (i.e. the amount of mRNA) is increased, and/or the translation amount of the gene (i.e. the amount of the protein expressed from the gene) is increased. The phrase that "the expression of a gene is increased" can also be referred to as "the expression of a gene is enhanced". The expression of a gene may be increased to, for example, 1.5 times or more, 2 times or more, or 3 times or more of that of a non-modified strain. Furthermore, the phrase that "the expression of a gene is increased" includes not only when the expression amount of an objective gene is increased in a strain that inherently expresses the objective gene, but also when the gene is introduced into a strain that does not inherently express the objective gene, and expressed therein. That is, the phrase "the expression of a gene is increased" includes, for example, when an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination include, for example, a method of using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome can include repetitive DNAs, and inverted repeats located at the both ends of a transposon. Alternatively, homologous recombination may be performed by using an appropriate sequence on a chromosome such as a gene unnecessary for the production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector is preferably a multi-copy vector. Furthermore, the vector can have a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in Enterobacteriaceae bacteria such as *Escherichia coli* can include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pCold TF DNA (Takara Bio), pACYC series vectors, and the broad host spectrum vector RSF1010. Specific examples of vector autonomously replicable in coryneform bacteria can include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; pVK7 described in Japanese Patent Laid-open (Kokai) No. 10-215883; pVK9 described in US2006-0141588; pVC7 described in Japanese Patent Laid-open (Kokai) No. 9-070291; and pVS7 described in WO2013/069634.

When a gene is introduced, it is sufficient that the gene is expressibly harbored by a host. Specifically, it is sufficient that the gene is harbored by a host so that it is expressed under control of a promoter sequence that functions in the host. The promoter may be a promoter derived from the host, or a heterogenous promoter. The promoter may be the native promoter of the gene to be introduced, or a promoter of another gene. As the promoter, for example, such a stronger promoter as mentioned later may also be used.

A terminator for termination of gene transcription may be located downstream of the gene. The terminator is not particularly limited so long as it functions in a host. The terminator may be a terminator derived from the host, or a heterogenous terminator. The terminator may be the native terminator of the gene to be introduced, or a terminator of another gene. Specific examples of the terminator can include, for example, T7 terminator, T4 terminator, fd phage terminator, tet terminator, and trpA terminator.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Furthermore, when two or more of genes are introduced, it is sufficient that the genes each are expressively harbored by a host. For example, all the genes may be carried by a single expression vector or a chromosome. Furthermore, the genes may be separately carried by two or more expression vectors, or separately carried by a single or two or more expression vectors and a chromosome. An operon made up of two or more genes may also be introduced. Examples of "introducing two or more genes" include, for example, introducing respective genes encoding two or more kinds of proteins (such as enzymes), and/or introducing respective genes encoding two or more subunits making up a single protein complex (such as enzyme complex).

The gene to be introduced is not particularly limited so long as it encodes a protein that functions in the host. The gene to be introduced may be a gene derived from the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene (Gene, 60(1), 115-127 (1987)). The obtained gene can be used as it is, or after being modified as required. That is, a variant of a gene may be obtained by modifying the gene. A gene can be modified by a known technique. For example, an objective mutation can be introduced into an objective site of DNA by the site-specific mutation method. That is, the coding region of a gene can be modified by the site-specific mutation method so that a specific site of the encoded protein includes substitution, deletion, insertion, and/or addition of amino acid residues. Examples of the site-specific mutation method can include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a variant of a gene may be totally synthesized.

In addition, when a protein functions as a complex having a plurality of subunits, some or all of the subunits may be modified, so long as the activity of the protein is eventually increased. That is, for example, when the activity of a protein is increased by increasing the expression of a gene, the expression of some or all of the genes that encode the subunits may be enhanced. It is usually preferable to enhance the expression of all of the genes encoding the subunits. Furthermore, the subunits making up the complex may be derived from a single kind of organism or two or more kinds of organisms, so long as the complex has a function of the objective protein. That is, for example, genes of the same organism encoding a plurality of subunits may be introduced into a host, or genes of different organisms encoding a plurality of subunits may be introduced into a host.

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively refers to sites that affect the expression of a gene. Examples of the expression control sequence include, for example, promoter, Shine-Dalgarno (SD) sequence, also referred to as ribosome binding site (RBS), and spacer region between RBS and the start codon. Expression control sequences can be identified by using a promoter search vector or gene analysis software such as GENETYX. These expression control sequences can be modified by, for example, a method of using a temperature sensitive vector, or the Red driven integration method (WO2005/010175).

The transcription efficiency of a gene can be improved by, for example, replacing the promoter of the gene on a chromosome with a stronger promoter. The term "stronger promoter" means a promoter providing an improved transcription of a gene compared with an inherent wild-type promoter of the gene. Examples of stronger promoters include, for example, the known high expression promoters such as T7 promoter, trp promoter, lac promoter, thr promoter, tac promoter, trc promoter, tet promoter, araBAD promoter, rpoH promoter, msrA promoter, Pm 1 promoter (derived from the genus *Bifidobacterium*), PR promoter, and PL promoter. Examples of stronger promoters usable in coryneform bacteria include, for example, the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, and cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12):8587-96), as well as lac promoter, tac promoter, and trc promoter. Furthermore, as the stronger promoter, a highly-active inherent promoter may also be obtained by using various reporter genes. For example, by making the −35 and −10 regions in a promoter region closer to the consensus sequence, the activity of the promoter can be enhanced (WO00/18935). Examples of a highly active promoter include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence, (also referred to as ribosome binding site (RBS), for the gene on a chromosome with a stronger SD sequence. The "stronger SD sequence" means a SD sequence that provides an improved translation of mRNA compared with the inherent wild-type SD sequence of the gene. Examples of stronger SD sequences include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying them.

The translation efficiency of a gene can also be improved by, for example, modifying codons. For example, the translation efficiency of the gene can be improved by replacing a rare codon present in the gene with a synonymous codon that is more frequently used. That is, the gene to be introduced may be modified, for example, so as to contain optimal codons according to the frequencies of codons observed in a chosen host. Codons can be replaced by, for example, the site-specific mutation method for introducing an objective mutation into a target site of DNA. Alternatively, a gene fragment in which objective codons are replaced may be totally synthesized. Frequencies of codons in various organisms are disclosed in the "Codon Usage Database" (kazusa.or.jp/codon; Nakamura, Y. et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in any combination.

Furthermore, the modification that increases the activity of a protein can also be attained by, for example, enhancing the specific activity of the enzyme. Enhancement of the specific activity also includes reduction or elimination of feedback inhibition. A protein having an enhanced specific activity can be obtained by, for example, searching various organisms. Furthermore, a highly-active type of an inherent protein may also be obtained by introducing a mutation into the existing protein. The mutation to be introduced may be, for example, substitution, deletion, insertion, or addition of one or several amino acid residues at one or several positions in the protein. The mutation can be introduced by, for example, such a site-specific mutation method as mentioned above. The mutation may also be introduced by, for example, a mutagenesis treatment. Examples of the mutagenesis treatment can include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Furthermore, a random mutation may be induced by directly treating DNA in vitro with hydroxylamine. Enhancement of the specific activity may be independently used, or may be used in any combination with such methods for enhancing gene expression as mentioned above.

The method for the transformation is not particularly limited, and conventionally known methods can be used. There can be used, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1997, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Furthermore, the electric pulse method reported for coryneform bacteria (Japanese Patent Laid-open (Kokai) No. 2-207791) can also be used.

An increase in the activity of a protein can be confirmed by measuring the activity of the protein.

An increase in the activity of a protein can also be confirmed by confirming an increase in the expression of a gene encoding the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA can include Northern hybridization, RT-PCR, microarray, RNA-seq, and so forth (Sambrook, J., et al., Molecular Cloning A Laboratory Manual/Third Edition, Cold Spring Harbor Laboratory Press, Cold Spring Harbor (USA), 2001). The amount of mRNA (such as the number of molecules of the mRNA per cell) may be increased to, for example, 1.5 times or more, 2 times or more, or 3 times or more of that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein, such as the number of molecules of the protein per cell) may be increased to, for example, 1.5 times or more, 2 times or more, or 3 times or more of that of a non-modified strain.

The aforementioned methods for increasing the activity of a protein can be applied to enhancement of the activities of any proteins and enhancement of the expression of any genes such as genes encoding those proteins, besides enhancement of the activity of the disaccharide synthesizing enzyme and introduction of the disaccharide synthesizing enzyme gene.

By culturing the host having the disaccharide synthesizing enzyme gene in a culture medium, the disaccharide synthesizing enzyme can be expressed. During the culture, the expression of the disaccharide synthesizing enzyme gene can be induced as required. Conditions for induction of gene expression can be appropriately chosen depending on various conditions such as the structure of gene expression system.

Culture medium compositions and culture conditions are not particularly limited, so long as the host having the disaccharide synthesizing enzyme gene can proliferate, and the disaccharide synthesizing enzyme can be produced. The culture medium compositions and culture conditions can be appropriately chosen depending on various conditions such as the type of the host. The culture can be carried out, for example, using a usual culture medium under usual conditions used for culturing microorganisms such as bacteria and fungi. Regarding specific culture medium compositions and culture conditions for culturing bacteria, for example, culture medium compositions and culture conditions used for production of various substances using bacteria such as *E. coli* and coryneform bacteria can be used as a reference. Regarding specific culture medium compositions and culture conditions for culturing fungi, for example, culture medium compositions and culture conditions disclosed in prior reports concerning *Talaromyces cellulolyticus* (Japanese Patent Laid-open (Kokai) No. 2003-135052, Japanese Patent Laid-open (Kokai) No. 2008-271826, Japanese Patent Laid-open (Kokai) No. 2008-271927, etc.) or culture medium compositions and culture conditions used for culturing other various cellulase-producing microorganisms such as *Trichoderma reesei* can be used as a reference. Furthermore, regarding the culture medium compositions and culture conditions, for example, the culture medium compositions and culture conditions in the method for producing the objective protein can also be used as a reference, except that the culture medium need not contain the expression inducer for culturing the host having the disaccharide synthesizing enzyme gene.

As the culture medium, for example, a liquid culture medium containing a carbon source, nitrogen source, phosphate source, sulfur source, and ingredients selected from other various organic and inorganic ingredients as required can be used. The types and concentrations of the culture medium components can be appropriately chosen by those skilled in the art. The carbon source is not particularly limited, so long as the host having the disaccharide synthesizing enzyme gene can utilize it. Examples of the carbon source include, for example, those mentioned above such as saccharides and cellulosic substrates. Examples of the carbon source also include, for example, organic acids such as acetic acid, fumaric acid, citric acid, succinic acid, and malic acid, alcohols such as glycerol, crude glycerol, and ethanol, and aliphatic acids. Examples of the other culture medium components include those mentioned above.

The culture can be performed, for example, under aerobic conditions using a liquid medium. The term "aerobic conditions" refers to when the dissolved oxygen concentration in the culture medium is 0.33 ppm or higher (0.33 ppm is the detection limit of enzyme membrane electrodes), ans also when the dissolved oxygen concentration in the culture medium is 1.5 ppm or higher. The oxygen concentration may be controlled to be, for example, 5 to 50%, or about 10%, of the saturated oxygen concentration. The culture under aerobic conditions can be performed, specifically, as a culture with aeration, shaking, stirring, or a combination thereof. The pH of the culture medium may be, for example, 3 to 10, or 5 to 8. The pH of the culture medium can be adjusted during the culture as required. The pH of the culture medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, calcium hydroxide, and magnesium hydroxide. The culture temperature may be, for example, 20 to 40° C., or 25 to 37° C. The culture period may be, for example, 10 to 120 hours. The culture can be performed as batch culture, fed-batch culture, and/or continuous culture. The culture may be continued, for example, until the carbon source present in the culture medium is consumed, or until the activity of the host is lost.

By culturing the host having the disaccharide synthesizing enzyme gene in a culture medium under such conditions as mentioned above, the disaccharide synthesizing enzyme is expressed and a culture broth containing the disaccharide synthesizing enzyme is obtained. The disaccharide synthesizing enzyme can be accumulated in, for example, microbial cells of the host. The term "microbial cell" may be appropriately read as "cell" depending on the type of the host. Depending on the chosen host and design of the disaccharide synthesizing enzyme gene, it is also possible to accumulate the disaccharide synthesizing enzyme in the periplasm, or to produce the disaccharide synthesizing enzyme outside cells, e.g. on a cell surface layer or in a culture medium, by secretory production.

The disaccharide synthesizing enzyme can be used in any form usable for production of the disaccharide. The disaccharide synthesizing enzyme can be used, specifically, in any form that can act on the saccharide raw material. The disaccharide synthesizing enzyme can be used, for example, in a form of being isolated to a desired extent or in a form of being contained in a material. In other words, the phrase "disaccharide synthesizing enzyme" may refer to a disaccharide synthesizing enzyme purified to a desired extent (purified enzyme) or may refer to a material containing a disaccharide synthesizing enzyme.

The material containing the disaccharide synthesizing enzyme is not particularly limited, so long as it contains the disaccharide synthesizing enzyme to that the disaccharide synthesizing enzyme can act on the saccharide raw material. Examples of the material containing the disaccharide synthesizing enzyme include a culture broth, a culture supernatant, microbial cells, and a processed product of microbial cells, such as a disruption product, a lysate, and an extract (cell-free extract), containing the disaccharide synthesizing enzyme. Particular examples of the material containing the disaccharide synthesizing enzyme include microbial cells containing the disaccharide synthesizing enzyme. More particular examples of the material containing the disaccharide synthesizing enzyme include *E. coli* cells containing the disaccharide synthesizing enzyme. The microbial cells can be used for production of the disaccharide, for example, as they are, that is in a state that it is still contained in the culture broth, or after being collected from the culture broth. The microbial cells can be collected from the culture broth by centrifugation or the like. Also, the culture broth or the microbial cells collected therefrom can be used for production of the disaccharide, for example, after being subject to a treatment such as washing, concentration, and dilution as required. As described above, the microbial cells may be used, for example, in a form of being isolated to a desired extent or in a form of being contained in a material. The microbial cells may also be used, for example, in a form of immobilized cells immobilized on a carrier such as acrylamide and carrageenan. Furthermore, the disaccharide synthesizing enzyme may be used, for example, in a form of being separated and purified to a desired extent. The descriptions concerning separation and purification of the objective protein can be applied similarly to separation and purification of the disaccharide synthesizing enzyme. The disaccharide synthesizing enzyme may be used in a form of a free enzyme, or may be used in a form of an immobilized enzyme immobilized on a solid phase such as a resin.

The disaccharide synthesizing enzyme in such a form as mentioned above may be used in a single kind of form, or in a combination of two or more kinds of forms.

<2-2> Method for Producing Disaccharide

A disaccharide can be produced by carrying out a conversion reaction using the disaccharide synthesizing enzyme.

The conversion reaction can be carried out in an appropriate liquid. The liquid in which the conversion reaction is carried out is also referred to as a "reaction mixture". Specifically, the conversion reaction can be carried out by allowing the disaccharide synthesizing enzyme, e.g. one in the form exemplified above such as *E. coli* cells containing the disaccharide synthesizing enzyme, and the saccharide raw material to coexist in an appropriate reaction mixture. The conversion reaction, for example, may be carried out by a batch method or may be carried out by a column method. In the case of the batch method, the conversion reaction can be carried out by, for example, mixing the disaccharide synthesizing enzyme and the saccharide raw material in a reaction mixture contained in a reaction vessel. The conversion reaction may be carried out statically, or may be carried out with stirring or shaking the reaction mixture. In the case of the column method, the conversion reaction can be carried out by, for example, passing a reaction mixture containing the saccharide raw material through a column filled with an immobilized enzyme or immobilized cells. Examples of the reaction mixture can include those based on an aqueous medium (aqueous solvent) such as water and aqueous buffer.

The reaction mixture may contain components other than the saccharide raw material as required, in addition to the saccharide raw material. Examples of the components other than the saccharide raw material include pH buffers and culture medium components. The types and concentrations of the components contained in the reaction mixture may be determined according to various conditions such as the type and the use mode of the disaccharide synthesizing enzyme.

Conditions of the conversion reaction, such as pH of the reaction mixture, reaction temperature, reaction time, concentrations of various components, etc., are not particularly limited so long as the disaccharide is generated. The conversion reaction can be performed with, for example, conditions typically used for substance conversion using an enzyme or microbial cells. The conditions of the conversion reaction may be determined according to various conditions such as the type and the use mode of the disaccharide synthesizing enzyme. The pH of the reaction mixture may be, for example, usually 6.0 to 10.0, or 6.5 to 9.0. The reaction temperature may be, for example, usually 15 to 50° C., 15 to 45° C., or 20 to 40° C. The reaction time may be, for example, 5 minutes to 200 hours. In the case of the column method, the loading rate of the reaction mixture may be, for example, such a rate that the reaction time falls within the range of the reaction time exemplified above. Furthermore, the conversion reaction can also be performed with, for example, conditions typically used for culture of microorganisms such as bacteria. In the conversion reaction, cells may or may not proliferate. That is, the descriptions concerning the culture conditions for the host having the disaccharide synthesizing enzyme gene may also be applied similarly to the conditions of the conversion reaction, except that cells may or may not proliferate in the conversion reaction. In such a case, the culture conditions for obtaining the cells and the conditions of the conversion reaction may be the same or different. In addition, in cases of using the disaccharide synthesizing enzyme in a form of cells, the cells may lyse during the conversion reaction. The concentration of the saccharide raw material in the reaction mixture, for example, may be 1 g/L or higher, 10 g/L or higher, 50 g/L or higher, 100 g/L or higher, 200 g/L or higher, 300 g/L or higher, or 500 g/L or higher, or may be the saturated concentration or lower, 800 g/L or lower, 700 g/L or lower, 600 g/L or lower, or 500 g/L or lower, or may be within a range defined by a non-contradictory combination thereof. In cases of using a combination of glucose and other saccharide raw material(s) as the saccharide raw material, the ratio of the amount of glucose to the total amount of the saccharide raw material, for example, may be 1% w/w or higher, 10% w/w or higher, 30% w/w or higher, 50% w/w or higher, 70% w/w or higher, or 90% w/w or higher, or may be 99% w/w or lower, 90% w/w or lower, 70% w/w or lower, 50% w/w or lower, 30% w/w or lower, or 10% w/w or lower, or may be within a range defined by a non-contradictory combination thereof. The concentration of the disaccharide synthesizing enzyme in cases of using the disaccharide synthesizing enzyme in a form of cells, for example, may be 1 or higher, or may be 300 or lower, or may be within a range defined by a combination thereof, in terms of the OD600 nm.

During the conversion reaction, the disaccharide synthesizing enzyme, the saccharide raw material, and the other components may be additionally supplied to the reaction mixture independently or in any combination thereof. For example, the saccharide raw material may be additionally supplied to the reaction mixture in proportion to decrease or depletion of the saccharide raw material accompanying generation of the disaccharide. These components may be supplied once or a plurality of times, or may be continuously supplied.

Furthermore, the reaction conditions may be constant from the start to the end of the conversion reaction, or they may change during the conversion reaction. The expression "the reaction conditions change during the conversion reaction" includes not only when the reaction conditions temporally change, but also includes when the reaction conditions spatially change. The expression "the reaction conditions spatially change" can mean that, for example, when the conversion reaction is performed by the column method, the reaction conditions such as the reaction temperature and the packing density of the disaccharide synthesizing enzyme differ depending on position in the flow.

A reaction mixture containing the disaccharide is obtained by carrying out the conversion reaction using the disaccharide synthesizing enzyme as described above.

Production of the disaccharide can be confirmed by known methods used for detection or identification of compounds. Examples of such methods include, for example, HPLC, UPLC, LC/MS, GC/MS, and NMR. These methods can be independently used, or can be used in an appropriate combination.

The reaction mixture containing the disaccharide can be used as it is, or after being subjected to a treatment such as concentration and dilution as required.

Furthermore, the disaccharide generated can be collected as required. That is, the method for producing the disaccharide may include collecting the disaccharide protein generated from the reaction mixture. The disaccharide generated can be collected from the fermentation broth by known methods used for separation and purification of compounds. Examples of such methods include, for example, ion-exchange resin method, precipitation method, membrane treatment method, and crystallization method. These methods can be used alone or in any appropriate combination. Purification of the disaccharide can be carried out to a desired extent. When the disaccharide is precipitated in the reaction mixture, it can be collected by centrifugation, filtration, or the like. The disaccharide precipitated in the reaction mixture may also be isolated together with the disaccharide dissolving in the reaction mixture, after the disaccharide dissolving in the reaction mixture is crystallized.

The disaccharide collected may contain such components as the disaccharide synthesizing enzyme, the saccharide raw material, the reaction mixture components, and moisture in addition to the disaccharide. The purity of the disaccharide collected may be, for example, 30% (w/w) or higher, 50% (w/w) or higher, 70% (w/w) or higher, 80% (w/w) or higher, 90% (w/w) or higher, or 95% (w/w) or higher.

The disaccharide may also be used after being subject to a treatment such as sterilization. Sterilization can be carried out by, for example, heating or filter sterilization.

The use purpose of the disaccharide generated is not particularly limited. The disaccharide can be used for, for example, induction of cellulase production by cellulase-producing microorganisms such *Talaromyces cellulolyticus*. The disaccharide can also be used for, for example, the method for producing the objective protein.

EXAMPLES

Hereinafter, the present invention will be more specifically explained with reference to the following examples. However, the scope is not limited by these examples.

(1) Identification of the gh1-2 gene essential for cellulase production of T *cellulolyticus*

A gene is described that encodes a protein presumed to be a beta-glucosidase of the glucoside hydrolase family 1 (GH1), as a gene deeply involved in cellulase production for T *cellulolyticus*. Hereinafter, this is also referred to as "gh1-2". Also, the protein encoded by the gh1-2 gene is also referred to as "GH1-2".

(1-1) Construction of *T. Cellulolyticus* Strains F09ΔGh1-2 and F09pyrF+

The strain F09Δgh1-2 was constructed from the parent strain *T. cellulolyticus* strain F09 (Japanese Patent Laid-open (Kokai) No. 2016-131533) by disruption of the gh1-2 gene (SEQ ID NO: 1) according to the following procedure. The strain F09 has a mutation (single nucleotide substitution) in a pyrF gene obtained from the parent strain *T. cellulolyticus* strain S6-25 (NITE BP-01685). The strain F09 shows uracil auxotrophy due to the mutation in the pyrF gene.

First, a DNA fragment for gh1-2 disruption having a nucleotide sequence consisting of an upstream region of the gh1-2 gene, a pyrF gene marker, and a downstream region of the gh1-2 gene of *T. cellulolyticus* ligated in this order was prepared according to the following procedure.

PCR was performed by using the genomic DNA of the *T. cellulolyticus* strain Y-94 (FERM BP-5826) as the template in combination with primers of SEQ ID NOS: 2 and 3, to amplify the upstream region of the gh1-2 gene, or in combination with primers of SEQ ID NOS: 4 and 5, to amplify the downstream region of the gh1-2 gene. Separately, PCR was performed by using the genomic DNA of the *T. cellulolyticus* strain Y-94 (FERM BP-5826) as the template and primers of SEQ ID NOS: 6 and 7, to amplify a whole region (including promoter and terminator) of the pyrF gene. The PCR products were each purified by using Wizard SV Gel and PCR Clean-Up System (Promega). In-Fusion HD Cloning Kit (Takara Bio) was used to incorporate the purified PCR products into a pUC plasmid included in the kit and to thereby ligate them. *E. coli* JM109 was transformed with the reaction product, and cultured on LB agar medium containing 100 mg/L ampicillin at 37° C. overnight, to form colonies. A plasmid pUC-gh1-2::pyrF, into which the DNA fragment for gh1-2 disruption has been incorporated, was obtained from an obtained transformant by using Wizard Plus Miniprep System (Promega). PCR was performed by using the plasmid pUC-gh1-2::pyrF as the template and primers of SEQ ID NOS: 2 and 5, to amplify the DNA fragment for gh1-2 disruption, and the fragment was concentrated and purified by ethanol precipitation.

Then, the strain F09 was inoculated into a culture medium containing 12 g/L Potato Dextrose Broth (Difco) and 20 g/L Bacto Agar (Difco) (hereinafter, also referred to as "PD medium"), and cultured at 30° C. One agar disk excised from around the edge of a formed colony was inoculated into a culture medium containing 24 g/L Potato Dextrose Broth, and gyratory culture (220 rpm) was carried out at 30° C. for 2 days. To cells collected by centrifugation (5000 rpm for 5 minutes), 30 mL of a solution containing 10 g/L Yatalase (Takara Bio), 10 mM $KH_2PO_4$, and 0.8 M NaCl (pH6.0) were added. Reaction was carried out at 30° C. for 2 hours with shaking, to digest cell walls and prepare protoplasts. After residues were removed by using a glass filter, protoplasts were collected by centrifugation (2000 rpm for 10 minutes), and suspended with Tris-HCl buffer (pH7.5) containing 1.2 M Sorbitol and 10 mM $CaCl_2$, to prepare 1 mL of a protoplast solution. To a 200-4, aliquot of the protoplast solution, 10 μg of the purified DNA fragment for gh1-2 disruption, and 50 μL of Tris-HCl buffer (pH7.5) containing 400 g/L PEG4000 and 10 mM $CaCl_2$ were added, and left on ice for 30 minutes. Then, 1 mL of Tris-HCl buffer (pH7.5) containing 400 g/L PEG4000 and 10 mM $CaCl_2$) was further added to the mixture, and left at room temperature for 15 minutes to allow for transformation. Protoplasts were collected by centrifugation (2000 rpm for 10 minutes), inoculated into a minimal medium (Table 1) containing 1 M sucrose, and cultured at 30° C. for 7 days, to select strains of which the uracil auxotrophy was complemented. A colony that appeared was inoculated into a minimal medium and cultured at 30° C. for 4 days, and then replacement of the gh1-2 gene with the pyrF gene was confirmed, to obtain the strain F09Δgh1-2.

TABLE 1

| Composition of minimal medium | |
|---|---|
| 10 g/L | Glucose |
| 10 mM | $NH_4Cl$ |
| 10 mM | $KH_2PO_4$ |
| 7 mM | KCl |
| 2 mM | $MgSO_4$ |
| 0.06 mg/L | $H_3BO_3$ |
| 0.26 mg/L | $(NH_4)_6Mo_7O_{24}$—$4H_2O$ |
| 1 mg/L | $FeCl_3$—$6H_2O$ |
| 0.4 mg/L | $CuSO_4$—$5H_2O$ |
| 0.08 mg/L | $MnCl_2$ |
| 2 mg/L | $ZnCl_2$ |
| 20 g/L | Bacto Agar(Difco) |

In addition, as a control strain, the strain F09pyr+, in which the uracil auxotrophy has been complemented, was constructed by complementing the pyrF gene to the strain F09 according to the following procedure.

PCR was performed by using the genomic DNA of the *T. cellulolyticus* strain Y-94 (FERM BP-5826) as the template and primers of SEQ ID NOS: 8 and 9, to amplify a whole region (including promoter and terminator) of the pyrF gene. The PCR product was purified by using Wizard SV Gel and PCR Clean-Up System (Promega). In-Fusion HD Cloning Kit (Takara Bio) was used to incorporate the purified PCR products into a pUC plasmid included in the kit and to thereby ligate them. *E. coli* JM109 was transformed with the reaction product, and cultured on LB agar medium containing 100 mg/L ampicillin at 37° C. overnight, to form colonies. A plasmid pUC-pyrF, into which the whole region (including promoter and terminator) of the pyrF gene has been incorporated, was obtained from an obtained transformant by using Wizard Plus Miniprep System (Promega). PCR was performed by using the plasmid pUC-pyrF as the template and primers of SEQ ID NOS: 7 and 8, to amplify the DNA fragment for complementation of the pyrF gene, and the fragment was concentrated and purified by ethanol precipitation.

Then, the strain F09 was inoculated into PD medium, and cultured at 30° C. One agar disk excised from around the edge of a formed colony was inoculated into a culture medium containing 24 g/L Potato Dextrose Broth, and gyratory culture (220 rpm) was carried out at 30° C. for 2 days. To cells collected by centrifugation (5000 rpm for 5 minutes), 30 mL of a solution containing 10 g/L Yatalase (Takara Bio), 10 mM $KH_2PO_4$, and 0.8 M NaCl (pH6.0) were added. Reaction was carried out at 30° C. for 2 hours with shaking, to digest cell walls and prepare protoplasts. After residues were removed by using a glass filter, protoplasts were collected by centrifugation (2000 rpm for 10 minutes), and suspended with Tris-HCl buffer (pH7.5) containing 1.2 M Sorbitol and 10 mM $CaCl_2$), to prepare 1 mL of a protoplast solution. To a 200-μL aliquot of the protoplast solution, 10 μg of the purified DNA fragment for complementation of the pyrF gene, and 50 μL of Tris-HCl buffer (pH7.5) containing 400 g/L PEG4000 and 10 mM $CaCl_2$ were added, and left on ice for 30 minutes. Then, 1 mL of Tris-HCl buffer (pH7.5) containing 400 g/L PEG4000 and 10 mM $CaCl_2$ was further added to the mixture, and left at a room temperature for 15 minutes to allow for transformation. Protoplasts were collected by centrifugation (2000 rpm for 10 minutes), inoculated into a minimal medium containing 1 M sucrose, and cultured at 30° C. for 7 days, to select strains in which the uracil auxotrophy was complemented. A colony that appeared was inoculated into a minimal medium and cultured at 30° C. for 4 days, and then replacement of the mutant pyrF gene with the wild-type pyrF gene was confirmed, to obtain the strain F09pyr+.

(1-2) Preparation of Supernatant Samples of Flask Culture Using Cellulose as Carbon Source Cellulase production by the *T. cellulolyticus* strains F09Δgh1-2 and F09pyr+ was evaluated by flask culture using Solka-Floc (International Fiber Corporation), which is a cellulosic substrate, as a carbon source.

<Flask Culture>

The strains F09Δgh1-2 and F09pyr+ were each inoculated into a 1/2 PDA plate (Table 2), and cultured at 30° C. for 3 days. One agar disk excised from around the edge of a formed colony formed was inoculated into SF flask medium (Table 2), and a gyratory culture (220 rpm) was carried out at 30° C. for 7 days. Sampling was appropriately carried out, cells were removed using a 0.22 μm syringe filter, and the obtained culture supernatant was used as an enzyme solution.

TABLE 2

| <Composition of SF flask medium> | |
|---|---|
| 40 g/L | Solka-Floc |
| 1.2 g/L | $MgSO_4$—$7H_2O$ |
| 24 g/L | $KH_2PO_4$ |
| 5 g/L | $(NH_4)_2SO_4$ |
| 1 ml/L | Tween80 |
| 0.01 g/L | $ZnSO_4$—$7H_2O$ |
| 0.01 g/L | $MnSO_4$—$5H_2O$ |
| 0.01 g/L | $CuSO_4$—$5H_2O$ |
| 4 g/L | Urea |
| 4.7 g/L | $C_4H_4K_2O_6$—½$H_2O$ |
| <Composition of ½PDA plate> | |
| 12 g/L | Potato Dextrose Broth(Difco) |
| 20 g/L | Bacto Agar(Difco) |

※pH 4.0($H_2SO_4$)

(1-3) Electrophoresis of Supernatant Samples of Flask Culture

The sample solutions were subject to SDS-PAGE and CBB staining. Specifically, the sample solutions were subject to electrophoresis using Any kD™ Mini-PROTEAN (Registered trademark) TGX™ Precast Protein Gels (BIO-RAD) and PowerPac™ Basic Power Supply(BIO-RAD), and then stained with Bio-Safe™ Coomassie Stain (BIO-RAD).

Results are shown in FIG. 1. Secretion of proteins presumed to be cellulases was observed for the control strain F09pyr+, whereas secretion of proteins was scarcely observed for the strain F09Δgh1-2 (the left panel of FIG. 1). In addition, when the culture broths were left to stand for 24 hours and then subject to observation, precipitation of Solka-Floc, which was a solid content added as a substrate, was observed for the strain F09Δgh1-2 as opposed to the strain F09pyr+(the right panel of FIG. 1). From these results, it was shown that the ability for secretory production and assimilation of cellulase were significantly decreased in the strain F09Δgh1-2 as compared with the strain F09pyr+.

(1-4) Growth of *T. cellulolyticus* Strain F09ΔGh1-2 on Various Carbon Sources and Halo Assay for Secretory Cellulase Since it was shown that the ability for secretory production and assimilation of cellulase were significantly decreased in the strain F09Δgh1-2, growth and secretory production of cellulase when using various carbon sources were evaluated. The procedure is shown below.

The strains F09Δgh1-2 and F09pyr+ were each inoculated into the minimal medium, and cultured at 30° C. for 3 days. One agar disk excised from around the edge of a formed colony formed was left to stand on each of the minimal media and PD media containing various carbon sources, culture was carried out at 30° C., and observation of growth was carried out. The various carbon sources consist of 10 g/L of glucose, cellobiose, Solka-Floc (International Fiber Corporation), and Sodium carboxymethyl cellulose (average Mw approximately 250,000, SIGMA, hereinafter, also referred to as "CMC").

Results are shown in FIG. 2. No difference of growth was observed between the strains F09pyr+ and F09Δgh1-2 for the minimal medium and PD medium containing glucose as the carbon source. By contrast, a decrease in colony growth and a change of the density of mycelia were observed for the strain F09Δgh1-2 as compared with the strain F09pyr+ for the minimal medium and PD medium containing the cellulosic substrate, i.e. cellobiose, Solka-Floc, or CMC, as the carbon source.

In addition, agar media containing CMC can be used for halo assay for evaluating secretory cellulase on the basis of a phenomenon that CMC partially degraded by cellulase is hardly stained with Congo-red. The strains F09Δgh1-2 and F09pyr+ were each grown on the minimal medium containing CMC as the carbon source according to a similar procedure to the aforementioned experiment. After the culture, a Congo Red solution obtained by mixing 50 mM sodium phosphate buffer (pH 7.0) and 2 mg/ml Congo Red (Nacalai Tesque) in a volume ratio of 10:1 was added to the plate so that the Congo Red solution covered the whole of the plate, and the plate was left to stand for 30 minutes at a room temperature. Then, the Congo Red solution on the plate was removed, and sodium phosphate buffer (50 mM, pH 7.0) was added to the plate so that the sodium phosphate buffer covered the whole of the plate. The plate was again left to stand for 30 minutes at a room temperature. Then, the sodium phosphate buffer on the plate was removed, the surface of the plate was dried lightly, and observation of halo was carried out.

Results are shown in FIG. 2. Halo was observed outside the colony for the strain F09pyr+, whereas halo was not observed outside the colony for the strain F09Δgh1-2.

From these results, it was shown that the protein (GH1-2) presumed to be a GH1-type beta-glucosidase and encoded by the gh1-2 gene is important for secretory production of cellulase and assimilation of cellulose.

(2) Expression and Functional Analysis of Protein Encoded by Gh1-2 Gene (2-1) Obtaining cDNA of Gh1-2 Gene and Expression Thereof in *E. coli*

An RNA solution was prepared from cells of the *T. cellulolyticus* strain Y-94 by using RNeasy Plant Mini Kit (QIAGEN), and a full-length cDNA solution was prepared form the RNA solution by using SMARTer (Registered trademark) RACE 5'/3' kit.

This cDNA solution and primers of SEQ ID NOS: 10 and 11 for 5'/3'RACE analysis designed in the internal region of the gh1-2 gene were used, to analyze the 5' and 3' termini of transcription products according to the manual of the kit. As a result, transcription start sites of the gh1-2 gene were concentrated in the region of 90 to 60 bases upstream of the start codon, and transcription termination sites were scattered in the region of 60 to 180 bases downstream of the stop codon. The start codon and the stop codon used herein are the start codon and the stop codon of cDNA sequence of SEQ ID NO: 22 described below. In the full-length cDNA of the gh1-2 gene, no proper candidates of the start codon and the stop codon were found outside the cDNA sequence of SEQ ID NO: 22.

Then, PCR was performed by using the cDNA solution as the template and primers of SEQ ID NOS: 12 and 13, to amplify a cDNA fragment of the gh1-2 gene. Separately, PCR was performed by using a plasmid pET24a (Novagen) as the template and primers of SEQ ID NOS: 14 and 15, to amplify pET24a. The PCR products were each purified by using Wizard SV Gel and PCR Clean-Up System (Promega). In-Fusion HD Cloning Kit (Takara Bio) was used to ligate the purified PCR products. *E. coli* JM109 was transformed with the reaction product, and cultured on LB agar medium containing 50 mg/L kanamycin at 37° C. overnight, to form colonies. A plasmid pET24a-gh1-2-His6, into which the cDNA fragment of the gh1-2 gene has been incorporated, was obtained from an obtained transformant by using Wizard Plus Miniprep System (Promega). When using the plasmid pET24a-gh1-2-His6, GH1-2 is expressed in a form having a His-tag at the C-terminus. Sequencing analysis of the plasmid pET24a-gh1-2-His6 was carried out by using primer of SEQ ID NOS: 16, 17, 18, 19, 20, and 21, to thereby determine the cDNA sequence of the gh1-2 gene (the cDNA sequence of the coding region of the gh1-2 gene; SEQ ID NO: 22) and the amino acid sequence of GH1-2 encoded thereby (SEQ ID NO: 23). This amino acid sequence does not contain any secretion signal sequence, and hence, it is suggested that GH1-2 is a protein localized in cells.

*E. coli* Rosetta™ 2(DE3)pLysS Competent Cells (Novagen) were transformed with the plasmid pET24a-gh1-2-His6, and cultured on LB agar medium containing 50 mg/L kanamycin at 37° C. overnight, to form colonies. The formed colonies were streaked on LB agar medium containing 50 mg/L kanamycin, and single colonies were obtained, to thereby obtain a strain EcGHH6.

The *E. coli* strain EcGHH6 was inoculated into 3 mL of LB medium containing 50 mg/L kanamycin in a test tube, and cultured with shaking (120 rpm) at 37° C. overnight. The culture broth was inoculated into 50 mL of LB medium containing 50 mg/L kanamycin in a shaking flask in a volume of 1/100, and cultured with shaking (120 rpm) at 37° C. until OD600 reached 0.8. Then, the shaking flask was moved into a box shaker (13° C.), and culture was carried out with shaking (120 rpm) at 13° C. for 1 hour. Then, IPTG was added at a concentration of 1 mM, and culture was further continued for 17 hours. After the culture, cells were collected by centrifugation (4° C., 5000 rpm, 5 min), and frozen for 1 hour in a freezer (−20° C.). Then, soluble proteins were extracted from the cells by using Ni-NTA Fast Start Kit (QIAGEN) under non-denaturing conditions, and GH1-2 having an added His-tag at the C-terminus was purified by using a Ni-NTA affinity column, a wash buffer, and an elution buffer included in the kit. A fraction containing the purified GH1-2 was desalinated and concentrated by using Amicon Ultra-15 30 kDa cut off (Merck Millipore) ultrafiltration membrane filter and 50 mM sodium phosphate buffer (pH 6.5). Then, SDS-PAGE and Western analysis using Pierce Fast Western Blot Kit (Thermo Fisher Scientific) and a His-tag antibody Anti-His-tag mAb-HRP-DirecT (MLB) were carried out. The purified GH1-2 was confirmed to provide a single band (FIG. 3), and used for the following experiment.

(2-2) Identification of Reaction Product Form High-Concentration Glucose by GH1-2

The purified GH1-2 was added to a 40% glucose aqueous solution at a concentration of 1.4 g/L, and reaction was carried out at 40° C. for 24 hours, to thereby obtain a sample. This sample was diluted 1000-fold with ion-exchanged water, and subjected to ion-exchange chromatography, to thereby analyze the reaction product. The conditions of the ion exchange chromatography are shown in Table 3. As a result, generation of beta-linked glucose oligosaccharides such as gentiobiose by GH1-2 was confirmed (FIG. 4).

TABLE 3

| | |
|---|---|
| Analysis column | Dionex ISC-3000 |
| Column | Carbo Pac PA1 Analytical (2.0 mm × 250 mm) |
| Guard column | Carbo Pac PA1 Guerd (2.0 mm × 50 mm) |
| Mobile phase | A $H_2O$<br>B 0.1M NaOH<br>C 0.5M $CH_3COONa$/0.1M NaOH |
| Gradient pattern | As described below |
| Column temperature | 30° C. |
| Flow rate | 0.25 ml/min |
| Detector | Electrochemical detection (PAD) |
| Injection volume | 5.0 μl |

TABLE 3-continued

| Gradient pattern of mobile phase | | | |
|---|---|---|---|
| Time (min) | A(%) | B (%) | C (%) |
| −30 | 0 | 100 | 0 |
| −20 | 0 | 100 | 0 |
| 0 | 90 | 10 | 0 |
| 25 | 90 | 10 | 0 |
| 40 | 36 | 64 | 0 |
| 50 | 0 | 88 | 12 |
| 70 | 0 | 64 | 36 |
| 71 | 0 | 0 | 100 |
| 80 | 0 | 0 | 100 |

Thus, it was shown that beta-linked glucose oligosaccharides such as gentiobiose can be generated from high-concentration glucose by using GH1-2. That is, it was shown that GH1-2 has a transglycosylation activity.

(3) Evaluation of Cellulase Production-Inducing Ability of Beta-Linked Glucose Oligosaccharides in *T. cellulolyticus*

(3-1) Halo assay for secretory cellulase by various beta-linked glucose oligosaccharides The cellulase production-inducing ability of beta-linked glucose oligosaccharides generated by GH1-2 in *T. cellulolyticus* was validated. The procedure is shown below.

Minimal media containing CMC as the carbon source (CMC minimal media) and having various added beta-linked glucose oligosaccharides (cellotriose, cellobiose, gentiobiose, laminaribiose, and sophorose) at a concentration of 1 mM were prepared. The strains F09pyr+ and F09Δgh1-2 were each grown on the minimal medium containing glucose as the carbon source for 3 days. One agar disk excised from around the edge of a formed colony formed was left to stand on each of the CMC minimal media containing the various beta-linked glucose oligosaccharides, and grown at 30° C. for 36 hours. After the culture, a Congo Red solution obtained by mixing 50 mM sodium phosphate buffer (pH 7.0) and 2 mg/ml Congo Red (Nacalai Tesque) in a volume ratio of 10:1 was added to the plate so that the Congo Red solution covered the entire plate, and the plate was left to stand for 30 minutes at a room temperature. Then, the Congo Red solution on the plate was removed, and sodium phosphate buffer (50 mM, pH 7.0) was added to the plate so that the sodium phosphate buffer covered the entire plate. The plate was again left to stand for 30 minutes at a room temperature. Then, the sodium phosphate buffer on the plate was removed, the surface of the plate was dried lightly, and observation of halo was carried out.

Results are shown in FIG. 5. It was shown that gentiobiose strongly complements the decrease in the ability for secretory production of cellulase in *T. cellulolyticus* due to deletion of the gh1-2 gene. In particular, gentiobiose complemented the decrease in the ability for secretory production of cellulase more strongly than other beta-linked glucose oligosaccharides even when gentiobiose was used at a concentration of 0.01 mM, which is 1/100concentration. By contrast, it was shown that cellobiose, which has been generally known as an inducer of cellulase secretion, is scarcely able to complement the decrease in the ability for secretory production of cellulase. From these results, it was revealed that gentiobiose shows a strong cellulase production-inducing ability in *T. cellulolyticus.*

(3-2) Identification of reaction product form cellobiose by GH1-2

Considering the fact that cellobiose was scarcely able to complement the significant decrease in the ability for secretory production of cellulase due to deletion of the gh1-2 gene, the possibility that GH1-2, presumed to be a beta-glucosidase, acts on cellobiose to thereby be involved in cellulase secretion was investigated.

The purified GH1-2 was added to a 2% cellobiose aqueous solution at a concentration of 30 μg/mL, and a reaction solution after reaction at 40° C. for 1 to 60 minutes was used as a sample solution. The sample solution in 3 μL portions was spotted and developed on a thin layer chromatography plate (Merck) having a silica layer having a thickness of 200 μm, a size of 20×20 cm, and an average pore diameter of 60 angstroms. The composition of the developing solvent was chloroform:methanol:pure water=30:20:5 by volume ratio. An aniline phthalate method for detecting a reducing group was used for color development detection. After fully evaporating the developing solvent after development, a color developing solution obtained by dissolving phthalic acid and aniline in water-saturated butanol was sprayed with a glass spray, and the thin layer chromatography plate was heated using a hot plate at 150° C. or higher until sufficient color development was obtained. As a result, it was confirmed that the reaction product of cellobiose and GH1-2 contained not only glucose, which is a product of hydrolyzation, but also contained cellotriose, gentiobiose, sophorose, and laminaribiose, which are beta-linked glucose oligosaccharides (FIG. 6). Thus, it was shown again that GH1-2 has not only a hydrolysis activity but also has a transglycosylation activity.

In addition, the sample solution was diluted 10-fold with ion-exchanged water, and subjected to ion-exchange chromatography under the conditions described in Example (2-2), to thereby analyze the reaction product. As a result, the generation of beta-linked glucose oligosaccharides including gentiobiose by GH1-2 (FIG. 7) was confirmed.

From these results, it was suggested that GH1-2 of *T. cellulolyticus* is able to generate beta-linked glucose oligosaccharides including gentiobiose from cellobiose by transglycosylation in cells.

(4) Evaluation of cellulase production culture using gentiobiose

Liquid culture of *T. cellulolyticus* was carried out by adding gentiobiose, and the effect thereof on cellulase production was validated. The procedure is shown below.

(4-1) Construction of *T. cellulolyticus* strain F09ΔsC

The strain F09ΔsC was constructed from the parent strain *T. cellulolyticus* strain F09 (Japanese Patent Laid-open (Kokai) No. 2016-131533) by disruption of the sC gene according to the following procedure. The sC gene encodes a sulfate permease of the sulfate assimilation pathway. Deletion of the sC gene results in methionine auxotrophy but provides selenate tolerance.

First, a DNA fragment for sC disruption having a nucleotide sequence consisting of an upstream region of the sC gene, a pyrF gene marker, and a downstream region of the sC gene of *T. cellulolyticus* ligated in this order was prepared according to the following procedure.

PCR was performed by using the genomic DNA of the *T. cellulolyticus* strain Y-94 (FERM BP-5826) as the template in combination with primers of SEQ ID NOS: 24 and 25, to amplify the upstream region of the sC gene, or in combination with primers of SEQ ID NOS: 26 and 27, to amplify the downstream region of the sC gene. The PCR products were each purified by using Wizard SV Gel and PCR Clean-Up System (Promega). In-Fusion HD Cloning Kit (Takara Bio) was used to incorporate the purified PCR products into a pUC plasmid included in the kit and to thereby ligate them. *E. coli* JM109 was transformed with the reaction product, and cultured on LB agar medium containing 100 mg/L ampicillin at 37° C. overnight, to form colonies. A plasmid pUC-dsC, into which the DNA fragment for sC disruption was incorporated, was obtained from an obtained transformant by using Wizard Plus Miniprep System (Promega). PCR was performed by using the plasmid pUC-dsC as the template and primers of SEQ ID NOS: 24 and 27, to amplify the DNA fragment for sC gene disruption, and the fragment was concentrated and purified by ethanol precipitation.

Then, the strain F09 was inoculated into PD medium, and cultured at 30° C. One agar disk excised from around the edge of a formed colony was inoculated into a culture medium containing 24 g/L Potato Dextrose Broth, and gyratory culture (220 rpm) was carried out at 30° C. for 2 days. To cells collected by centrifugation (5000 rpm for 5 minutes), 30 mL of a solution containing 10 g/L Yatalase (Takara Bio), 10 mM $KH_2PO_4$, and 0.8 M NaCl (pH6.0) was added. Reaction was carried out at 30° C. for 2 hours with shaking, to digest cell walls and prepare protoplasts. After residues were removed by using a glass filter, protoplasts were collected by centrifugation (2000 rpm for 10 minutes), and suspended with Tris-HCl buffer (pH7.5) containing 1.2 M Sorbitol and 10 mM $CaCl_2$), to prepare 1 mL of a protoplast solution. To a 200-μL aliquot of the protoplast solution, 10 μg of the purified DNA fragment for sC gene disruption, and 50 μL of Tris-HCl buffer (pH7.5) containing 400 g/L PEG4000 and 10 mM $CaCl_2$) was added, and left on ice for 30 minutes. Then, 1 mL of Tris-HCl buffer (pH7.5) containing 400 g/L PEG4000 and 10 mM $CaCl_2$) was further added to the mixture, and left at a room temperature for 15 minutes to allow for transformation. Protoplasts were collected by centrifugation (2000 rpm for 10 minutes), inoculated into a minimal medium containing 1 M sucrose, 1 mM selenate, 30 mg/L L-methionine, 1 g/L uridine, and 1 g/L uracil, and cultured at 30° C. for 14 days, to select strains tolerant to selenate. A colony that appeared was inoculated into a minimal medium containing 30 mg/L L-methionine, 1 g/L uridine, and 1 g/L uracil and cultured at 30° C. for 4 days, and then exhibition of the methionine auxotrophy and deletion of the sC gene were confirmed, to obtain the strain F09ΔsC.

(4-2) Construction of *T. cellulolyticus* strain F09Δgh1-2ΔsC

The strain F09Δgh1-2ΔsC was constructed from the parent strain T *cellulolyticus* strain F09ΔsC by disruption of the gh1-2 gene according to the following procedure.

PCR was performed by using the plasmid pUC-gh1-2::pyrF as the template and primers of SEQ ID NOS: 2 and 5, to amplify the DNA fragment for gh1-2 disruption, and the fragment was concentrated and purified by ethanol precipitation.

Then, the strain F09ΔsC was inoculated into PD medium, and cultured at 30° C. One agar disk excised from around the edge of a formed colony was inoculated into a culture medium containing 24 g/L Potato Dextrose Broth, and gyratory culture (220 rpm) was carried out at 30° C. for 2 days. To cells collected by centrifugation (5000 rpm for 5 minutes), 30 mL of a solution containing 10 g/L Yatalase (Takara Bio), 10 mM $KH_2PO_4$, and 0.8 M NaCl (pH6.0) were added. Reaction was carried out at 30° C. for 2 hours with shaking, to digest cell walls and prepare protoplasts. After residues were removed by using a glass filter, protoplasts were collected by centrifugation (2000 rpm for 10 minutes), and suspended with Tris-HCl buffer (pH7.5) containing 1.2 M Sorbitol and 10 mM $CaCl_2$), to prepare 1 mL of a protoplast solution. To a 200-μL aliquot of the protoplast solution, 10 μg of the purified DNA fragment for gh1-2 disruption, and 50 μL of Tris-HCl buffer (pH7.5) containing 400 g/L PEG4000 and 10 mM $CaCl_2$) were added, and left on ice for 30 minutes. Then, 1 mL of Tris-HCl buffer (pH7.5) containing 400 g/L PEG4000 and 10 mM $CaCl_2$) was further added to the mixture, and left at a room temperature for 15 minutes to allow for transformation. Protoplasts were collected by centrifugation (2000 rpm for 10 minutes), inoculated into a minimal medium containing 1 M sucrose and 30 mg/L L-methionine, and cultured at 30° C. for 7 days, to select strains in which the uracil auxotrophy was complemented. A colony that appeared was inoculated into a minimal medium containing 30 mg/L L-methionine and cultured at 30° C. for 4 days, and then exhibition of the methionine auxotrophy and replacement of the gh1-2 gene with the pyrF gene were confirmed, to obtain the strain F09Δgh1-2ΔsC.

(4-3) Construction of *T. cellulolyticus* strain F09Δgh1-2ΔpyrF

The strain F09Δgh1-2ΔpyrF was constructed from the parent strain T *cellulolyticus* strain F09Δgh1-2ΔsC by replacing the pyrF gene inserted in the gh1-2 gene region with the sC gene according to the following procedure.

PCR was performed by using the genomic DNA of the *T. cellulolyticus* strain Y-94 (FERM BP-5826) as the template in combination with primers of SEQ ID NOS: 2 and 28, to amplify the upstream region of the gh1-2 gene, or in combination with primers of SEQ ID NOS: 29 and 5, to amplify the downstream region of the gh1-2 gene. Separately, PCR was performed by using the genomic DNA of the *T. cellulolyticus* strain Y-94 (FERM BP-5826) as the template and primers of SEQ ID NOS: 30 and 31, to amplify a whole region (including promoter and terminator) of the sC gene. The PCR products were each purified by using Wizard SV Gel and PCR Clean-Up System (Promega). In-Fusion HD Cloning Kit (Takara Bio) was used to incorporate the purified PCR products into a pUC plasmid included in the kit and to thereby ligate them. *E. coli* JM109 was transformed with the reaction product, and cultured on LB agar medium containing 100 mg/L ampicillin at 37° C. overnight, to form colonies. A plasmid pUC-dgh-sC, into which the DNA fragment for pyrF disruption was incorporated, was obtained from an obtained transformant by using Wizard Plus Miniprep System (Promega). PCR was performed by using the plasmid pUC-dgh-sC as the template and primers of SEQ ID NOS: 2 and 5, to amplify the DNA fragment for pyrF disruption, and the fragment was concentrated and purified by ethanol precipitation.

Then, the strain F09Δgh1-2ΔsC was inoculated into a culture medium containing 12 g/L Potato Dextrose Broth (Difco) and 20 g/L Bacto Agar (Difco) (hereinafter, also referred to as "PD medium"), and cultured at 30° C. One agar disk excised from around the edge of a formed colony was inoculated into a culture medium containing 24 g/L Potato Dextrose Broth, and gyratory culture (220 rpm) was carried out at 30° C. for 2 days. To cells collected by centrifugation (5000 rpm for 5 minutes), 30 mL of a solution containing 10 g/L Yatalase (Takara Bio), 10 mM $KH_2PO_4$, and 0.8 M NaCl (pH6.0) were added. Reaction was carried out at 30° C. for 2 hours with shaking, to digest cell walls and prepare protoplasts. After residues were removed by using a glass filter, protoplasts were collected by centrifugation (2000 rpm for 10 minutes), and suspended with Tris-HCl buffer (pH7.5) containing 1.2 M Sorbitol and 10 mM $CaCl_2$), to prepare 1 mL of a protoplast solution. A 200-μL aliquot of the protoplast solution was mixed with 10 μg of the purified DNA fragment for pyrF disruption, and 50 μL of Tris-HCl buffer (pH7.5) containing 400 g/L PEG4000 and 10 mM $CaCl_2$), and left on ice for 30 minutes. Then, 1 mL of Tris-HCl buffer (pH7.5) containing 400 g/L PEG4000 and 10 mM $CaCl_2$) was further added to the mixture, and it was left at a room temperature for 15 minutes to allow for transformation. Protoplasts were collected by centrifugation (2000 rpm for 10 minutes), inoculated into a minimal medium containing 1 M sucrose, 1 g/L uridine, and 1 g/L uracil, and cultured at 30° C. for 7 days, to select strains of which the methionine auxotrophy was complemented. A colony that appeared was inoculated into a minimal medium containing 1 g/L uridine and 1 g/L uracil and cultured at 30° C. for 4 days, and then exhibition of the uracil auxotrophy in combination with complementation of the methionine auxotrophy and replacement of the pyrF gene inserted in the gh1-2 gene region with the sC gene was confirmed, to obtain the strain F09Δgh1-2ΔpyrF.

(4-4) Construction of *T. cellulolyticus* strains F09ΔcreA and F09Δgh1-2ΔcreA

The creA gene of the parent strains *T. cellulolyticus* strains F09 and F09Δgh1-2ΔpyrF was disrupted according to the following procedure, to construct the *T. cellulolyticus* stains F09ΔcreA and F09Δgh1-2ΔcreA.

The creA gene encodes a transcription factor involved in catabolite repression. The creA gene is known to be involved in the expression of cellulase (Mol Gen Genet. 1996 June 24; 251(4):451-60, Biosci Biotechnol Biochem. 1998 December; 62(12):2364-70) in filamentous fungi. By disruption of the creA gene, the cellulase-producing ability of *T. cellulolyticus* can be improved (WO2015/093467).

First, a DNA fragment for creA disruption having a nucleotide sequence consisting of an upstream region of the creA gene, a pyrF gene marker, and a downstream region of the creA gene of *T. cellulolyticus* ligated in this order was prepared according to the following procedure.

PCR was performed by using the genomic DNA of the *T. cellulolyticus* strain Y-94 (FERM BP-5826) as the template in combination with primers of SEQ ID NOS: 32 and 33, to amplify the upstream region of the creA gene, or in combination with primers of SEQ ID NOS: 34 and 35, to amplify the downstream region of the creA gene. Separately, PCR was performed by using the genomic DNA of the *T. cellulolyticus* strain Y-94 (FERM BP-5826) as the template and primers of SEQ ID NOS: 36 and 37, to amplify a whole region (including promoter and terminator) of the pyrF gene. The PCR products were each purified by using Wizard SV Gel and PCR Clean-Up System (Promega). In-Fusion HD Cloning Kit (Takara Bio) was used to incorporate the purified PCR products into a pUC plasmid included in the kit and to thereby ligate them. *E. coli* JM109 was transformed with the reaction product, and cultured on LB agar medium containing 100 mg/L ampicillin at 37° C. overnight, to form colonies. A plasmid pUC-creA::pyrF, into which the DNA fragment for creA disruption has been incorporated, was obtained from an obtained transformant by using Wizard Plus Miniprep System (Promega). PCR was performed by using the plasmid pUC-creA::pyrF as the template and primers of SEQ ID NOS: 32 and 35, to amplify the DNA fragment for creA disruption, and the fragment was concentrated and purified by ethanol precipitation.

Then, the strains F09 and F09Δgh1-2ΔpyrF were each inoculated into PD medium, and cultured at 30° C. One agar disk excised from around the edge of a formed colony was inoculated into a culture medium containing 24 g/L Potato Dextrose Broth, and gyratory culture (220 rpm) was carried out at 30° C. for 2 days. To the cells collected by centrifugation (5000 rpm for 5 minutes), 30 mL of a solution containing 10 g/L Yatalase (Takara Bio), 10 mM $KH_2PO_4$, and 0.8 M NaCl (pH6.0) were added. Reaction was carried out at 30° C. for 2 hours with shaking, to digest cell walls and prepare protoplasts. After residues were removed by using a glass filter, protoplasts were collected by centrifugation (2000 rpm for 10 minutes), and suspended with Tris-HCl buffer (pH7.5) containing 1.2 M Sorbitol and 10 mM $CaCl_2$), to prepare 1 mL of a protoplast solution. To a 200-μL aliquot of the protoplast solution, 10 μg of the purified DNA fragment for creA disruption, and 50 μL of Tris-HCl buffer (pH7.5) containing 400 g/L PEG4000 and 10 mM $CaCl_2$) were added, and left on ice for 30 minutes. Then, the mixture was further mixed with 1 mL of Tris-HCl buffer (pH7.5) containing 400 g/L PEG4000 and 10 mM $CaCl_2$), and left at a room temperature for 15 minutes to allow for transformation. Protoplasts were collected by centrifugation (2000 rpm for 10 minutes), inoculated into a minimal medium containing 1 M sucrose, and cultured at 30° C. for 7 days, to select strains of which the uracil auxotrophy was complemented. A colony that appeared was inoculated into a minimal medium and cultured at 30° C. for 4 days, and then replacement of the creA gene with the pyrF was confirmed, to obtain the strains F09ΔcreA and F09Δgh1-2ΔcreA.

(4-5) Preparation of saccharide solutions containing gentiobiose

Saccharide solutions containing gentiobiose were prepared by using the purified GH1-2 and *E. coli* cells expressing GH1-2. The procedure is shown below.

The purified GH1-2 obtained in Example (2-1) was added to a 560 g/L glucose solution at a concentration of 1.4 g/L, to thereby obtain a reaction mixture. The reaction mixture was stirred so as to be uniform, and then left to stand at a room temperature for 52 hours. Then, the reaction mixture was heated at 95° C. for 10 minutes, to thereby obtain a saccharide solution containing gentiobiose. It was confirmed by the ion-exchange chromatography mentioned above that the saccharide solution contains 35.04 g/L gentiobiose.

Separately, the *E. coli* strain EcGHH6 was inoculated into 3 mL of LB medium containing 50 mg/L kanamycin in a test tube, and cultured with shaking (120 rpm) at 37° C. overnight. Cells were inoculated into 50 mL of LB medium containing 50 mg/L kanamycin contained in a shaking flask in a volume of 1/100, and cultured with shaking (120 rpm) at 37° C. until OD600 reached 0.8. Then, the shaking flask was moved into a box shaker (13° C.), and culture was carried out with shaking (120 rpm) at 13° C. for 1 hour. Then, IPTG was added at a concentration of 1 mM, and culture was further continued for 17 hours. After the culture, cells were collected by centrifugation (5000 rpm, 5 min) at 4° C., and re-suspended in 5 mL of the culture supernatant. The cell suspension (5 mL) was put into 100 mL of a 700 g/L glucose solution, to thereby obtain a cell reaction mixture. Reaction was carried out at a room temperature for 144 hours while stirring the cell reaction mixture so as to be uniform, and sampling was carried out over time. During this process, cells lysed according to elapse of time, and thereby the cell reaction mixture changed to transparent (the left panel of FIG. 9). The sampled saccharide solution was heated at 95° C. for 10 minutes, diluted 1000-fold, and analyzed by the ion-exchange chromatography mentioned above. As a result, it was confirmed that gentiobiose was generated over time (FIG. 8). The saccharide solution after reaction for 144 hours was heated at 95° C. for 10 minutes, diluted with distilled water to provide a concentration corresponding to a 560 g/L glucose solution, to thereby obtain a saccharide solution containing gentiobiose.

Separately, a cell reaction mixture similarly prepared was evaluated in a similar manner when the cell reaction mixture was left to stand at a room temperature without stirring. As a result, also without stirring, cells lysed according to elapse of time, and thereby the cell reaction mixture changed to transparent (the left panel of FIG. 9).

Each cell reaction mixture filtered or not filtered with a 0.22 μm pore size filter was subject to SDS-PAGE, CBB staining using Bio-Safe™ Coomassie Stain (BIO-RAD), and stained with Bio-Safe™ Coomassie Stain (BIO-RAD), and Western analysis using Pierce Fast Western Blot Kit (Thermo Fisher Scientific) and a His-tag antibody Anti-His-tag mAb-HRP-DirecT (MLB). As a result, it was shown that GH1-2 with the His-tag added at the C-terminus expressed in cells was leaked to the cell reaction mixture (the upper right panel of FIG. 9). In addition, each cell reaction mixture filtered with a 0.22 μm pore size filter was diluted with deionized water, and analyzed by the ion-exchange chromatography mentioned above, to quantify gentiobiose. As a result, no difference in the generation amount of gentiobiose was observed with or without stirring (the lower right panel of FIG. 9).

(4-6) Cellulase production culture using gentiobiose

The *T. cellulolyticus* strains F09ΔcreA and F09Δgh1-2ΔcreA were each inoculated into PD medium, and cultured at 30° C. One agar disk excised from around the edge of a formed colony was inoculated into 20 mL of a liquid culture medium containing 20 g/L glucose, 24 g/L $KH_2PO_4$, 5 g/L $(NH_4)_2SO_4$, 2 g/L Urea, 1.2 g/L $MgSO_4$-$7H_2O$, 0.01 g/L $ZnSO_4$-$7H_2O$, 0.01 g/L $MnSO_4$-$5H_2O$, 0.01 g/L $CuSO_4$-$5H_2O$, 1 g/L Corn steep liquor (C4648, SIGMA), and 1 g/L Tween 80, and gyratory culture (220 rpm) was carried out at 30° C. for 5 days as a pre-culture. Then, 15 mL of the pre-culture broth was inoculated into 300 mL of a liquid culture medium containing 15 g/L glucose, 12 g/L $KH_2PO_4$, 10 g/L $(NH_4)_2SO_4$, 1.2 g/L $MgSO_4$-$7H_2O$, 0.01 g/L $ZnSO_4$-$7H_2O$, 0.01 g/L $MnSO_4$-$5H_2O$, 0.01 g/L $CuSO_4$-$5H_2O$, 5 g/L Corn steep liquor, 1 g/L Tween 80, and 0.5 mL/L DISFOAM GD (NOF CORPORATION) contained in a jar fermenter, and fed-batch culture was carried out for 72 hours at a culture temperature of 30° C. and an aeration volume of 1/2vvm, while controlling the dissolved oxygen concentration to be 5% or higher of the saturated oxygen concentration by stirring and controlling the pH to be 5 with using ammonia gas. A feeding solution was continuously fed starting at 22-hours after the start of the culture so that the glucose concentration in the culture medium was maintained within a range of 5 to 10 g/L. The culture broth was sampled at 72-hours after start of the culture, and centrifuged (15000 rpm for 5 minutes), to thereby obtain a supernatant. The obtained supernatant was used as an enzyme solution.

As the feeding solution, eight feeding solutions were used, and two of them were the saccharide solution prepared by using cells of the purified GH1-2, which contains gentiobiose and has a concentration corresponding to 560 g/L glucose (hereinafter, also referred to as "+GH1-2 purified enzyme"), and the saccharide solution prepared by using cells of the *E. coli* strain EcGHH6, which contains gentiobiose and diluted with water to provide a concentration corresponding to 560 g/L glucose (hereinafter, also referred to as "+GH1-2-expressing *E. coli* cells"). The compositions of the remaining six feeding solutions are shown in Table 4.

TABLE 4

| | Glucose (g/L) | Gentiobiose (g/L) | Cellobiose (g/L) |
|---|---|---|---|
| Gentiobiose 80 g/L | 480 | 80 | 0 |
| Gentiobiose 8 g/L | 552 | 8 | 0 |
| Gentiobiose 0.8 g/L | 559.2 | 0.8 | 0 |
| Cellobiose 80 g/L | 480 | 0 | 80 |
| Cellobiose 8 g/L | 552 | 0 | 8 |
| Glucose 560 g/L | 560 | 0 | 0 |

The filter paper degradation activity (FPU/ml) of the obtained enzyme solutions was measured according to the following procedure, and the yield of the activity per carbon source was calculated on the basis of the consumption amount of sugar during the cultures by which the respective enzyme solutions were obtained.

<Filter paper decomposition activity (FPU/mL)>

To a 100-μl aliquot of a citrate buffer (50 mM, pH 5.0) containing a filter paper (Whatman No. 1, GE Healthcare) cut to 6 mm×10 mm, 50 μl of an appropriately diluted sample were added, and a reaction was carried out at 50° C. for 1 hour. Separately, a sample for which no reaction was carried out was prepared and used as a blank. Next, 300 μl of a DNS solution (1% dinitrosalicylic acid, 20% potassium sodium tartrate, 0.05% sodium sulfite, and 1% sodium hydroxide) was added, and the mixture was allowed to react at 95° C. for 5 minutes, and then cooled on ice for 5 minutes. The solution after the reaction was mixed and centrifuged (12000 rpm for 5 minutes), and 100 μl of the supernatant was collected. Then, the absorbance at 540 nm of the supernatant was measured, and the value of the blank was subtracted therefrom, to calculate an increase in absorbance. Next, the amount of a reducing sugar generated in the reaction solution was calculated in terms of glucose by using a calibration curve prepared from the concentration of glucose diluted stepwise and the absorbance at 540 nm. The same operation was carried out for samples with different dilution ratios, a calibration curve of the dilution ratio and the glucose generation amount was prepared, and the dilution ratio of the sample required to generate a reducing sugar equivalent to 0.2 mg of glucose was calculated, to thereby calculate the filter paper decomposition activity (FPU/mL) of the sample before dilution. Regarding the activity unit, an enzyme activity for generating a reducing sugar corresponding to 1 μmol of glucose per minute was defined as "1 U".

As a result, it was shown that cellulase production with higher efficiency can be achieved by using gentiobiose as a carbon source other than glucose in the feed solution than when using cellobiose (FIG. 10).

Furthermore, it was shown that the efficiency of cellulase production by addition of the feed solution containing gentiobiose can be improved by disruption of the gh1-2 gene (FIG. 11).

In addition, it was shown that both the saccharide solution prepared by using cells of the purified GH1-2, which contains gentiobiose and has a concentration corresponding to 560 g/L glucose, and the saccharide solution prepared by using cells of the *E. coli* strain EcGHH6, which contains gentiobiose and has a concentration corresponding to 560 g/L glucose, can achieve cellulase production with high efficiency comparable to the case of using a feed solution containing 80 g/L cellobiose (FIG. 12).

(5) Generation of gentiobiose by extracellular-secretion type beta-glucosidase BGL3A Methods for preparing gentiobiose by using GH1-2, which is a beta-glucosidase localized in cells, were described above. Hereinafter, methods for preparing gentiobiose by using BGL3A (SEQ ID NO: 38), which is a major beta-glucosidase secreted outside cells other than GH1-2, are described.

(5-1) Construction of bgl3A gene-disruption strain

The strain F09Δbgl3A was constructed from the parent strain *T. cellulolyticus* strain F09 (Japanese Patent Laid-open (Kokai) No. 2016-131533) by disruption of the bgl3A gene encoding BGL3A according to the following procedure.

First, a DNA fragment for bgl3A disruption having a nucleotide sequence consisting of an upstream region of the bgl3A gene, a pyrF gene marker, and a downstream region of the bgl3A gene of *T. cellulolyticus* ligated in this order was prepared according to the following procedure.

PCR was performed by using the genomic DNA of the *T. cellulolyticus* strain Y-94 (FERM BP-5826) as the template in combination with primers of SEQ ID NOS: 39 and 40, to amplify the upstream region of the bgl3A gene, or in combination with primers of SEQ ID NOS: 41 and 42, to amplify the downstream region of the bgl3A gene. Separately, PCR was performed by using the genomic DNA of the *T. cellulolyticus* strain Y-94 (FERM BP-5826) as the template and primers of SEQ ID NOS: 43 and 44, to amplify a whole region (including promoter and terminator) of the pyrF gene. The PCR products were each purified by using Wizard SV Gel and PCR Clean-Up System (Promega). In-Fusion HD Cloning Kit (Takara Bio) was used to incorporate the purified PCR products into a pUC plasmid included in the kit and to thereby ligate them. *E. coli* JM109 was transformed with the reaction product, and cultured on LB agar medium containing 100 mg/L ampicillin at 37° C. overnight, to form colonies. A plasmid pUC-bgl3A::pyrF, into which the DNA fragment for bgl3A disruption has been incorporated, was obtained from an obtained transformant by using Wizard Plus Miniprep System (Promega). PCR was performed by using the plasmid pUC-bgl3A::pyrF as the template and primers of SEQ ID NOS: 45 and 46, to amplify the DNA fragment for bgl3A disruption, and the fragment was concentrated and purified by ethanol precipitation.

Then, the strain F09 was inoculated into PD medium, and cultured at 30° C. One agar disk excised from around the edge of a formed colony was inoculated into a culture medium containing 24 g/L Potato Dextrose Broth, and gyratory culture (220 rpm) was carried out at 30° C. for 2 days. To cells collected by centrifugation (5000 rpm for 5 minutes), 30 mL of a solution containing 10 g/L Yatalase (Takara Bio), 10 mM $KH_2PO_4$, and 0.8 M NaCl (pH6.0) were added. Reaction was carried out at 30° C. for 2 hours with shaking, to digest cell walls and prepare protoplasts. After residues were removed by using a glass filter, protoplasts were collected by centrifugation (2000 rpm for 10 minutes), and suspended with Tris-HCl buffer (pH7.5) containing 1.2 M Sorbitol and 10 mM $CaCl_2$, to prepare 1 mL of a protoplast solution. To a 200-μL aliquot of the protoplast solution, 10 μg of the purified DNA fragment for bgl3A disruption, and 50 μL of Tris-HCl buffer (pH7.5) containing 400 g/L PEG4000 and 10 mM $CaCl_2$ were added, and left on ice for 30 minutes. Then, 1 mL of Tris-HCl buffer (pH7.5) containing 400 g/L PEG4000 and 10 mM $CaCl_2$ was further added to the mixture, and it was left at a room temperature for 15 minutes to allow for transformation. Protoplasts were collected by centrifugation (2000 rpm for 10 minutes), inoculated to a minimal medium containing 1 M sucrose, and cultured at 30° C. for 7 days, to select strains in which the uracil auxotrophy was complemented. A colony that appeared was inoculated to a minimal medium and cultured at 30° C. for 4 days, and then replacement of the bgl3A gene with the pyrF gene was confirmed, to obtain the strain F09Δbgl3A.

(5-2) Preparation of enzyme solutions

Cellulase solutions produced by the *T. cellulolyticus* strains F09Δbgl3A and F09pyr+ were prepared by flask culture using Solka-Floc (International Fiber Corporation), which is a cellulosic substrate, as a carbon source.

<Flask culture>

The strains F09Δbgl3A and F09pyr+ were each inoculated into a 1/2 PDA plate, and cultured at 30° C. for 3 days. One agar disk excised from around the edge of a formed colony formed was inoculated into a SF flask medium (Table 2), and gyratory culture (220 rpm) was carried out at 30° C. for 7 days. Sampling was appropriately carried out, cells were removed using a 0.22 μm syringe filter, and the obtained culture supernatant was used as an enzyme solution. Thereby, an enzyme solution derived from the strain F09Δbgl3A not containing BGL3A (hereinafter, also referred to as "-BGL3A") and an enzyme solution derived from the strain F09pyr+ containing BGL3A (hereinafter, also referred to as "+BGL3A") were prepared.

(5-3) Generation of gentiobiose from cellulosic substrate

The two enzyme solutions obtained in Example (5-2) were used to degrade Solka-Floc (International Fiber Corporation), which is a cellulosic substrate, under conditions of containing a certain concentration of glucose, and the product was analyzed. The reaction was carried out by placing 10 g of the reaction solution (Table 5) in a 50-ml tube and shaking the tube at 90 rpm at 50° C. for 24 hours.

TABLE 5

| No. | Total Weight of Reaction Mixture (g) | Weight of Solka froc (g) | 1M pH 4.88 Citrate Buffer (g) | Added 60%(wt %) glucose (g) | Added glucose concentration (wt %) | Added Amount of Enzyme Solution (g) | Amount of Enzyme Protein in Added Enzyme solution (mg) | Distilled Water (g) |
|---|---|---|---|---|---|---|---|---|
| 1 | 10.00 | 0.27 | 1.10 | 0.00 | 0.0% | 4.30 | 10.02 | 4.33 |
| 2 | 10.00 | 0.27 | 1.10 | 0.60 | 3.6% | 4.30 | 10.02 | 3.73 |
| 3 | 10.00 | 0.27 | 1.10 | 2.40 | 14.4% | 4.30 | 10.02 | 1.93 |
| 4 | 10.00 | 0.27 | 1.10 | 0.00 | 0.0% | 2.80 | 10.00 | 5.83 |
| 5 | 10.00 | 0.27 | 1.10 | 0.60 | 3.6% | 2.80 | 10.00 | 5.23 |
| 6 | 10.00 | 0.27 | 1.10 | 2.40 | 14.4% | 2.80 | 10.00 | 3.43 |
| 7 | 10.00 | — | 1.10 | 0.00 | 0.0% | 4.30 | 10.02 | 4.60 |
| 8 | 10.00 | — | 1.10 | 0.60 | 3.6% | 4.30 | 10.02 | 4.00 |
| 9 | 10.00 | — | 1.10 | 2.40 | 14.4% | 4.30 | 10.02 | 2.20 |
| 10 | 10.00 | — | 1.10 | 0.00 | 0.0% | 2.80 | 10.00 | 6.10 |
| 11 | 10.00 | — | 1.10 | 0.60 | 3.6% | 2.80 | 10.00 | 5.50 |
| 12 | 10.00 | — | 1.10 | 2.40 | 14.4% | 2.80 | 10.00 | 3.70 |

Results are shown in FIG. 13. When using the enzyme solution derived from the strain F09Δbgl3A not containing BGL3A, generation of gentiobiose was scarcely observed, and accumulation of cellobiose was observed. By contrast, when using the enzyme solution derived from the strain F09pyr+ containing BGL3A, accumulation of cellobiose was reduced, and an increase in glucose accumulation and generation of gentiobiose were confirmed. In addition, even under conditions of not adding the cellulosic substrate, generation of gentiobiose was confirmed under conditions of containing glucose, and hence, it was shown that BGL3A can generate gentiobiose from glucose in a concentration-dependent manner. Thus, it was shown that gentiobiose can be prepared by using an enzyme solution containing the BGL3A enzyme, which is a major beta-glucosidase other than GH1-2.

(5-4) Generation of gentiobiose from cellobiose

Similarly, gentiobiose generation using BGL3A was investigated by using cellobiose, which is a decomposition product of a cellulosic substrate.

The two enzyme solutions obtained in Example (5-2) were used to degrade cellobiose, which is a decomposition product of a cellulosic substrate, under conditions of containing a certain concentration of glucose, and the product was analyzed. The reaction was carried out by placing 10 g of the reaction solution (Table 6) in a 50-ml tube and shaking the tube at 90 rpm at 50° C. for 24 hours.

(6-1) Preparation of mutant GH1-2s

A PCR product amplified by PCR using pET24a-gh1-2-His6 constructed in Example (2-1) as the template and primers of SEQ ID NOS: 52 and 53 was purified by using Wizard SV Gel and PCR Clean-Up System (Promega). In-Fusion HD Cloning Kit (Takara Bio) was used to ligate the purified PCR product. *E. coli* JM109 was transformed with the reaction product, and cultured on LB agar medium containing 50 mg/L kanamycin at 37° C. overnight, to form colonies. A plasmid pET24a-gh1-2(W363F)-His6, into which the cDNA fragment of the mutant gh1-2 gene having the W363F mutation of replacing tryptophan at position 363 of GH1-2 with phenylalanine, was obtained from an obtained transformant by using Wizard Plus Miniprep System (Promega). Separately, a plasmid pET24a-gh1-2 (W449F)-His6, into which the cDNA fragment of the mutant gh1-2 gene having the W449F mutation of replacing tryptophan at position 449 of GH1-2 with phenylalanine, was obtained in the similar manner using primers of SEQ ID NOS: 54 and 55.

*E. coli* Rosetta™ 2(DE3)pLysS Competent Cells (Novagen) were transformed with each of the plasmids pET24a-gh1-2(W363F)-His6 and pET24a-gh1-2(W449F)-His6, and cultured on LB agar medium containing 50 mg/L kanamycin at 37° C. overnight, to form colonies. The colonies that formed were streaked on LB agar medium containing 50 mg/L kanamycin, and single colonies were obtained, to thereby obtain strains EcGHW363FH6 and EcGHW449FH6.

TABLE 6

| No. | Total Weight of Reaction Mixture (g) | Weight of cellobiose (g) | 1M pH 4.88 Citrate Buffer (g) | Added 60%(wt %) glucose (g) | Added glucose concentration (wt %) | Added Amount of Enzyme Solution (g) | Amount of Enzyme Protein in Added Enzyme solution (mg) | Distilled Water (g) |
|---|---|---|---|---|---|---|---|---|
| 1 | 10.00 | 0.50 | 1.10 | 0.00 | 0.0% | 2.15 | 5.01 | 6.25 |
| 2 | 10.00 | 0.50 | 1.10 | 0.60 | 3.6% | 2.15 | 5.01 | 5.65 |
| 3 | 10.00 | 0.50 | 1.10 | 1.50 | 9.0% | 2.15 | 5.01 | 4.75 |
| 4 | 10.00 | 0.50 | 1.10 | 2.40 | 14.4% | 2.15 | 5.01 | 3.85 |
| 5 | 10.00 | 0.50 | 1.10 | 0.00 | 0.0% | 1.40 | 5.00 | 7.00 |
| 6 | 10.00 | 0.50 | 1.10 | 0.60 | 3.6% | 1.40 | 5.00 | 6.40 |
| 7 | 10.00 | 0.50 | 1.10 | 1.50 | 9.0% | 1.40 | 5.00 | 5.50 |
| 8 | 10.00 | 0.50 | 1.10 | 2.40 | 14.4% | 1.40 | 5.00 | 4.60 |

Results are shown in FIG. 14. When using the enzyme solution derived from the strain F09pyr+ containing BGL3A, generation of gentiobiose from cellobiose, which is a decomposition product of a cellulosic substrate, was confirmed. By contrast, when using the enzyme solution derived from the strain F09Δbgl3A not containing BGL3A, not only degradation of cellobiose was reduced, but also generation of gentiobiose was not confirmed. From these results, it was shown that BGL3A can generate gentiobiose from cellobiose. Furthermore, in combination with the results of Example (5-3), it was shown that gentiobiose can be generated from a cellulosic substrate via cellobiose by using a cell culture of *T. cellulolyticus* containing BGL3A.

(6) Evaluation of cellulase production culture using a strain having attenuated activity of GH1-2

It was shown, in Example (4-6), that the efficiency of cellulase production by adding gentiobiose can be improved by disrupting the gh1-2 gene. Thus, next, it was investigated whether the efficiency of cellulase production under various conditions can be improved by reducing the activity of the gh1-2 gene product (GH1-2).

The strains EcGHW363FH6 and EcGHW449FH6 were each inoculated into 3 mL of LB medium containing 50 mg/L kanamycin in a test tube, and cultured with shaking (120 rpm) at 37° C. overnight. The culture broth was inoculated into 50 mL of LB medium containing 50 mg/L kanamycin contained in a shaking flask in a volume of 1/100, and cultured with shaking (120 rpm) at 37° C. until OD600 reached 0.8. Then, the shaking flask was moved into a box shaker (13° C.), and culture was carried out with shaking (120 rpm) at 13° C. for 1 hour. Then, IPTG was added at a concentration of 1 mM, and culture was further continued for 17 hours. After the culture, cells were collected by centrifugation (4° C., 5000 rpm, 5 min), and frozen for 1 hour in a freezer (−20° C.). Then, soluble proteins were extracted from the cells by using Ni-NTA Fast Start Kit (QIAGEN) under non-denaturing conditions, and two mutant GH1-2s with the His-tag added at the C-terminus were each purified by using a Ni-NTA affinity column, a wash buffer, and an elution buffer included in the kit. A fraction containing the purified GH1-2 was desalinated and concentrated by using Amicon Ultra-15 30 kDa cut off (Merck Millipore) ultrafiltration membrane filter and 50 mM sodium phosphate buffer (pH 6.5). The two purified mutant GH1-2s were each confirmed to provide a single band in SDS-PAGE, and used for the following experiment.

(6-2) Evaluation of activity of mutant GH1-2s

A comparison was made between the hydrolysis activities of the two purified mutant GH1-2s and the purified wild-type GH1-2 obtained in Example (2-1). First, the protein concentrations of the enzyme solutions of wild-type GH1-2 and the mutant GH1-2s were adjusted to be identical to each other. Then, the enzyme solutions were each diluted so that the absorbance of the sample after the reaction at a wavelength of 410 nm was within the range of the calibration curve, to thereby obtain a diluted enzyme solution. The diluted enzyme solution (10 μl) was added to 1 ml of a substrate solution (50 mM sodium phosphate buffer (pH 6.5) containing 10 mM p-Nitrophenyl-β-D-glucopyranoside (Wako Pure Chemical Industry)), and incubated at 45° C. for 10 minutes. Then, the mixture was incubated at 95° C. for 10 minutes to thereby inactivate the enzyme, cooled to a room temperature, and then the absorbance at a wavelength of 410 nm was measured. A measurement result of a sample that was not incubated but was subjected to only the inactivation treatment at 95° C. for 10 minutes was subtracted as the background. A calibration curve was prepared by diluting p-nitrophenol (Fluka Chemical Corp) in 50 mM sodium phosphate buffer and measuring the absorbance. The hydrolysis activity of each GH1-2 was calculated as a relative value with the hydrolysis activity of wild-type GH1-2 being 100% by using the generation amount of p-nitrophenol as an indicator of the hydrolysis activity. As a result, it was shown that the two mutant GH1-2s (W363F and W449F) each have a reduced hydrolysis activity (FIG. 15).

In addition, a comparison was made between hydrolysis products and transglycosylation products obtained upon reaction of the two purified mutant GH1-2s and the purified wild-type GH1-2 obtained in Example (2-1) with cellobiose. The reaction mixture was developed and colorized by TLC according to the method described in Example (3-2). Results are shown in FIG. 16. It was shown that the two mutant GH1-2s (W363F and W449F) each have a reduced hydrolysis activity. When using a larger amount (5 times) of the W363F mutant GH1-2, a development pattern similar to that observed when using the wild-type GH1-2 was observed, and hence, it was suggested that generation of transglycosylation products are also decreased. When using the W449F mutant GH1-2, hydrolysis of cellobiose and transglycosylation were scarcely observed, and it was observed that cellobiose was very slightly hydrolyzed to produce glucose.

The reaction mixture obtained by using the wild-type GH1-2 was subject to ion exchange chromatography under the conditions described in Example (2-2), and the reaction product was analyzed, and observation of the hydrolysis product and the transglycosylation product was carried out over time. As a result, in the case of the wild-type GH1-2, it was shown that cellotriose and cellotetraose are generated prior to gentiobiose, and cello-oligosaccharides such as cellobiose were degraded prior to gentiobiose (FIG. 17).

Similarly, the reaction mixture obtained by using the W363F mutant GH1-2 was subject to ion exchange chromatography under the conditions described in Example (2-2), the reaction product was analyzed, and observation of the hydrolysis product and the transglycosylation product was carried out over time, and the result was compared with that observed when using the wild-type GH1-2 was observed. As a result, in the case of the W363F mutant GH1-2, it was shown that not only the hydrolysis efficiency of cellobiose is reduced but also generation of cellotriose and gentiobiose is delayed (FIG. 18). That is, it was shown that the W363F mutant GH1-2 has not only a lower hydrolysis efficiency of cellobiose but also a lower generation efficiency of transglycosylation products.

In a strain having such a mutant GH1-2, it is considered that cellobiose taken up into the cell and transglycosylation products thereof are hardly hydrolyzed to glucose, and the abundance thereof in the cytoplasm is thus increased. That is, in a strain having such a mutant GH1-2, it is estimated that transglycosylation products such as gentiobiose, which induces the expression of cellulase genes, are stably supplied, and thus the expression of cellulase is improved. By contrast, in a strain having the wild-type GH1-2, it is estimated that the efficiency of producing transglycosylation products from cellobiose in the cytoplasm is high, but the efficiency of hydrolyzing the substrate thereof, cellobiose, and transglycosylation products is also remarkably high, hence, the supply of transglycosylation products such as gentiobiose, which induces the expression of cellulase genes, becomes unstable, and thus the expression of cellulase is restricted.

(6-3) Discovery of effective mutation C267P in gh1-2 gene in past breeding of *T. cellulolyticus*

Sequencing analysis of the gh1-2 gene region was carried out using the genomic DNA of the *T. cellulolyticus* strains Y-94 (FERM BP-5826), TN (FERM BP-685), and F09 as a template, and primers (SEQ ID NOs: 16, 17, 18, 19, 20, and 21). As a result, it was revealed that the C267P mutation of replacing cysteine at position 267 of GH1-2 with proline was introduced into the gh1-2 gene during the breeding process in which the strain TN was constructed from the strain Y-94 (FIG. 19). Japanese Patent Laid-open (Kokai) No. 2011-193773 reports that the strain TN has 2513 mutation candidate sites. However, Japanese Patent Laid-open (Kokai) No. 2011-193773 does not mention this C267P mutation.

(6-4) Introduction of C267P mutation into gh1-2 gene of *T. cellulolyticus* strain Y-94

PCR was performed by using the genomic DNA of the *T. cellulolyticus* strain TN (FERM BP-685) as the template and primers of SEQ ID NOS: 56 and 57, to amplify a DNA fragment from 4 kb upstream to 4 kb downstream of the gh1-2 gene containing the C267P mutation. The PCR product was purified by using Wizard SV Gel and PCR Clean-Up System (Promega). In-Fusion HD Cloning Kit (Takara Bio) was used to incorporate the purified PCR products into a pUC plasmid included in the kit and to thereby ligate them. *E. coli* JM109 was transformed with the reaction product, and cultured on LB agar medium containing 100 mg/L ampicillin at 37° C. overnight, to form colonies. A plasmid pUC-gh1-2TN, into which the aforementioned DNA fragment has been incorporated, was obtained from an obtained transformant by using Wizard Plus Miniprep System (Promega).

Next, PCR was performed by using the plasmid pUC-gh1-2TN as the template and primers of SEQ ID NOS: 58 and 59, to amplify a DNA fragment of the plasmid pUC-gh1-2TN cleaved at approximately 0.5 kb downstream of the stop codon of the gh1-2 gene. Separately, PCR was performed by using the plasmid pcDNA3.1/Hygro(+) (Invitrogen) as the template and primers of SEQ ID NOS: 60 and 61, to amplify a hygromycin-resistant gene cassette region (including promoter and terminator). The PCR products were each purified by using Wizard SV Gel and PCR Clean-Up System (Promega). In-Fusion HD Cloning Kit (Takara Bio) was used to incorporate the purified PCR products into a pUC plasmid included in the kit and to thereby ligate them. *E. coli* JM109 was transformed with the reaction product, and cultured on LB agar medium containing 100 mg/L ampicillin at 37° C. overnight, to form colonies. A plasmid pUC-C267Prep, into which the region from 4 kb upstream to 4 kb downstream of the gh1-2 gene containing the C267P mutation and the hygromycin-resistant gene have been incorporated, was obtained from an obtained transformant by using Wizard Plus Miniprep System (Promega). PCR was performed by using the plasmid pUC-C267Prep as the template and primers of SEQ ID NOS: 56 and 57, to amplify the DNA fragment for substitution of the gh1-2 gene region, and the fragment was concentrated and purified by ethanol precipitation.

Then, the strain Y-94 was inoculated into PD medium, and cultured at 30° C. One agar disk excised from around the edge of a formed colony was inoculated to a culture medium containing 24 g/L Potato Dextrose Broth, and gyratory culture (220 rpm) was carried out at 30° C. for 2 days. To cells collected by centrifugation (5000 rpm for 5 minutes), 30 mL of a solution containing 10 g/L Yatalase (Takara Bio), 10 mM $KH_2PO_4$, and 0.8 M NaCl (pH6.0) were added. Reaction was carried out at 30° C. for 2 hours with shaking, to digest cell walls and prepare protoplasts. After residues were removed by using a glass filter, protoplasts were collected by centrifugation (2000 rpm for 10 minutes), and suspended with Tris-HCl buffer (pH7.5) containing 1.2 M Sorbitol and 10 mM $CaCl_2$), to prepare 1 mL of a protoplast solution. To a 200-μL aliquot of the protoplast solution, 10 μg of the purified DNA fragment for substitution of the gh1-2 gene region, and 50 μL of Tris-HCl buffer (pH7.5) containing 400 g/L PEG4000 and 10 mM $CaCl_2$) were added, and left on ice for 30 minutes. Then, 1 mL of Tris-HCl buffer (pH7.5) containing 400 g/L PEG4000 and 10 mM $CaCl_2$) were further added to the mixture, and left at a room temperature for 15 minutes to allow for transformation. Protoplasts were collected by centrifugation (2000 rpm for 10 minutes), inoculated to a minimal medium (Table 1) containing 1 M sucrose, cultured at 30° C. for 1 day, then overlaid with a minimal medium (Table 1) containing 0.5 g/L hygromycin B and 1 M sucrose, and cultured at 30° C. for 7 days, to select strains imparted with hygromycin resistance. A colony that appeared was inoculated to a minimal medium containing 0.5 g/L hygromycin B and cultured at 30° C. for 4 days, and then replacement of the gh1-2 gene region with the gh1-2 gene region containing the C267P mutation was confirmed, to obtain the strain C267Prep.

(6-5) Evaluation of cellulase production of strain C267Prep by flask culture

Cellulase production by the strains Y-94, C267Prep, and TN was evaluated by flask culture using Solka-Floc (International Fiber Corporation), which is a cellulosic substrate, as a carbon source according to the procedure described in Example (1-2). The total protein concentration in the culture supernatant was used as an indicator of cellulase production. As a result, it was shown that the strains C267Prep and TN have a significantly increased ability for secretory production of cellulase and a significantly increased cellulose assimilability as compared to the parent strain Y-94 (FIG. 20).

(6-6) Evaluation of cellulase production of strain C267Prep by halo assay

Cellulase production by the strains Y-94, C267Prep, and TN was evaluated by halo assay using CMC, which is a cellulosic substrate, as a carbon source according to the procedure described in Example (1-4). As a result, it was again shown that the strains C267Prep and TN have a significantly increased ability for secretory production of cellulase and a significantly increased cellulose assimilability as compared to the parent strain Y-94 (FIG. 21).

(6-7) Introduction of W363F mutation and W449F mutation into gh1-2 gene of *T. cellulolyticus* strain Y-94

PCR was performed by using the genomic DNA of the *T. cellulolyticus* strain Y-94 (FERM BP-5826) as the template and primers of SEQ ID NOS: 56 and 57, to amplify a DNA fragment from 4 kb upstream to 4 kb downstream of the gh1-2 gene. The PCR product was purified by using Wizard SV Gel and PCR Clean-Up System (Promega). In-Fusion HD Cloning Kit (Takara Bio) was used to incorporate the purified PCR products into a pUC plasmid included in the kit and to thereby ligate them. *E. coli* JM109 was transformed with the reaction product, and cultured on LB agar medium containing 100 mg/L ampicillin at 37° C. overnight, to form colonies. A plasmid pUC-gh1-2WT, into which the aforementioned DNA fragment has been incorporated, was obtained from an obtained transformant by using Wizard Plus Miniprep System (Promega).

Next, PCR was performed by using the plasmid pUC-gh1-2WT as the template and primers of SEQ ID NOS: 58 and 59, to amplify a DNA fragment of the plasmid pUC-gh1-2WT cleaved at approximately 0.5 kb downstream of the stop codon of the gh1-2 gene. Separately, PCR was performed by using the plasmid pcDNA3.1/Hygro(+) (Invitrogen) as the template and primers of SEQ ID NOS: 60 and 61, to amplify a hygromycin-resistant gene cassette region (including promoter and terminator). The PCR products were each purified by using Wizard SV Gel and PCR Clean-Up System (Promega). In-Fusion HD Cloning Kit (Takara Bio) was used to incorporate the purified PCR products into a pUC plasmid included in the kit and to thereby ligate them. *E. coli* JM109 was transformed with the reaction product, and cultured on LB agar medium containing 100 mg/L ampicillin at 37° C. overnight, to form colonies. A plasmid pUC-WTrep, into which the region from 4 kb upstream to 4 kb downstream of the gh1-2 gene and the hygromycin-resistant gene have been incorporated, was obtained from an obtained transformant by using Wizard Plus Miniprep System (Promega).

In addition, a PCR product amplified by PCR using the plasmid pUC-WTrep as the template and primers of SEQ ID NOS: 52 and 53 was purified by using Wizard SV Gel and PCR Clean-Up System (Promega). In-Fusion HD Cloning Kit (Takara Bio) was used to ligate the purified PCR product. *E. coli* JM109 was transformed with the reaction product, and cultured on LB agar medium containing 50 mg/L kanamycin at 37° C. overnight, to form colonies. A plasmid pUC-W363Frep, into which the region from 4 kb upstream to 4 kb downstream of the gh1-2 gene containing the W363F mutation and the hygromycin-resistant gene have been incorporated, was obtained from an obtained transformant by using Wizard Plus Miniprep System (Promega). Separately, a plasmid pUC-W449Frep, into which the region from 4 kb upstream to 4 kb downstream of the gh1-2 gene containing the W449F mutation and the hygromycin-resistant gene have been incorporated, was obtained in the similar manner using primers of SEQ ID NOS: 54 and 55.

PCR was performed by using each of the plasmids pUC-W363Frep and pUC-W449Frep as the template and primers of SEQ ID NOS: 56 and 57, to amplify the DNA fragment for substitution of the gh1-2 gene region, and the fragment was concentrated and purified by ethanol precipitation.

Then, the strain Y-94 was inoculated into PD medium, and cultured at 30° C. One agar disk excised from around the edge of a formed colony was inoculated to a culture medium containing 24 g/L Potato Dextrose Broth, and gyratory culture (220 rpm) was carried out at 30° C. for 2 days. To cells collected by centrifugation (5000 rpm for 5 minutes), and 30 mL of a solution containing 10 g/L Yatalase (Takara Bio), 10 mM $KH_2PO_4$, and 0.8 M NaCl (pH6.0) were added. Reaction was carried out at 30° C. for 2 hours with shaking, to digest cell walls and prepare protoplasts. After residues were removed by using a glass filter, protoplasts were collected by centrifugation (2000 rpm for 10 minutes), and suspended with Tris-HCl buffer (pH7.5) containing 1.2 M Sorbitol and 10 mM $CaCl_2$), to prepare 1 mL of a protoplast solution. To a 200-μL aliquot of the protoplast solution, 10 μg of the purified DNA fragment for substitution of the gh1-2 gene region, and 50 μL of Tris-HCl buffer (pH7.5) containing 400 g/L PEG4000 and 10 mM $CaCl_2$) were added, and left on ice for 30 minutes. Then, 1 mL of Tris-HCl buffer (pH7.5) containing 400 g/L PEG4000 and 10 mM $CaCl_2$) was added to the mixture, and left at a room temperature for 15 minutes to allow for transformation. Protoplasts were collected by centrifugation (2000 rpm for 10 minutes), inoculated into a minimal medium (Table 1) containing 1 M sucrose, cultured at 30° C. for 1 day, then overlaid with a minimal medium (Table 1) containing 0.5 g/L hygromycin B and 1 M sucrose, and cultured at 30° C. for 7 days, to select strains imparted with hygromycin resistance. A colony that appeared was inoculated to a minimal medium containing 0.5 g/L hygromycin B and cultured at 30° C. for 4 days, and then replacement of the gh1-2 gene region with the gh1-2 gene region containing the W363F mutation or the W449F mutation was confirmed, to obtain the strains W363Frep and W449Frep.

(6-8) Evaluation of cellulase production of strains W363Frep and W449Frep by flask culture Cellulase production by the strains Y-94, C267Prep, W363Frep, and W449Frep was evaluated by flask culture using Solka-Floc (International Fiber Corporation), which is a cellulosic substrate, as a carbon source according to the procedure described in Example (1-2). The total protein concentration and the specific activity of cellulase in the culture supernatant were used as indicators of cellulase production. As a result, it was shown that the strains W363Frep and W449Frep have a significantly increased ability for secretory production of cellulase and a significantly increased cellulose assimilability as compared to the parent strain Y-94 (FIG. 22).

(6-9) Evaluation of cellulase production of strains W363Frep, W449Frep, and C267Prep by halo assay The strains Y-94, W363Frep, W449Frep, and C267Prep were each grown on the minimal medium containing CMC as the carbon source and on the minimal medium containing CMC as the carbon source and 1 mM gentiobiosefor 5 days according to the procedure described in Example (1-4). After the culture, a Congo Red solution obtained by mixing 50 mM sodium phosphate buffer (pH 7.0) and 2 mg/ml Congo Red (Nacalai Tesque) in a volume ratio of 10:1 was added to the plate so that the Congo Red solution covered the whole of the plate, and the plate was left to stand for 30 minutes at a room temperature. Then, the Congo Red solution on the plate was removed, and sodium phosphate buffer (50 mM, pH 7.0) was added to the plate so that the sodium phosphate buffer covered the whole of the plate. The plate was again left to stand for 30 minutes at a room temperature. Then, the sodium phosphate buffer on the plate was removed, the surface of the plate was dried lightly, and the diameter and width of the visualized halo were measured.

Results are shown in FIG. 23. The strains W363Frep, W449Frep, and C267Prep provided a significantly larger diameter and width of the degradation halo as compared with the parent strain Y-94 both in the case of not adding gentiobiose and the case of adding gentiobiose, and that is, it was again shown that these strains have a significantly increased cellulase secretory production ability and a significantly increased cellulose assimilability. In addition, it was shown that the strains W363Frep, W449Frep, and C267Prep provide an increased degree of enlarging of the diameter and width of the degradation halo by addition of gentiobiose as compared with the parent strain Y-94. From these results, secretory production of cellulase is synergistically improved by a combination of addition of gentiobiose and these mutations in the gh1-2 gene.

(7) Culture of double deficient strain of GH1-2 and BGL3A using gentiobiose (7-1) Construction of strain F09ΔGHΔBGL3A The strain F09Δgh1-2Δbgl3A was constructed from the *T. cellulolyticus* strain F09Δgh1-2ΔpyrF constructed in Example (4-3) as a parent strain by disruption of the bgl3A gene encoding BGL3A according to the following procedure.

First, PCR was performed by using the plasmid pUC-bgl3A::pyrF constructed in Example (5-1) as the template and primers of SEQ ID NOS: 45 and 46, to amplify the DNA fragment for bgl3A disruption, and the fragment was concentrated and purified by ethanol precipitation.

Then, the strain F09Δgh1-2ΔpyrF was inoculated into PD medium, and cultured at 30° C. One agar disk excised from around the edge of a formed colony was inoculated to a culture medium containing 24 g/L Potato Dextrose Broth, and gyratory culture (220 rpm) was carried out at 30° C. for 2 days. To cells collected by centrifugation (5000 rpm for 5 minutes), 30 mL of a solution containing 10 g/L Yatalase (Takara Bio), 10 mM $KH_2PO_4$, and 0.8 M NaCl (pH6.0) were added. Reaction was carried out at 30° C. for 2 hours with shaking, to digest cell walls and prepare protoplasts. After residues were removed by using a glass filter, protoplasts were collected by centrifugation (2000 rpm for 10 minutes), and suspended with Tris-HCl buffer (pH7.5) containing 1.2 M Sorbitol and 10 mM $CaCl_2$), to prepare 1 mL of a protoplast solution. To a 200-4, aliquot of the protoplast solution, of the purified DNA fragment for bgl3A disruption, and 50 μl, L of Tris-HCl buffer (pH7.5) containing 400 g/L PEG4000 and 10 mM $CaCl_2$) were added, and left on ice for 30 minutes. Then, 1 mL of Tris-HCl buffer (pH7.5) containing 400 g/L PEG4000 and 10 mM $CaCl_2$) were added to the mixture, and left at a room temperature for 15 minutes to allow for transformation. Protoplasts were collected by centrifugation (2000 rpm for 10 minutes), inoculated to a minimal medium containing 1 M sucrose, and cultured at 30° C. for 7 days, to select strains of which the uracil auxotrophy was complemented. A colony that appeared was inoculated to a minimal medium and cultured at 30° C. for 4 days, and then replacement of the bgl3A gene with the pyrF gene was confirmed, to obtain the strain F09Δgh1-2Δbgl3A.

(7-2) Evaluation of cellulase production of double deficient strain of GH1-2 and BGL3A by plate halo assay The strains F09pyrF+ and F09Δgh1-2 constructed in Example (1-1), the strain F09Δbgl3A constructed in Example (5-1), and the strain F09Δgh1-2Δbgl3A constructed in Example (7-1) were each grown on the minimal medium containing CMC as the carbon source and on the minimal medium containing CMC as the carbon source and 1 mM gentiobiosefor 5 days according to the procedure described in Example (1-4). After the culture, a Congo Red solution obtained by mixing 50 mM sodium phosphate buffer (pH 7.0) and 2 mg/ml Congo Red (Nacalai Tesque) in a volume ratio of 10:1 was added to the plate so that the Congo Red solution covered the whole of the plate, and the plate was left to stand for 30 minutes at a room temperature. Then, the Congo Red solution on the plate was removed, and sodium phosphate buffer (50 mM, pH 7.0) was added to the plate so that the sodium phosphate buffer covered the whole of the plate. The plate was again left to stand for 30 minutes at a room temperature. Then, the sodium phosphate buffer on the plate was removed, the surface of the plate was dried lightly, and the diameter and width of the visualized halo were measured.

Results are shown in FIG. 24. The double deficient strain F09Δgh1-2Δbgl3A provided an increased degree of enlarging of the width of the degradation halo in the case of adding gentiobiose as compared with the strains F09pyrF+, F09Δgh1-2, and F09Δbgl3A, and that is, it was shown that the double deficient strain has an increased ability for secretory production of cellulase. From this result, secretory production of cellulase is synergistically improved by a combination of addition of gentiobiose and double disruption of the gh1-2 gene and the bgl3A gene. That is, it was suggested that secretory production of cellulase is synergistically improved by addition of expression inducer such as gentiobiose and a reduction in the activity of GH1-2 in combination with a reduction in the activity of another beta-glucosidase such as BGL3A.

(8) Expression of heterologous protein (8-1) Construction of *T. cellulolyticus* yscB gene-deletion strain F09ΔyscB The strain F09ΔyscB was constructed from the *Talaromyces cellulolyticus* strain F09 (Japanese Patent Laid-open (Kokai) No. 2016-131533) as a parent strain by disruption of the yscB gene (SEQ ID NO: 62) according to the following procedure.

First, a DNA fragment for yscB gene disruption having a nucleotide sequence consisting of an upstream region of the yscB gene of *T. cellulolyticus*, a hygromycin-resistant gene, and a downstream region of the yscB gene of *T. cellulolyticus* ligated in this order was prepared according to the following procedure.

PCR was performed by using the genomic DNA of the *T. cellulolyticus* strain Y-94 (FERM BP-5826) as the template in combination with primers of SEQ ID NOS: 63 and 64, to amplify the upstream region of the yscB gene, or in combination with primers of SEQ ID NOS: 65 and 66, to amplify the downstream region of the yscB gene. Separately, PCR was performed by using pcDNA3.1/Hygro(+) (Life Technologies) containing the hygromycin-resistant gene as the template and primers of SEQ ID NOS: 67 and 68, to amplify the hygromycin-resistant gene (including promoter and terminator). The PCR products were each purified by using Wizard SV Gel and PCR Clean-Up System (Promega). In-Fusion HD Cloning Kit (Takara Bio) was used to incorporate the purified PCR products into a pUC plasmid included in the kit and to thereby ligate them. *E. coli* JM109 was transformed with the reaction product, and cultured on LB agar medium containing 100 mg/L ampicillin at 37° C. overnight, to form colonies. A plasmid pUC-yscB::hyg, into which the DNA fragment for yscB gene disruption has been incorporated, was obtained from an obtained transformant by using Wizard Plus Miniprep System (Promega). PCR was performed by using the plasmid pUC-yscB::hyg as the template and primers of SEQ ID NOS: 63 and 66, to amplify the DNA fragment for yscB gene disruption, and the fragment was concentrated and purified by ethanol precipitation.

Then, the strain F09 was inoculated to a culture medium containing 12 g/L Potato Dextrose Broth (Difco) and 20 g/L Bacto Agar (Difco), and cultured at 30° C. One agar disk excised from around the edge of a colony formed on the agar medium was inoculated to a culture medium containing 24 g/L Potato Dextrose Broth, and gyratory culture (220 rpm) was carried out at 30° C. for 2 days. To cells collected by centrifugation (5000 rpm for 5 minutes), 30 mL of a solution containing 10 g/L Yatalase (Takara Bio), 10 mM $KH_2PO_4$, and 0.8 M NaCl (pH6.0) were added. Reaction was carried out at 30° C. for 2 hours with shaking, to digest cell walls and prepare protoplasts. After residues were removed by using a glass filter, protoplasts were collected by centrifugation (2000 rpm for 10 minutes), and suspended with Tris-HCl buffer (pH7.5) containing 1.2 M Sorbitol and 10 mM $CaCl_2$), to prepare 1 mL of a protoplast solution. To a 200-μL aliquot of the protoplast solution, 10 μg of the purified DNA fragment for yscB disruption, and 50 μL of Tris-HCl buffer (pH7.5) containing 400 g/L PEG4000 and 10 mM $CaCl_2$) were added, and left on ice for 30 minutes. Then, 1 mL of Tris-HCl buffer (pH7.5) containing 400 g/L PEG4000 and 10 mM $CaCl_2$) was added to the mixture, and left at a room temperature for 15 minutes to allow for transformation. Protoplasts were collected by centrifugation (2000 rpm for 10 minutes), inoculated into a minimal medium (10 g/L Glucose, 10 mM $NH_4Cl$, 10 mM $KH_2PO_4$, 7 mM KCl, 2 mM $MgSO_4$, 0.06 mg/L $H_3BO_3$, 0.26 mg/L $(NH_4)_6Mo_7O_{24}$-$4H_2O$, 1 mg/L $FeCl_3$-$6H_2O$, 0.4 mg/L $CuSO_4$-$5H_2O$, 0.08 mg/L $MnCl_2$, 2 mg/L $ZnCl_2$, and 20 g/L Bacto Agar) containing 1 M sucrose, 1 g/L uracil, and 1 g/L uridine, cultured at 30° C. for 1 day, then overlaid with a medium containing 0.5 g/L Hygromycin B, 24 g/L Potato Dextrose Broth, and 7 g/L Bacto Agar, and further cultured at 30° C. for 3 days, to select hygromycin-resistant strains. A colony that appeared was inoculated into a minimal medium containing 0.5 g/L Hygromycin B and cultured at 30° C. for 4 days, and then replacement of the yscB gene with the hygromycin-resistant gene was confirmed, to obtain the strain F09ΔyscB, which is a yscB gene-disruption strain derived from F09.

(8-2) Construction of strains expressing human serum albumin (HSA)

Strains expressing human serum albumin (HSA) were constructed from the parent strains *T. cellulolyticus* strains F09 and F09ΔyscB according to the following procedure.

First, a DNA fragment for expressing HSA having a nucleotide sequence consisting of an upstream region of the creA gene of *T. cellulolyticus*, an upstream region of the cbh2 gene (cbh2 promoter; SEQ ID NO: 50) of *T. cellulolyticus*, a coding sequence of cbh1 secretion signal (SEQ ID NO: 70), a HSA gene (SEQ ID NO: 71), a downstream region of the cbh2 gene (cbh2 terminator; SEQ ID NO: 72) of *T. cellulolyticus*, a pyrF gene marker (SEQ ID NO: 73) of *T. cellulolyticus*, and a downstream region of the creA gene of *T. cellulolyticus* ligated in this order was prepared according to the following procedure.

PCR was performed by using the genomic DNA of the *T. cellulolyticus* strain Y-94 (FERM BP-5826) as the template in combination with primers of SEQ ID NOS: 74 and 75, to amplify the upstream region of the creA gene, in combination with primers of SEQ ID NOS: 76 and 77, to amplify the upstream region of the cbh2 gene, in combination with primers of SEQ ID NOS: 78 and 79, to amplify the coding sequence of cbh1 secretion signal, in combination with primers of SEQ ID NOS: 80 and 81, to amplify the downstream region of the cbh2 gene, in combination with primers of SEQ ID NOS: 82 and 83, to amplify the downstream region of the pyrF gene marker, or in combination with primers of SEQ ID NOS: 84 and 85, to amplify the downstream region of the creA gene. Separately, PCR was performed by using a totally synthesized gene purchased from Eurofins as the template and primers of SEQ ID NOS: 86 and 87, to amplify the HSA gene. The PCR products were purified by using Wizard SV Gel and PCR Clean-Up System (Promega). The purified PCR products were mutually ligated by repeating PCR using a mixture of each combination of two of the purified PCR products as the template, and incorporated by using In-Fusion HD Cloning Kit (Takara Bio) into a pUC plasmid included in the kit. *E. coli* JM109 was transformed with the reaction product, and cultured on LB agar medium containing 100 mg/L ampicillin at 37° C. overnight, to form colonies. A plasmid pUC-creA::Pcbh2-HSA-pyrF, into which the DNA fragment for expressing HSA has been incorporated, was obtained from an obtained transformant by using Wizard Plus Miniprep System (Promega). PCR was performed by using the plasmid pUC-creA::Pcbh2-HSA-pyrF as the template and primers of SEQ ID NOS: 76 and 85, to amplify the DNA fragment for expressing HSA, and the fragment was concentrated and purified by ethanol precipitation. Incidentally, ligation of the upstream and downstream regions of the creA gene at the respective ends of the HSA expressing sequence enables insertion of the HSA expressing sequence not into a random site of the genome but into the creA gene region as the target.

Then, the strains F09 and F09ΔyscB were each cultured and converted to protoplasts in a similar manner to Example (8-1), and transformed with the purified DNA fragment for expressing HSA in a similar manner to Example (8-1). The protoplasts were collected by centrifugation (2000 rpm for 10 minutes), inoculated into a minimal medium containing 1 M sucrose, and cultured at 30° C. for 7 days, to select strains of which the uracil auxotrophy was complemented. A colony that appeared was inoculated into a minimal medium and cultured at 30° C. for 4 days, and then replacement of the creA gene region with the HSA expressing sequence was confirmed, to obtain HSA expressing strains derived from the strains F09 and F09ΔyscB.

(8-3) Culture of strains expressing human serum albumin (HSA) using gentiobiose

Fed-batch culture was carried out for confirming secretory production HSA when culturing the HSA expressing strain derived from the strain F09ΔyscB.

The HSA expressing strain derived from the *T. cellulolyticus* strain F09ΔyscB was inoculated into PD medium, and cultured at 30° C. One agar disk excised from around the edge of a formed colony was inoculated into 20 mL of a liquid culture medium containing 20 g/L glucose, 24 g/L $KH_2PO_4$, 5 g/L $(NH_4)_2SO_4$, 2 g/L Urea, 1.2 g/L $MgSO_4$-$7H_2O$, 0.01 g/L $ZnSO_4$-$7H_2O$, 0.01 g/L $MnSO_4$-$5H_2O$, 0.01 g/L $CuSO_4$-$5H_2O$, 1 g/L Corn steep liquor (C4648, SIGMA), and 1 g/L Tween 80, and gyratory culture (220 rpm) was carried out at 30° C. for 5 days as a pre-culture. Then, 15 mL of the pre-culture broth was inoculated into 300 mL of a liquid culture medium containing 15 g/L glucose, 12 g/L $KH_2PO_4$, 10 g/L $(NH_4)_2SO_4$, 1.2 g/L $MgSO_4$-$7H_2O$, 0.01 g/L $ZnSO_4$-$7H_2O$, 0.01 g/L $MnSO_4$-$5H_2O$, 0.01 g/L $CuSO_4$-$5H_2O$, 5 g/L Corn steep liquor, 1 g/L Tween 80, and 0.5 mL/L DISFOAM GD (NOF CORPORATION) in a jar fermenter, and fed-batch culture was carried out for 45 hours at a culture temperature of 30° C. and an aeration volume of 1/2 vvm, while controlling the dissolved oxygen concentration to be 5% or higher of the saturated oxygen concentration by stirring and controlling the pH to be 5 with using ammonia gas. A feeding solution was continuously fed from 22-hours after start of the culture so that the glucose concentration in the culture medium was maintained within a range of 5 to 10 g/L. The culture broth was sampled at 45-hours after start of the culture, and centrifuged (15000 rpm for 5 minutes), to thereby obtain a supernatant. The obtained supernatant was used as a culture supernatant sample solution. As the feeding solution, two feeding solutions were used, and the compositions thereof are shown in Table 7.

TABLE 7

| | Glucose (g/L) | Gentiobiose (g/L) | Cellobiose (g/L) |
|---|---|---|---|
| Gentiobiose 80 g/L | 480 | 80 | 0 |
| Cellobiose 80 g/L | 480 | 0 | 80 |

HSA was quantified by ELISA using Albumin ELISA Quantitation Kit, Human (Bethyl Laboratories, inc.). As a result, it was confirmed that the secretory production amount of HSA was greater in the case of feeding gentiobiose than in the case of feeding cellobiose (FIG. 25). From this result, it was shown that secretory production a heterologous protein under control of a promoter inducible by gentiobiose can be improved by addition of gentiobiose.

INDUSTRIAL APPLICABILITY

According to the present invention, a protein such as cellulase can be efficiently produced. Furthermore, according to the present invention, a disaccharide such as gentiobiose can be efficiently produced.

EXPLANATION OF SEQUENCE LISTING

SEQ ID NOS:

1: Nucleotide sequence of gh1-2 gene of *Talaromyces cellulolyticus* strain Y-94

2-21: Primers

22: Nucleotide sequence of cDNA of gh1-2 gene of *Talaromyces cellulolyticus* strain Y-94

23: Amino acid sequence of GH1-2 protein of *Talaromyces cellulolyticus* strain Y-94

24-37: Primers

38: Amino acid sequence of BGL3A protein of *Talaromyces cellulolyticus* strain S6-25

39-46: Primers

47: Nucleotide sequence of creA gene of *Talaromyces cellulolyticus* strain S6-25

48: Nucleotide sequence of bgl3A gene of *Talaromyces cellulolyticus* strain S6-25

49: Nucleotide sequence of cbh1 promoter of *Talaromyces cellulolyticus*

50: Nucleotide sequence of cbh2 promoter of *Talaromyces cellulolyticus*

51: Amino acid sequence of Cbh1 signal peptide of *Talaromyces cellulolyticus*

52-61: Primers

62: Nucleotide sequence of yscB gene of *Talaromyces cellulolyticus* strain S6-25

63-68: Primers

69: Amino acid sequence of YscB protein of *Talaromyces cellulolyticus* strain S6-25

70: Nucleotide sequence encoding Cbh1 signal peptide of *Talaromyces cellulolyticus*

71: Amino acid sequence of human serum albumin (HSA)

72: Nucleotide sequence of cbh2 terminator of *Talaromyces cellulolyticus*

73: Nucleotide sequence of pyrF gene marker of *Talaromyces cellulolyticus*

74-87: Primers

The invention claimed is:

1. A method for producing an objective protein, comprising culturing *Talaromyces cellulolyticus* that has an ability to produce an objective protein in a culture medium comprising an expression inducer, wherein the expression inducer is gentiobiose, and wherein the *Talaromyces cellulolyticus* has a genetic construct which allows for expression of the objective protein;

wherein the *Talaromyces cellulolyticus* has a feature selected from the group consisting of:

(A) the *Talaromyces cellulolyticus* has been modified so that the activity of a beta-glucosidase other than a GH1-2 protein is reduced as compared with a non-modified *Talaromyces cellulolyticus;*

(B) the *Talaromyces cellulolyticus* has been modified so that the activity of a CreA protein is reduced as compared with a non-modified *Talaromyces cellulolyticus;*

(C) the *Talaromyces cellulolyticus* has been modified so that the activity of a YscB protein is reduced as compared with a non-modified *Talaromyces cellulolyticus*; and (D) combinations thereof;

wherein the beta-glucosidase is a BGL3A protein, wherein the BGL3A protein is selected from the group consisting of:

(a) a protein comprising the amino acid sequence of SEQ ID NO: 38;

(b) a protein comprising the amino acid sequence of SEQ ID NO: 38, but which includes substitution, deletion, insertion, and/or addition of 1 to 10 amino acid residues, and wherein said protein has a disaccharide hydrolysis activity; and (c) a protein comprising an amino acid sequence having an identity of 90% or higher to the amino acid sequence of SEQ ID NO: 38, and wherein said protein has a disaccharide hydrolysis activity.

2. The method according to claim 1, wherein the *Talaromyces cellulolyticus* has a feature selected from the group consisting of:

(A) the *Talaromyces cellulolyticus* has been modified so that the activity of a GH1-2 protein is reduced as compared with a non-modified *Talaromyces cellulolyticus* by a method selected from the group consisting of:

(A1) reducing the expression of a gh1-2 gene encoding the GH1-2 protein, (A2) disrupting a gh1-2 gene encoding the GH1-2 protein, (A3) modifying a gh1-2 gene encoding the GH1-2 protein so as to have a mutation that improves the objective protein-producing ability of the *Talaromyces cellulolyticus*, and (A4) combinations thereof;

(B) the *Talaromyces cellulolyticus* has been modified so that a gh1-2 gene encodes a GH1-2 protein having a mutation that improves the ability to produce the objective protein; and (C) combinations thereof;

wherein the GH1-2 protein of (A) is selected from the group consisting of:

(a) a protein comprising the amino acid sequence of SEQ ID NO: 23;

(b) a protein comprising the amino acid sequence of SEQ ID NO: 23, but which includes substitution, deletion, insertion, and/or addition of 1 to 10 amino acid residues, and wherein said protein has a disaccharide hydrolysis activity; and (c) a protein comprising an amino acid sequence having an identity of 90% or higher to the amino acid sequence of SEQ ID NO: 23, and wherein said protein has a disaccharide hydrolysis activity;

wherein the GH1-2 protein of (B) is a protein comprising the amino acid sequence of the protein (a), (b), or (c), but which includes the mutation;

wherein the mutation that improves the ability to produce the objective protein is a mutation selected from the group consisting of:

(i) replacing an amino acid residue corresponding to the cysteine residue at position 267 in SEQ ID NO: 23 with another amino acid residue;

(ii) replacing an amino acid residue corresponding to the tryptophan residue at position 363 in SEQ ID NO: 23 with another amino acid residue;

(iii) replacing an amino acid residue corresponding to the tryptophan residue at position 449 in SEQ ID NO: 23 with another amino acid residue; and (iv) combinations thereof.

3. A method for producing an objective protein, comprising culturing *Talaromyces cellulolyticus* that has an ability to produce an objective protein in a culture medium comprising an expression inducer, wherein the *Talaromyces cellulolyticus* has a feature selected from the group consisting of:

(A) the *Talaromyces cellulolyticus* has been modified so that the activity of a GH1-2 protein is reduced as compared with a non-modified *Talaromyces cellulolyticus* by a method selected from the group consisting of:

(A1) reducing the expression of a gh1-2 gene encoding the GH1-2 protein, (A2) disrupting a gh1-2 gene encoding the GH1-2 protein, (A3) modifying a gh1-2 gene encoding the GH1-2 protein so as to have a mutation that improves the objective protein-producing ability of the *Talaromyces cellulolyticus*, and (A4) combinations thereof;

(B) the *Talaromyces cellulolyticus* has been modified so that a gh1-2 gene encodes a GH1-2 protein having a mutation that improves the ability to produce the objective protein; and (C) combinations thereof; and wherein the expression inducer is a saccharide comprising glucose as a constituent sugar;

wherein the GH1-2 protein of (A) is selected from the group consisting of:

(a) a protein comprising the amino acid sequence of SEQ ID NO: 23;

(b) a protein comprising the amino acid sequence of SEQ ID NO: 23, but which includes substitution, deletion, insertion, and/or addition of 1 to 10 amino acid residues, and wherein said protein has a disaccharide hydrolysis activity; and (c) a protein comprising an amino acid sequence having an identity of 90% or higher to the amino acid sequence of SEQ ID NO: 23, and wherein said protein has a disaccharide hydrolysis activity; and wherein the GH1-2 protein of (B) is a protein comprising the amino acid sequence of the protein (a), (b), or (c), but which includes the mutation;

wherein the mutation that improves the ability to produce the objective protein is a mutation selected from the group consisting of:

(i) replacing an amino acid residue corresponding to the cysteine residue at position 267 in SEQ ID NO: 23 with another amino acid residue;

(ii) replacing an amino acid residue corresponding to the tryptophan residue at position 363 in SEQ ID NO: 23 with another amino acid residue;

(iii) replacing an amino acid residue corresponding to the tryptophan residue at position 449 in SEQ ID NO: 23 with another amino acid residue; and (iv) combinations thereof;

provided that the expression inducer is gentiobiose when the activity of the GH1-2 protein is completely eliminated.

4. The method according to claim 3, wherein the expression inducer is gentiobiose, cellobiose, or cellulose.

5. The method according to claim 3, wherein the expression inducer is gentiobiose.

6. The method according to claim 2, wherein the activity of the GH1-2 protein is reduced by deletion of a gh1-2 gene.

7. The method according to claim 2, wherein said another amino acid in the (i) mutation is a proline residue; wherein said another amino acid in the (ii) mutation is a phenylalanine residue; and wherein said another amino acid in the (iii) mutation is a phenylalanine residue.

8. The method according to claim 1, wherein the *Talaromyces cellulolyticus* is a modified strain derived from *Talaromyces cellulolyticus* strain S6-25 (NITE BP-01685) or Y-94 (FERM BP-5826).

9. The method according to claim 1, wherein the objective protein is accumulated in the culture medium by the culturing.

10. The method according to claim 1, wherein the objective protein is expressed under control of a promoter that functions in *Talaromyces cellulolyticus* and is inducible by the expression inducer.

11. The method according to claim 10, wherein the promoter is a cbhI promoter or a cbhII promoter.

12. The method according to claim 1, wherein the objective protein is expressed as a fused protein with a signal peptide that functions in *Talaromyces cellulolyticus*.

13. The method according to claim 1, wherein the objective protein is cellulase.

14. The method according to claim 2, further comprising producing the gentiobiose by an enzymatic conversion from a saccharide raw material using a disaccharide synthesizing enzyme, wherein the enzymatic conversion is carried out by bringing the disaccharide synthesizing enzyme into contact with the saccharide raw material.

15. The method according to claim 14, wherein the enzymatic conversion is carried out by bringing *Escherichia coli* cells containing the disaccharide synthesizing enzyme into contact with the saccharide raw material.

16. The method according to claim 14, wherein the saccharide raw material is selected from the group consisting of glucose, cellobiose, cellulose, and combinations thereof.

17. The method according to claim 3, wherein the activity of the GH1-2 protein is reduced by deletion of a gh1-2 gene.

18. The method according to claim 3, wherein said another amino acid in the (i) mutation is a proline residue; wherein said another amino acid in the (ii) mutation is a phenylalanine residue; and wherein said another amino acid in the (iii) mutation is a phenylalanine residue.

* * * * *

SEQUENCE LISTING

<160> NUMBER OF SEQ ID NOS: 87

<210> SEQ ID NO 1
<211> LENGTH: 1700
<212> TYPE: DNA
<213> ORGANISM: Talaromyces cellulolyticus

<400> SEQUENCE: 1

```
atgggtagcg taactagtac caacggcgag actccccagt ccaaactgcc ggcagacttt     60

gtctggggat acgcaacggc caggtgagat tactcgctat tcatgtgtgt agaagaaacc    120

tatttaccgt cttgttttgg ttctagctac cagatcgaag gagcgtatga cgaagacggc    180

cgaggacctt ccatctggga tacattcagc aagacacctg gaaaagtaga ggatggcacc    240

aatggcgacg tggcctgcga ctcctaccac cgtacacatg aggatattgc gattctgaag    300

caatatggtg ccaagctgta ccgcttttct ctgtcctggt atagctccct tcggcttctt    360

gcgccagaat ataactgaca gtattgataa tcaaggcccc gaatcattcc tctaggtggc    420

cgaaacgacc ccatcaacca aaagggaata gacttttact ccaaattcat cgacgatctc    480

cacgccgctg gaatcgagcc cttcgtcacc ttgtaccact gggatcttcc cgacgagctg    540

ttcaagagat acggcggccc cctcaacaag gacgaattcg tggctgacta tgcgaacttc    600

gcccgcatcg cattccagag ctttggacac aaagtcaagc attgggttac cttcaatgaa    660

ccatggtgta gctccgtgct cggtttcaat atcggtaagc atgcgccagg acggacgagc    720

gatcgcaaga agaacccggt tggtgatggt gtgcgtgagc catggattgc tggtcattcc    780

cttttggtgg ctcacggcac ggctgttgat atctaccgga aggaatttaa gcctacacag    840

ggcggagaaa ttggcattac actcaatggt tagatcgaaa tattccccaa cgcatgacaa    900

tcatgcgcta atatgaattc aaggtgactg ggccgaaccc tgggaccccg aagacccaga    960

agacattgaa gcctgcaccc gcaaactcga attcgccatc tcctggtttg cagaccccat   1020

ctaccttggc aaataccccg acagcgtcgt gaaacaaatc ggcgaccgtc tcccaccctt   1080

gacacccgat gaagtagcct tgatcaaggg aagcaacgac ttttacggca tgaaccacta   1140

ctgcgcaaac tacatccgtc accgagaagg tgaagcggat ccagacgaca cagccggaaa   1200

cttggaccat ttgtttgagg ataaattcgg aaactcgatt ggacccgaga cgaattgtga   1260

atggcttcgc cctcatccct tgggattcag gaagttgttg aaatggcttt cggatcgtta   1320

tggttatccc aaaatctatg ttacggagaa cgggacgagt atcaagggcg agaacgactt   1380

gccactagag gaactcctca atgatgagtt tagggtgcag tattaccggg attatgtcgg   1440

tgccatggct gatgctgcta cttttgacgg agtcaatgtt aagaaatata tggcctggag   1500

tttgatggag taagtcaaaa catcacctat tcggaaagac ttctgctaat cgctctatta   1560

gtaacttcga gtggtccgaa ggttaccaat ccagatttgg tgtcacatac gtcgactaca   1620

aggacaacca gaaacgtatc cccaagaaga gtgccctcgt cattggagaa ttgttcaaca   1680

aatacatctc gaaagagtag                                                1700
```

<210> SEQ ID NO 2
<211> LENGTH: 45
<212> TYPE: DNA
<213> ORGANISM: Artificial Sequence
<220> FEATURE:
<223> OTHER INFORMATION: primer

<400> SEQUENCE: 2

```
cggtacccgg ggatccacac gagttgctac aacctcaatt acctg                    45
```

<210> SEQ ID NO 3
<211> LENGTH: 43
<212> TYPE: DNA
<213> ORGANISM: Artificial Sequence
<220> FEATURE:
<223> OTHER INFORMATION: primer

<400> SEQUENCE: 3
ccgatctgaa ttgacctcgg agatgtgttg gatgtgattc tgc 43

<210> SEQ ID NO 4
<211> LENGTH: 40
<212> TYPE: DNA
<213> ORGANISM: Artificial Sequence
<220> FEATURE:
<223> OTHER INFORMATION: primer

<400> SEQUENCE: 4
tcggcgttca cttatcaatc atatcacgct cgctttggcc 40

<210> SEQ ID NO 5
<211> LENGTH: 42
<212> TYPE: DNA
<213> ORGANISM: Artificial Sequence
<220> FEATURE:
<223> OTHER INFORMATION: primer

<400> SEQUENCE: 5
cgactctaga ggatcgtcat aggtggcccg tttaaagaca gc 42

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
gtcaattcag atcggctgcc gc 22

<210> SEQ ID NO 7
<211> LENGTH: 35
<212> TYPE: DNA
<213> ORGANISM: Artificial Sequence
<220> FEATURE:
<223> OTHER INFORMATION: primer

<400> SEQUENCE: 7
ataagtgaac gccgagtcag tactatatgt agatg 35

<210> SEQ ID NO 8
<211> LENGTH: 37
<212> TYPE: DNA
<213> ORGANISM: Artificial Sequence
<220> FEATURE:
<223> OTHER INFORMATION: primer

<400> SEQUENCE: 8
cggtacccgg ggatcgtcaa ttcagatcgg ctgccgc 37

<210> SEQ ID NO 9
<211> LENGTH: 50
<212> TYPE: DNA
<213> ORGANISM: Artificial Sequence
<220> FEATURE:

<223> OTHER INFORMATION: primer

<400> SEQUENCE: 9
cgactctaga ggatcataag tgaacgccga gtcagtacta tatgtagatg 50

<210> SEQ ID NO 10
<211> LENGTH: 44
<212> TYPE: DNA
<213> ORGANISM: Artificial Sequence
<220> FEATURE:
<223> OTHER INFORMATION: primer

<400> SEQUENCE: 10
gattacgcca agcttcgtcc ttgttgaggg ggccgccgta tctc 44

<210> SEQ ID NO 11
<211> LENGTH: 44
<212> TYPE: DNA
<213> ORGANISM: Artificial Sequence
<220> FEATURE:
<223> OTHER INFORMATION: primer

<400> SEQUENCE: 11
gattacgcca agcttcgaag acggccgagg accttccatc tggg 44

<210> SEQ ID NO 12
<211> LENGTH: 42
<212> TYPE: DNA
<213> ORGANISM: Artificial Sequence
<220> FEATURE:
<223> OTHER INFORMATION: primer

<400> SEQUENCE: 12
aagaaggaga tatacatggg tagcgtaact agtaccaacg gc 42

<210> SEQ ID NO 13
<211> LENGTH: 73
<212> TYPE: DNA
<213> ORGANISM: Artificial Sequence
<220> FEATURE:
<223> OTHER INFORMATION: primer

<400> SEQUENCE: 13
gttagcagcc ggatctcagt ggtggtggtg gtggtgctct ttcgagatgt atttgttgaa 60
caattctcca atg 73

<210> SEQ ID NO 14
<211> LENGTH: 43
<212> TYPE: DNA
<213> ORGANISM: Artificial Sequence
<220> FEATURE:
<223> OTHER INFORMATION: primer

<400> SEQUENCE: 14
gtatatctcc ttcttaaagt taaacaaaat tatttctaga ggg 43

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15
gatccggctg ctaacaaagc ccg 23

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
tcttccccat cggtgatgtc gg 22

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
gtctggggat acgcaacggc c 21

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
ccgaatcatt cctctaggtg gccg 24

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
tatcggtaag catgcgccag gacg 24

<210> SEQ ID NO 20
<211> LENGTH: 25
<212> TYPE: DNA
<213> ORGANISM: Artificial Sequence
<220> FEATURE:
<223> OTHER INFORMATION: primer

<400> SEQUENCE: 20
ttcgccatct cctggtttgc agacc 25

<210> SEQ ID NO 21
<211> LENGTH: 29
<212> TYPE: DNA
<213> ORGANISM: Artificial Sequence
<220> FEATURE:
<223> OTHER INFORMATION: primer

<400> SEQUENCE: 21
caggaagttg ttgaaatggc tttcggatc 29

<210> SEQ ID NO 22
<211> LENGTH: 1473
<212> TYPE: DNA
<213> ORGANISM: Talaromyces cellulolyticus

<400> SEQUENCE: 22

```
atgggtagcg taactagtac caacggcgag actccccagt ccaaactgcc ggcagacttt      60
gtctggggat acgcaacggc cagctaccag atcgaaggag cgtatgacga agacggccga     120
ggaccttcca tctgggatac attcagcaag acacctggaa aagtagagga tggcaccaat     180
ggcgacgtgg cctgcgactc ctaccaccgt acacatgagg atattgcgat tctgaagcaa     240
tatggtgcca agctgtaccg cttttctctg tcctggcccc gaatcattcc tctaggtggc     300
cgaaacgacc ccatcaacca aaagggaata gacttttact ccaaattcat cgacgatctc     360
cacgccgctg gaatcgagcc cttcgtcacc ttgtaccact gggatcttcc cgacgagctg     420
ttcaagagat acggcggccc cctcaacaag gacgaattcg tggctgacta tgcgaacttc     480
gcccgcatcg cattccagag ctttggacac aaagtcaagc attgggttac cttcaatgaa     540
ccatggtgta gctccgtgct cggtttcaat atcggtaagc atgcgccagg acggacgagc     600
gatcgcaaga agaacccggt tggtgatggt gtgcgtgagc catggattgc tggtcattcc     660
cttttggtgg ctcacggcac ggctgttgat atctaccgga aggaatttaa gcctacacag     720
ggcggagaaa ttggcattac actcaatggt gactgggccg aaccctggga ccccgaagac     780
ccagaagaca ttgaagcctg cacccgcaaa ctcgaattcg ccatctcctg gtttgcagac     840
cccatctacc ttggcaaata ccccgacagc gtcgtgaaac aaatcggcga ccgtctccca     900
cccttgacac ccgatgaagt agccttgatc aagggaagca acgactttta cggcatgaac     960
cactactgcg caaactacat ccgtcaccga gaaggtgaag cggatccaga cgacacagcc    1020
ggaaacttgg accatttgtt tgaggataaa ttcggaaact cgattggacc cgagacgaat    1080
tgtgaatggc ttcgccctca tcccttggga ttcaggaagt tgttgaaatg gctttcggat    1140
cgttatggtt atcccaaaat ctatgttacg gagaacggga cgagtatcaa gggcgagaac    1200
gacttgccac tagaggaact cctcaatgat gagtttaggg tgcagtatta ccgggattat    1260
gtcggtgcca tggctgatgc tgctactttt gacggagtca atgttaagaa atatatggcc    1320
tggagtttga tggataactt cgagtggtcc gaaggttacc aatccagatt tggtgtcaca    1380
tacgtcgact acaaggacaa ccagaaacgt atccccaaga agagtgccct cgtcattgga    1440
gaattgttca acaaatacat ctcgaaagag tag                                 1473
```

<210> SEQ ID NO 23
<211> LENGTH: 490
<212> TYPE: PRT
<213> ORGANISM: Talaromyces cellulolyticus

<400> SEQUENCE: 23

```
Met Gly Ser Val Thr Ser Thr Asn Gly Glu Thr Pro Gln Ser Lys Leu
1               5                   10                  15

Pro Ala Asp Phe Val Trp Gly Tyr Ala Thr Ala Ser Tyr Gln Ile Glu
            20                  25                  30

Gly Ala Tyr Asp Glu Asp Gly Arg Gly Pro Ser Ile Trp Asp Thr Phe
        35                  40                  45

Ser Lys Thr Pro Gly Lys Val Glu Asp Gly Thr Asn Gly Asp Val Ala
    50                  55                  60

Cys Asp Ser Tyr His Arg Thr His Glu Asp Ile Ala Ile Leu Lys Gln
65                  70                  75                  80

Tyr Gly Ala Lys Leu Tyr Arg Phe Ser Leu Ser Trp Pro Arg Ile Ile
                85                  90                  95

Pro Leu Gly Gly Arg Asn Asp Pro Ile Asn Gln Lys Gly Ile Asp Phe
```

```
            100                 105                 110

Tyr Ser Lys Phe Ile Asp Asp Leu His Ala Ala Gly Ile Glu Pro Phe
        115                 120                 125

Val Thr Leu Tyr His Trp Asp Leu Pro Asp Glu Leu Phe Lys Arg Tyr
    130                 135                 140

Gly Gly Pro Leu Asn Lys Asp Glu Phe Val Ala Asp Tyr Ala Asn Phe
145                 150                 155                 160

Ala Arg Ile Ala Phe Gln Ser Phe Gly His Lys Val Lys His Trp Val
                165                 170                 175

Thr Phe Asn Glu Pro Trp Cys Ser Ser Val Leu Gly Phe Asn Ile Gly
            180                 185                 190

Lys His Ala Pro Gly Arg Thr Ser Asp Arg Lys Lys Asn Pro Val Gly
        195                 200                 205

Asp Gly Val Arg Glu Pro Trp Ile Ala Gly His Ser Leu Leu Val Ala
    210                 215                 220

His Gly Thr Ala Val Asp Ile Tyr Arg Lys Glu Phe Lys Pro Thr Gln
225                 230                 235                 240

Gly Gly Glu Ile Gly Ile Thr Leu Asn Gly Asp Trp Ala Glu Pro Trp
                245                 250                 255

Asp Pro Glu Asp Pro Glu Asp Ile Glu Ala Cys Thr Arg Lys Leu Glu
            260                 265                 270

Phe Ala Ile Ser Trp Phe Ala Asp Pro Ile Tyr Leu Gly Lys Tyr Pro
        275                 280                 285

Asp Ser Val Val Lys Gln Ile Gly Asp Arg Leu Pro Pro Leu Thr Pro
    290                 295                 300

Asp Glu Val Ala Leu Ile Lys Gly Ser Asn Asp Phe Tyr Gly Met Asn
305                 310                 315                 320

His Tyr Cys Ala Asn Tyr Ile Arg His Arg Glu Gly Glu Ala Asp Pro
                325                 330                 335

Asp Asp Thr Ala Gly Asn Leu Asp His Leu Phe Glu Asp Lys Phe Gly
            340                 345                 350

Asn Ser Ile Gly Pro Glu Thr Asn Cys Glu Trp Leu Arg Pro His Pro
        355                 360                 365

Leu Gly Phe Arg Lys Leu Leu Lys Trp Leu Ser Asp Arg Tyr Gly Tyr
    370                 375                 380

Pro Lys Ile Tyr Val Thr Glu Asn Gly Thr Ser Ile Lys Gly Glu Asn
385                 390                 395                 400

Asp Leu Pro Leu Glu Glu Leu Leu Asn Asp Glu Phe Arg Val Gln Tyr
                405                 410                 415

Tyr Arg Asp Tyr Val Gly Ala Met Ala Asp Ala Ala Thr Phe Asp Gly
            420                 425                 430

Val Asn Val Lys Lys Tyr Met Ala Trp Ser Leu Met Asp Asn Phe Glu
        435                 440                 445

Trp Ser Glu Gly Tyr Gln Ser Arg Phe Gly Val Thr Tyr Val Asp Tyr
    450                 455                 460

Lys Asp Asn Gln Lys Arg Ile Pro Lys Lys Ser Ala Leu Val Ile Gly
465                 470                 475                 480

Glu Leu Phe Asn Lys Tyr Ile Ser Lys Glu
                485                 490
```

<210> SEQ ID NO 24
<211> LENGTH: 40
<212> TYPE: DNA
<213> ORGANISM: Artificial Sequence
<220> FEATURE:
<223> OTHER INFORMATION: primer

<400> SEQUENCE: 24
cggtacccgg ggatcccctt cttgccagca cactgctccg 40

<210> SEQ ID NO 25
<211> LENGTH: 40
<212> TYPE: DNA
<213> ORGANISM: Artificial Sequence
<220> FEATURE:
<223> OTHER INFORMATION: primer

<400> SEQUENCE: 25
agctgcgagg tcaacggcta agcgccagtt tggtgaatcc 40

<210> SEQ ID NO 26
<211> LENGTH: 40
<212> TYPE: DNA
<213> ORGANISM: Artificial Sequence
<220> FEATURE:
<223> OTHER INFORMATION: primer

<400> SEQUENCE: 26
aactggcgct tagccgttga cctcgcagct ggcacgggat 40

<210> SEQ ID NO 27
<211> LENGTH: 40
<212> TYPE: DNA
<213> ORGANISM: Artificial Sequence
<220> FEATURE:
<223> OTHER INFORMATION: primer

<400> SEQUENCE: 27
cgactctaga ggatccgcca agggatccgt gagatcgcat 40

<210> SEQ ID NO 28
<211> LENGTH: 43
<212> TYPE: DNA
<213> ORGANISM: Artificial Sequence
<220> FEATURE:
<223> OTHER INFORMATION: primer

<400> SEQUENCE: 28
acctgactcg accggctcgg agatgtgttg gatgtgattc tgc 43

<210> SEQ ID NO 29
<211> LENGTH: 40
<212> TYPE: DNA
<213> ORGANISM: Artificial Sequence
<220> FEATURE:
<223> OTHER INFORMATION: primer

<400> SEQUENCE: 29
gcttgttgac ctcgccaatc atatcacgct cgctttggcc 40

<210> SEQ ID NO 30
<211> LENGTH: 28
<212> TYPE: DNA
<213> ORGANISM: Artificial Sequence
<220> FEATURE:
<223> OTHER INFORMATION: primer

<400> SEQUENCE: 30
ccggtcgagt caggtattca tatcatcc 28

<210> SEQ ID NO 31
<211> LENGTH: 25
<212> TYPE: DNA
<213> ORGANISM: Artificial Sequence
<220> FEATURE:
<223> OTHER INFORMATION: primer

<400> SEQUENCE: 31
gcgaggtcaa caagcctcaa accct 25

<210> SEQ ID NO 32
<211> LENGTH: 40
<212> TYPE: DNA
<213> ORGANISM: Artificial Sequence
<220> FEATURE:
<223> OTHER INFORMATION: primer

<400> SEQUENCE: 32
cggtacccgg ggatcagcgc agaccaatgc cagaggagaa 40

<210> SEQ ID NO 33
<211> LENGTH: 40
<212> TYPE: DNA
<213> ORGANISM: Artificial Sequence
<220> FEATURE:
<223> OTHER INFORMATION: primer

<400> SEQUENCE: 33
ccgatctgaa ttgacgcgcg agttgcgcga tgaaatttat 40

<210> SEQ ID NO 34
<211> LENGTH: 40
<212> TYPE: DNA
<213> ORGANISM: Artificial Sequence
<220> FEATURE:
<223> OTHER INFORMATION: primer

<400> SEQUENCE: 34
tcggcgttca cttatcttcc ccaagaccgt aagtcggggc 40

<210> SEQ ID NO 35
<211> LENGTH: 40
<212> TYPE: DNA
<213> ORGANISM: Artificial Sequence
<220> FEATURE:
<223> OTHER INFORMATION: primer

<400> SEQUENCE: 35
cgactctaga ggatcaaccg tcgatcagaa ggagcgcaat 40

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
gtcaattcag atcggctgcc 20

<210> SEQ ID NO 37
<211> LENGTH: 20
<212> TYPE: DNA
<213> ORGANISM: Artificial Sequence
<220> FEATURE:
<223> OTHER INFORMATION: primer

```
<400> SEQUENCE: 37

ataagtgaac gccgagtcag                                                 20


<210> SEQ ID NO 38
<211> LENGTH: 813
<212> TYPE: PRT
<213> ORGANISM: Talaromyces cellulolyticus

<400> SEQUENCE: 38

Met Tyr Ser Ala Phe Leu Leu Leu Leu Ala Ser Ala Thr Pro Ile Val
1               5                   10                  15

Ser Ala Gln Ser Ala Ser Trp Ser Ala Ala Tyr Ser Lys Ala Thr Ala
            20                  25                  30

Ala Leu Ser Lys Leu Ser Gln Asn Asp Lys Ile Gly Met Val Thr Gly
        35                  40                  45

Val Gly Trp Gly Lys Gly Pro Cys Val Gly Asn Thr Ala Ala Pro Ser
    50                  55                  60

Gly Ile Ser Phe Pro Ser Leu Cys Ile Gln Asp Ser Pro Leu Gly Val
65                  70                  75                  80

Arg Tyr Ala Asn Pro Val Thr Ala Phe Pro Ala Gly Thr Asn Ala Gly
                85                  90                  95

Met Thr Trp Asp Arg Thr Leu Met Asn Gln Arg Gly Ala Ala Leu Gly
            100                 105                 110

Ala Glu Ser Lys Gly Leu Gly Val His Val Gln Leu Gly Pro Val Ala
        115                 120                 125

Gly Pro Leu Gly Lys Ile Ala Gln Gly Gly Arg Gly Trp Glu Gly Phe
    130                 135                 140

Gly Thr Asp Pro Tyr Leu Ser Gly Val Ala Met Ile Glu Thr Ile Ser
145                 150                 155                 160

Gly Met Gln Ser Ser Gly Thr Gln Ala Cys Ala Lys His Tyr Ile Gly
                165                 170                 175

Asn Glu Gln Glu Leu Asn Arg Glu Ser Met Ser Ser Asn Ile Asp Asp
            180                 185                 190

Arg Thr Leu His Glu Leu Tyr Leu Trp Pro Phe Ala Asp Ala Val Arg
        195                 200                 205

Ala Asn Val Ala Ser Val Met Cys Ser Tyr Asn Gln Ile Asn Gly Thr
    210                 215                 220

Phe Ser Cys Glu Asn Glu Glu Ser Met Thr Gly Ile Leu Lys Thr Glu
225                 230                 235                 240

Leu Gly Phe Pro Gly Tyr Ile Met Ser Asp Trp Asp Ala Gln His Thr
                245                 250                 255

Thr Val Thr Ser Ala Asn Ser Gly Leu Asp Met Thr Met Pro Gly Ser
            260                 265                 270

Asp Tyr Ser Asp Thr Pro Ser Ser Val Leu Trp Gly Gln Asn Leu Ala
        275                 280                 285

Asn Ala Ile Ser Ser Gly Gln Val Ala Gln Ser Arg Leu Asp Asp Met
    290                 295                 300

Val Thr Arg Ile Leu Ala Ala Trp Tyr Leu Val Gly Gln Asp Gln Gly
305                 310                 315                 320

Phe Pro Ala Val Ala Phe Asn Ser Trp Thr Gly Gly Gln Ala Ser Val
                325                 330                 335

Asn Val Thr Ser Asn His Asn Gln Val Ala Arg Ala Val Ala Arg Asp
            340                 345                 350
```

```
Ser Ile Val Leu Leu Lys Asn Thr Asn Ser Thr Leu Pro Leu Asn Lys
        355                 360                 365

Pro Ser Ser Ile Ala Ile Ile Gly Thr Asp Ala Gln Thr Asn Pro Ser
    370                 375                 380

Gly Pro Asn Ala Cys Thr Asp Arg Gly Cys Asp Thr Gly Thr Leu Ala
385                 390                 395                 400

Met Gly Trp Gly Ser Gly Thr Cys Gln Phe Pro Tyr Leu Thr Asp Pro
                405                 410                 415

Leu Thr Ala Ile Lys Thr Arg Ala Ala Ser Asp Gly Thr Thr Ile Thr
            420                 425                 430

Thr Ser Ile Ser Asp Asn Gly Ser Ala Gly Ala Ser Val Ala Gln Ser
        435                 440                 445

Ala Glu Tyr Ala Ile Val Phe Ile Asn Ser Asp Ser Gly Glu Gly Tyr
    450                 455                 460

Ile Thr Val Glu Gly Val Ala Gly Asp Arg Asn Asn Leu Asp Pro Trp
465                 470                 475                 480

His Ser Gly Asn Ala Leu Val Gln Ser Val Ala Ala Val Asn Lys Lys
                485                 490                 495

Thr Ile Val Val Ile His Ser Val Gly Pro Val Ile Leu Glu Thr Ile
            500                 505                 510

Leu Ala Gln Pro Asn Val Val Ala Val Val Trp Ala Gly Ile Pro Gly
        515                 520                 525

Gln Glu Ser Gly Ser Ala Leu Thr Asp Ile Leu Tyr Gly Ser Thr Ala
    530                 535                 540

Pro Ser Gly Lys Leu Thr Tyr Thr Ile Ala Lys Gln Ala Ser Asp Tyr
545                 550                 555                 560

Gly Thr Ala Val Val Ser Gly Ser Asp Asn Tyr Pro Glu Gly Leu Phe
                565                 570                 575

Ile Asp Tyr Arg His Phe Asp Lys Ser Asn Ile Glu Pro Arg Tyr Glu
            580                 585                 590

Phe Gly Tyr Gly Leu Ser Tyr Thr Thr Phe Gly Tyr Thr Asn Leu Ala
        595                 600                 605

Ile Asp Ile Thr Val Ser Thr Gly Pro Thr Thr Gly Gln Ile Val Pro
    610                 615                 620

Gly Gly Pro Ser Asp Leu Phe Glu Ser Val Gly Thr Val Thr Val Gln
625                 630                 635                 640

Val Ala Asn Thr Gly Ser Val Ala Gly Ser Glu Val Ala Gln Leu Tyr
                645                 650                 655

Ile Gly Leu Pro Ser Ser Ala Pro Ser Ser Pro Pro Lys Gln Leu Arg
            660                 665                 670

Gly Phe Asp Lys Leu Ser Leu Ala Ala Gly Ala Ser Gly Thr Ala Thr
        675                 680                 685

Phe Asp Leu Thr Arg Arg Asp Leu Ser Tyr Trp Asp Val Ser Lys Gln
    690                 695                 700

Lys Trp Val Val Pro Ser Gly Ala Phe Thr Val Tyr Val Gly Ala Ser
705                 710                 715                 720

Ser Arg Asp Ile Arg Leu Gln Gly Thr Phe Thr Pro Gly Gly Ser Ser
                725                 730                 735

Thr Thr Ser Thr Ile Thr Ser Ser Lys Thr Ser Thr Thr Ile Ser Thr
            740                 745                 750

Ser Val Thr Thr Ser Ser Ser Thr Thr Ala Lys Thr Thr Thr Thr Ser
        755                 760                 765

Ser Thr Thr Ser Ser Ala Gly Pro Thr Gln Thr Pro Tyr Gly Gln Cys
```

```
    770                 775                 780

Gly Gly Gln Gly Trp Thr Gly Pro Thr Val Cys Ser Ser Gly Trp Thr
785                 790                 795                 800

Cys Lys Val Thr Asn Gln Trp Tyr Ser Gln Cys Leu Gln
                805                 810


<210> SEQ ID NO 39
<211> LENGTH: 40
<212> TYPE: DNA
<213> ORGANISM: Artificial Sequence
<220> FEATURE:
<223> OTHER INFORMATION: primer

<400> SEQUENCE: 39

tcgagctcgg taccccgagg tctgtctaaa aaatctagca                           40


<210> SEQ ID NO 40
<211> LENGTH: 40
<212> TYPE: DNA
<213> ORGANISM: Artificial Sequence
<220> FEATURE:
<223> OTHER INFORMATION: primer

<400> SEQUENCE: 40

ccgatctgaa ttgactttga tatgttcttc tcttgaacct                           40


<210> SEQ ID NO 41
<211> LENGTH: 40
<212> TYPE: DNA
<213> ORGANISM: Artificial Sequence
<220> FEATURE:
<223> OTHER INFORMATION: primer

<400> SEQUENCE: 41

tcggcgttca cttatggtac gggagatgaa cgttgggaat                           40


<210> SEQ ID NO 42
<211> LENGTH: 40
<212> TYPE: DNA
<213> ORGANISM: Artificial Sequence
<220> FEATURE:
<223> OTHER INFORMATION: primer

<400> SEQUENCE: 42

ctctagagga tcccctgaaa gacgagaacg acataaagcg                           40


<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43

gtcaattcag atcggctgcc                                                 20


<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44

ataagtgaac gccgagtcag                                                 20
```

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
gtccttttat aaccgagcca 20

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
ctggaacata caagtccggc 20

<210> SEQ ID NO 47
<211> LENGTH: 4509
<212> TYPE: DNA
<213> ORGANISM: Talaromyces cellulolyticus

<400> SEQUENCE: 47
atgtcgagaa gaatacggaa ccctgattcc gcaggctcga gtcaaaccct aagtaattca 60
ccggtaccaa tagccgccga atccggcacg gaacctgtgt acctaggtcc gtatcgaata 120
gcgaagtttt ccgtctattc ttcgaatttt gtatacatgc ttaccttggc tcaaaggtac 180
tcacaaagtc cgaagaataa attatagaac cgatgtgaaa cggggacagt ttggcaaccc 240
cttgtactat gtacattgta tggatctcgt ctcgactctc gagacgaggg tttcgtacca 300
accaaagact caaaacttgg ggtaactaag cgatcggctg cgtagtactc catactccat 360
aaataccccg gtgaattcgc ctcttgccca tggaatgagc gagaatttac ccttggagtc 420
atcgcggtaa atgactcaca tatcatgtct gccttcactc tcctcaacct ttgaaattcc 480
ggttaatgtt aaggcgaggt gtcctctacg gaatggcttt gtagatttga gataagacta 540
cgccgtaact taagggatcc acatactcca tattgatagt ctcaggaccg agatagtctg 600
gagtaacccc gtacccaatc aacgtcctca gactcgccac ctggttacaa tatttcggtg 660
cttgtgccga tatacctccg ttgcgtgagc cttgatagcc aacaagaaat gattcaaaat 720
taagatttga gaaaatccgg agtacgcagt gcctgcagtg taaaaaataa tgtatttacc 780
taatgccaat atgtcgatgc caaagtacta ctagcaaaga cactagatat gcagcaaact 840
cgatgtttag gtacatgtaa ccatatcctg ggtcaggta cgaacgccat caattaatct 900
cgtaaactag ctgtcacacg acagtatcat ttgatagttc caatgttcca tgctcccccct 960 caaatgtcac tggatgatac gaatttggct gtgacttgaa cagatagacg gaaaacagtc 1020
cgatcattat ccggagtacg catgtacgag atagtctggg gatcctcggc tgccccgatt 1080
ggggttagtg cgggtttcct tatcttgata cgccgtctgg aggcgcaggt gattgttacg 1140
gtgtgttccg tgatagataa gttagacatc cgataataac ctatcttcta gatagacggc 1200
aggtacgtat gtagatagat agatgacaca gtcataagac agttttattt accatacata 1260
gtatagtcat ttgacaaaca cttgatgact atgagcagta agtccagaca agagcataga 1320
ctagaaatga tgtgatcatc aataggtacg gagtcgtacc acccccggat tatcttggct 1380

```
ggcttagtca cgcccaaaca gacggtgacg gatgagacac aagcaaagag cgacattccg   1440
aagaattctc gtgacggaaa cgagaatgcc gccggcgctg atagggggaa attttatctt   1500
ttccctttct gacattcagt gtttacaata caatacggaa ttacggaacc ccggttttcg   1560
caaccggtgg aattacctaa tgggtgacct gaatttatta gataacgatg aacaatttgt   1620
tggatcttcc gtagatcgat ttggacttga taggtgcttc caaggttgtt gctgctcaca   1680
tggtcgcttg cgttatctgc ctacagaatg aggaagatgt attccgcacg tactccggtc   1740
gcgacagata tgcgacgatt gcaatatgta ctacatagtt agtacataca actctagact   1800
agactctata ttatgtagag tgtaagagaa aaagaaagaa gataacggca gggtctattt   1860
gattgcgcta taatatgcgc cgctgtatgg ttccccagat ctgcgtgaga tatcacctca   1920
tcctatcatc attccaggtc aaagtctcgt catcatgaat tggtattatt acccagtacg   1980
taaaccacgt atcgaggcgt atcggtgtat taaagataga gctactgcat tggctctagt   2040
cctatctttg ccccggaatc cggcccgtgg atgacgatat gatgctgttt gtccttcagc   2100
taaacacgga cgatctctta cagggtgcgg ttaattatta aggatataat tctaatcaac   2160
gactctggct gtgctatatt aacaatgtct tctaagtggt catgatgtgt acgtacttcg   2220
tacacatgct acatgcaatc gagtacgtaa ctccagatct gcgccgtacc cgcgataccc   2280
gggccatcat gcaaatgtaa ccgcttggaa cacgcactgc agtgcataaa agccacagcc   2340
tcgcttccca atccggttta gacgcgtttt gtcttgctgt tttgggagca gccagacccc   2400
acattccact aacccactct ttttcagcgc ttattctcgt aagattcgta cgaaaaatac   2460
atctgcccac actatccacc agctcggcca ctcttcggtg agaacgctgc catgagaaaa   2520
aaatctgcga ctctgcaaca gagtgaggca cggctgaacc gagctgattg tcaccctttg   2580
cccaatgccc agacagccca gacagcccag acagcccaga cagcccagac agcccagaca   2640
gcccagacag ccagtgcttg gttaattttt actaagggta aaaacctaaa aaaaagaaac   2700
gaaaaaaaaa aaaaaaaact tttctttttt gccccccaat cacttggccg acagtcaaag   2760
ggttccccca cacggtactc cgtacttgct acgtacacta actaaagaaa aaatctcctg   2820
attgagtctg tgtctgtctg tcgctgctaa actcggataa ccccccgttc ccgatcaccc   2880
gtcgaaaaga gcagcagcca tttaacattt ttcccctcca ttcctccttc ttggaacttt   2940
ccctccctcc ctcatcctta catctccctg cgtgcgcgcc tgcctgccta cttacactgc   3000
cactccccag attttctttc tcttgtttct tctccagact ttctttcctc ctccacctcg   3060
cctcaccaca ccaccaccac cactcaccac gccaacaaca ccgcactacc actactgctt   3120
caaagatcga tcaggccatt atcaaggagg atcgacgtct tattccatcg accaccctgt   3180
tgatcacctc ggctggagcg ctcgactccc tggcttcctt ccccagctta tttaaacccg   3240
tcacccgcca ggtctcttca catgtcaccg tcatcttcgt cagtgggttt ttccaatctg   3300
ctgaacccac agtcagactc tgtcgagcct acggataaca catcttcacc tgctaccacc   3360
actaccaccg gcacagactc caactcagac aaggaaatgg cgtcctctgt cagtctgctc   3420
ccaccactca tgaagggtgc ccgccccgcc gcggaggaag tgcgacagga cctccctcgt   3480
ccatacaagt gtcctctttg cgatcgtgct ttccatcgtc tagagcacca aactcgtcac   3540
attcgtactc acaccggcga gaaaccccat gcctgccagt ttccaggctg cacgaaacgg   3600
ttcagtcgtt cagatgaatt gactcgtcac tcgcgcattc acaacaaccc caactcgaga   3660
agaagtaaca aagctcagca tattgctgcg gctgcggcgg ccggtcagga ttcgggtatg   3720
cttaacgctg ctgcctcgat gatgcctcct ccaagcaaac ccattactcg ctcggctcca   3780
```

gtgtctcagg tcggatctcc ggatgtgtct cctccgcact cttacaccaa ctacacctcg 3840
catttgcggg cgggtctggg tccttattca cgcaacagcg accgtgcttc atctggtatg 3900
gatattaatt tgctcgcgac tgctgcttca caagtcgagc gcgatcacta cggaggctcg 3960
tctcgtcatt accctttcag ctctcgatac tcgggtactc ctggacgtct accgtcgctt 4020
tccgcctatg ccatttctca gagcatgagc cggtcgcatt ctcacgagga tgaggacaac 4080
tacggacatc accgggttaa gcgctctcgt cctaactcac caaactcgac tgcgccatcc 4140
tcgcctacat tctctcacga ttcattgtcg cctacccccg atcacactcc tcttgcaacc 4200
ccagcacact cgcctcgttt gcgtccttat ggagccgcag atttgcaatt accttccatc 4260
cgtcatttgt cgttacacca cactcccgca ctcgcaccaa tggagcctca agccgaggga 4320
cctaatgttt acaaccccgg tcagcaccac ggtggaccca gcatcacgga catcatgagc 4380
aggcccgacg gcacccagcg taagcttcct gttccgcaag tacccaaaat cccggtgcag 4440
gacatgttgg caccgaacgg atattcctcc aacactccgt ccgtcaacgg ttccgtgatg 4500
gagttataa 4509

<210> SEQ ID NO 48
<211> LENGTH: 2442
<212> TYPE: DNA
<213> ORGANISM: Talaromyces cellulolyticus

<400> SEQUENCE: 48
atgtattccg catttctttt gctgctggct tcggccacgc ctatagtcag cgcccagtca 60
gcttcttggt ccgcagccta cagtaaagcc acggctgctt tgagcaaact ctctcaaaat 120
gacaaaattg gtatggtgac aggcgtggga tgggggaaag gtccatgtgt tggaaacact 180
gccgcgccat ctggaatctc gtttccatca ctctgtattc aagatagtcc cctaggcgtt 240
cgttatgcga accccgtcac agcgtttccg gcaggcacga atgctggaat gacctgggat 300
cggacgttga tgaaccagag aggtgccgct cttggtgcag aatccaaggg gctaggtgtc 360
catgttcagt tagggcctgt ggcaggtccc ctaggaaaga tcgcgcaggg tggtcgtggt 420
tgggaaggat ttggaacgga tccatacctc agtggtgttg ctatgattga gactatttca 480
ggtatgcaga gttcgggtac tcaggcatgc gcgaagcact atattggcaa cgagcaagag 540
ctaaacaggg aatcgatgag ttctaatatt gatgatcgta ctttgcacga gctttacctg 600
tggccctttg ccgatgccgt ccgtgccaat gttgccagtg tgatgtgctc ctacaaccaa 660
atcaatggaa cattttcctg tgagaatgaa gaatcgatga caggtattct gaagacagag 720
ctcggctttc caggatacat aatgtctgac tgggatgcac agcacaccac agttactagt 780
gctaactctg gacttgatat gacgatgcca ggtagtgatt atagtgatac gccgagtagt 840
gtcctttggg gtcaaaatct ggccaatgcc atctcaagtg gccaagttgc ccagtcgcgt 900
ctcgacgata tggtgactcg aattttggct gcttggtatt tggttgggca ggatcaaggc 960
ttccctgcgg tggcctttaa ctcttggacc ggtgggcaag caagtgttaa tgtcacatca 1020
aaccacaacc aagttgcccg tgcagtcgct cgcgattcta tcgttttgct taaaaatacc 1080
aatagcacgc ttccgttgaa caaaccatcg agcattgcta ttattggcac tgacgcccag 1140
acaaaccctt ccgggccaaa cgcttgtact gatcgtggtt gtgatactgg aactttggct 1200
atgggttggg gtagtggaac ttgccaattt ccatatctca cagatcctct aacagctatt 1260
aaaactcgag ctgccagcga cgggactacg atcacgacga gcattagtga caatggcagt 1320

```
gcgggagcct cagttgctca aagcgccgag tatgcaatcg ttttcatcaa ttcagactct   1380

ggcgaagggt acataacagt cgaaggcgtc gctggtgacc gcaacaatct cgacccatgg   1440

cacagtggca atgcattagt gcaatccgtc gccgcagtca acaagaagac gattgtcgtc   1500

attcatagcg tcgggccggt cattcttgaa accatattgg cgcaacctaa cgttgtggcc   1560

gtagtatggg ctggcatacc aggacaagag agcggctcag ccctcaccga tattctctat   1620

gggagtacag ctcccagtgg aaagctaacg tacacgattg ccaaacaggc ttccgattac   1680

ggcactgcag tcgtcagtgg tagcgacaat tatccagagg gacttttcat tgattaccga   1740

cacttcgaca aaagcaatat tgaacctcga tatgaattcg gctatggact gtcatataca   1800

acctttggtt acacgaattt ggcaattgat attacggttt cgacgggccc aactactggt   1860

caaatagttc ctggtggacc ttctgatctt tttgagtctg ttggaaccgt tacggtacag   1920

gtcgcaaaca caggcagcgt tgcaggctca gaagttgcac aactctatat tgggctgcca   1980

tcgtcagcac cgtcatcacc accaaaacag ttgcgtgggt ttgataagct ttctctcgct   2040

gctggcgcta gcgggaccgc aacgttcgat ttgacacgaa gagatttgag ttactgggat   2100

gtatcaaagc agaagtgggt ggttccaagc ggagcattta ccgtatatgt tggggcatcg   2160

agtagggata ttaggttgca ggggacattt acgcccggag gtagctcgac cacttcgact   2220

ataacttcct ctaagacttc tactactatc agcacttctg ttaccaccag tagcagtacg   2280

acagctaaaa ccaccacaac tagctcgacc acgtcatctg ccgggccaac acagaccccg   2340

tatggacagt gtggtggaca gggttggacc ggccctacag tgtgttcatc tggctggact   2400

tgcaaggtaa cgaatcaatg gtattctcaa tgcctacaat ag                       2442
```

<210> SEQ ID NO 49
<211> LENGTH: 1354
<212> TYPE: DNA
<213> ORGANISM: Talaromyces cellulolyticus

<400> SEQUENCE: 49

```
ctcgtgaaag ctgccctcac aatgatcgtc aagatgacgt agtttgactg ggtcgttcct     60

ggataagggt tagggtaaat agggctcaaa gtaccacgtg agtgtggaaa gataagccct    120

aaccctaagg tcgtgtcgga caaaaattat cacttgacca aaattggaga tccccttaat    180

ggagcttttt ggtaatggtt tgtatagggt tatgtgacgt ccgtatcaca tgatttttat    240

cccaacaggt cgatccccct cttatagtta atggacaaca tataagtacg tagcatctta    300

gatagttcgt cagcgtcaac tgaccaaagt ccccgtgttt cattttaatt tgtcagactg    360

caagagtctc gaaacataaa aagatcgaaa gttttgcctt attaggctat gagcatgaat    420

gtcggaacaa tgccgttgag gctattccca atttcggaaa tatgtatctt cattgctgtc    480

gacttgacga cagtcgataa aaggctcatc cggatagata agccagatca ctcattatgc    540

caatttctcc ggtgtctgaa aacgtatact acatacgtaa ctgatcttcg tggttgaaag    600

agtgtttctt ctcattctca tctgccgatg ccgagccaat tggaacaaac cccgcatatg    660

gtcctgaata tcaatcgcgg agatgcggag agtgagggag caacacaatt ttaaattagt    720

cagttttctc atgttctccg caatcttgca ggcttgggtc tggtaggttt atctctctct    780

tttcacaaca aggttgggcc attgtcagct tagcaagcgc gcagcaaagg gtgtcggtca    840

atgttcatgt cctccgcggt cactacaaaa cagcacgtgg ggaatgttgc tttccctgtt    900

gatgttcatg tgttgtcatt cccggcaaat cgactccaat taatatggta ggctcctgca    960

taatgcaagt ccttgagatg cagcttccgg cagatggacg tatagatcag ggactttgag   1020
```

```
gggctaaaac acttacccga gctaaaacat accataattt cgtttaatga ctttcgtctg   1080

gatggcagag gctgaaggtc gattatgagt gaaattggta tgaagccaca tacgccgata   1140

ctgtaacgct gtgccttcat ccgccttcta tcgcgccccg acattccgcg gtaccgcgat   1200

tatgaagaaa aacactcgta atgatgagga gatagttctt agctcttatt atttttgtct   1260

agctatggaa tgcaagttta gcactatata atggtggtgt ttcccttgaa gaattaggca   1320

ctatcaaccg caacagtcag aagcaatcga caca                               1354
```

<210> SEQ ID NO 50
<211> LENGTH: 1100
<212> TYPE: DNA
<213> ORGANISM: Talaromyces cellulolyticus

<400> SEQUENCE: 50

```
tgctatgcag ttgatgctac tgtgttctaa aataattgat agggttaggg tcgggtataa     60

ggcgatgcaa tgtatcaatt atcacgagaa ataatgcaga aaaacacaat tccccgtatc    120

tgttgattct taaacaatct gatcaccaat ttgtagaaag aaacgattat aaggtgccat    180

ggtaatgctg gagtttacac aggatactac ttgttctgtt cattacaatg aaccgtaatt    240

gcattctgtt ttgaccactc aacaaatcct acacaaaagt aagtggactt cagtgctcgc    300

tctacgcaag taaatacttg gcatatatgg cctcgtatat tcttacaatg aggtaaattc    360

cgatagatta ctgcccaact agtcaatctt aaatccttaa gagatacagg gggaggcgga    420

agtacctgaa accacgtaat aagacgttca gggtcatgtg aatgtatgta gtatccatgt    480

ccaatacaat tgataatagt atccagtatt atatctcatt caggtaagcg ccacgcgatt    540

cttcagatct acttaactgc cgactcgcca aacgaaacaa cgtttattcg tgaccccaga    600

aaatcaccgc ggagttgcgg aggaccagtt tgtacaatgc accgaaccaa gcgttggtca    660

tttttctgga aatgggccaa acgttagaag tgattggtca gagctacatc tgaaggtgaa    720

gcaatttccg gtatgcatac atgacagcaa gcttacctac caagaccaag ttattcccca    780

gcatttgccc catacttggc tttaatattg tgggatagca aacaatatcc acaacactga    840

tgataactaa actacaaatc tgacgttact tcagactact cacgtgtcaa aagcagttag    900

cgaggatcaa gtcttttagt ctggtcatta acaaacgcaa tttcgcaacc cgataatccg    960

cgatgataat atagcgactc caaggtcgta tttatattca atcaattccc cccaatttgg   1020

aatggatttt tggaatcatc gcatgccagg acaatcagtg aaacagtgac aaagtgaagc   1080

ttcttgatca tttagcaact                                               1100
```

<210> SEQ ID NO 51
<211> LENGTH: 26
<212> TYPE: PRT
<213> ORGANISM: Talaromyces cellulolyticus

<400> SEQUENCE: 51

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln
            20                  25
```

<210> SEQ ID NO 52
<211> LENGTH: 24
<212> TYPE: DNA
<213> ORGANISM: Artificial Sequence
<220> FEATURE:

<223> OTHER INFORMATION: primer

<400> SEQUENCE: 52
cgtctcgggt ccaatcgagt ttcc 24

<210> SEQ ID NO 53
<211> LENGTH: 51
<212> TYPE: DNA
<213> ORGANISM: Artificial Sequence
<220> FEATURE:
<223> OTHER INFORMATION: primer

<400> SEQUENCE: 53
attggacccg agacgaattg tgaatttctt cgccctcatc ccttgggatt c 51

<210> SEQ ID NO 54
<211> LENGTH: 37
<212> TYPE: DNA
<213> ORGANISM: Artificial Sequence
<220> FEATURE:
<223> OTHER INFORMATION: primer

<400> SEQUENCE: 54
gaagttacta atagagcgat tagcagaagt ctttccg 37

<210> SEQ ID NO 55
<211> LENGTH: 51
<212> TYPE: DNA
<213> ORGANISM: Artificial Sequence
<220> FEATURE:
<223> OTHER INFORMATION: primer

<400> SEQUENCE: 55
tctattagta acttcgagtt ttccgaaggt taccaatcca gatttggtgt c 51

<210> SEQ ID NO 56
<211> LENGTH: 45
<212> TYPE: DNA
<213> ORGANISM: Artificial Sequence
<220> FEATURE:
<223> OTHER INFORMATION: primer

<400> SEQUENCE: 56
cggtacccgg ggatccacac gagttgctac aacctcaatt acctg 45

<210> SEQ ID NO 57
<211> LENGTH: 42
<212> TYPE: DNA
<213> ORGANISM: Artificial Sequence
<220> FEATURE:
<223> OTHER INFORMATION: primer

<400> SEQUENCE: 57
cgactctaga ggatcgtcat aggtggcccg tttaaagaca gc 42

<210> SEQ ID NO 58
<211> LENGTH: 36
<212> TYPE: DNA
<213> ORGANISM: Artificial Sequence
<220> FEATURE:
<223> OTHER INFORMATION: primer

<400> SEQUENCE: 58
ggttgagtgt tgttcgagag tgaacggcag agggtg 36

```
<210> SEQ ID NO 59
<211> LENGTH: 25
<212> TYPE: DNA
<213> ORGANISM: Artificial Sequence
<220> FEATURE:
<223> OTHER INFORMATION: primer

<400> SEQUENCE: 59

caatcatatc acgctcgctt tggcc                                          25


<210> SEQ ID NO 60
<211> LENGTH: 26
<212> TYPE: DNA
<213> ORGANISM: Artificial Sequence
<220> FEATURE:
<223> OTHER INFORMATION: primer

<400> SEQUENCE: 60

gaacaacact caaccctatc tcggtc                                         26


<210> SEQ ID NO 61
<211> LENGTH: 28
<212> TYPE: DNA
<213> ORGANISM: Artificial Sequence
<220> FEATURE:
<223> OTHER INFORMATION: primer

<400> SEQUENCE: 61

aggctttaca ctttatgctt ccggctcg                                       28


<210> SEQ ID NO 62
<211> LENGTH: 1589
<212> TYPE: DNA
<213> ORGANISM: Talaromyces cellulolyticus

<400> SEQUENCE: 62

atgaagggcg tcctcagcct ttcgctgctg ccgttgttga cggttgcgtc accggtgatg      60

ccgcgcacca tccacaacga cgctgctccc attctctctt cgtccaacgc cgttgaggtc     120

ccagattcat atatcattgt ctttaaagac catgtagatt ctgcttctgc cgcagcccat     180

cataactggg tgcaagacat tcacagccaa cacaccgagc tccgaaagcg gtctcaattc     240

ccattcgctg acaatgcctt tgccggtctc aaacacactt ttgacattgc cggcagcttc     300

cttggttact caggacactt cgaagagaat gtcattgagg ccattcgccg acaccccgat     360

gtgagttatc cgcacgtgcc ctactcctaa ggcaatgact aatacgcatc tccacctata     420

ggttgattac atcgagaagg attctcttgt ccacaccatg gaagatcccg cccttgagaa     480

gaacgcccca tggggtttgg ctcgtatttc gcaccgtgag agcttgagct tcggaagctt     540

caacaagtac ttgtacgctg ccgacggcgg tgaaggtgtt gacgtttatg tcattgacac     600

tggtaccaac atcgaccacg tcgacttcga gggtcgtgct tcctggggca agaccatccc     660

cactgacgat gaggatgttg atggcaatgg tcacggtact cactgctccg gaactattgc     720

gggcaagaag tacggtgttg ccaagaaggc caatgtctac gctgtcaagg tcttgaagtc     780

taacggttct ggaaccatgt ccgatgtcgt tcagggtgtc gaatgggctg ctactcagca     840

catcaagaag gtcaaggacg ccaaggccgg aaaagccaag ggcttcaagg gtagcgctgc     900

gaacatgagt ctcggtggtg gcaagtccgt cactcttgac aaggctgtca atgctgctgt     960

tgatgctggt atccacttcg ctgtcgctgc tggcaacgac aacgccgact cctgcaacta    1020

ctcccctgcc gccgctgaga aggccgtcac cgtcggagcc tcgaccttgg ccgatgagcg    1080
```

```
tgcttacttc tccaactacg gcaagtgcaa cgacatcttt gctcctggtc tgaacattct   1140

ctctacctgg atcggcagca agtacgccgt caacaccatc tccggtacct ccatggcttc   1200

tcctcacatt gctggtcttt tggcctactt cctctctctc cagcctgcca gtgactccgc   1260

cttcgctgtt gccgagatta ctcccaagaa gttgaaggag aacctcattg ctattggtac   1320

ccagggcgct cttactgatg ttccctctga caccactaac gtaagttgac tctgttagtc   1380

tttcaatgca ttatcaacta acaactgtgt catagattct cgcctggaac ggtggtggct   1440

cagccaacta caccgacatc attgcccaag gtggttacaa gaccaagaca ctcagcaacg   1500

aagttgacga attgatcaac aagttggagg tcgtgaacga ggaactcggt gccatctaca   1560

gccacatcaa ggatgccatt gccgcataa                                      1589
```

```
<210> SEQ ID NO 63
<211> LENGTH: 40
<212> TYPE: DNA
<213> ORGANISM: Artificial Sequence
<220> FEATURE:
<223> OTHER INFORMATION: primer

<400> SEQUENCE: 63

cggtacccgg ggatcttggg gcacagagac aacagggtca                            40


<210> SEQ ID NO 64
<211> LENGTH: 40
<212> TYPE: DNA
<213> ORGANISM: Artificial Sequence
<220> FEATURE:
<223> OTHER INFORMATION: primer

<400> SEQUENCE: 64

agatagggtt gagtgagata gcgtgagcac actgagcagg                            40


<210> SEQ ID NO 65
<211> LENGTH: 40
<212> TYPE: DNA
<213> ORGANISM: Artificial Sequence
<220> FEATURE:
<223> OTHER INFORMATION: primer

<400> SEQUENCE: 65

aaagtgtaaa gcctgcaaca cgctacctct tccacagtag                            40


<210> SEQ ID NO 66
<211> LENGTH: 40
<212> TYPE: DNA
<213> ORGANISM: Artificial Sequence
<220> FEATURE:
<223> OTHER INFORMATION: primer

<400> SEQUENCE: 66

cgactctaga ggatcgagct gattgagcat gctaacgcag                            40


<210> SEQ ID NO 67
<211> LENGTH: 21
<212> TYPE: DNA
<213> ORGANISM: Artificial Sequence
<220> FEATURE:
<223> OTHER INFORMATION: primer

<400> SEQUENCE: 67

cactcaaccc tatctcggtc t                                                21
```

```
<210> SEQ ID NO 68
<211> LENGTH: 24
<212> TYPE: DNA
<213> ORGANISM: Artificial Sequence
<220> FEATURE:
<223> OTHER INFORMATION: primer

<400> SEQUENCE: 68

caggctttac actttatgct tccg                                          24


<210> SEQ ID NO 69
<211> LENGTH: 490
<212> TYPE: PRT
<213> ORGANISM: Talaromyces cellulolyticus

<400> SEQUENCE: 69

Met Lys Gly Val Leu Ser Leu Ser Leu Leu Pro Leu Leu Thr Val Ala
1               5                   10                  15

Ser Pro Val Met Pro Arg Thr Ile His Asn Asp Ala Ala Pro Ile Leu
            20                  25                  30

Ser Ser Ser Asn Ala Val Glu Val Pro Asp Ser Tyr Ile Ile Val Phe
        35                  40                  45

Lys Asp His Val Asp Ser Ala Ser Ala Ala Ala His His Asn Trp Val
    50                  55                  60

Gln Asp Ile His Ser Gln His Thr Glu Leu Arg Lys Arg Ser Gln Phe
65                  70                  75                  80

Pro Phe Ala Asp Asn Ala Phe Ala Gly Leu Lys His Thr Phe Asp Ile
                85                  90                  95

Ala Gly Ser Phe Leu Gly Tyr Ser Gly His Phe Glu Glu Asn Val Ile
            100                 105                 110

Glu Ala Ile Arg Arg His Pro Asp Val Asp Tyr Ile Glu Lys Asp Ser
        115                 120                 125

Leu Val His Thr Met Glu Asp Pro Ala Leu Glu Lys Asn Ala Pro Trp
    130                 135                 140

Gly Leu Ala Arg Ile Ser His Arg Glu Ser Leu Ser Phe Gly Ser Phe
145                 150                 155                 160

Asn Lys Tyr Leu Tyr Ala Ala Asp Gly Gly Glu Gly Val Asp Val Tyr
                165                 170                 175

Val Ile Asp Thr Gly Thr Asn Ile Asp His Val Asp Phe Glu Gly Arg
            180                 185                 190

Ala Ser Trp Gly Lys Thr Ile Pro Thr Asp Asp Glu Asp Val Asp Gly
        195                 200                 205

Asn Gly His Gly Thr His Cys Ser Gly Thr Ile Ala Gly Lys Lys Tyr
    210                 215                 220

Gly Val Ala Lys Lys Ala Asn Val Tyr Ala Val Lys Val Leu Lys Ser
225                 230                 235                 240

Asn Gly Ser Gly Thr Met Ser Asp Val Val Gln Gly Val Glu Trp Ala
                245                 250                 255

Ala Thr Gln His Ile Lys Lys Val Lys Asp Ala Lys Ala Gly Lys Ala
            260                 265                 270

Lys Gly Phe Lys Gly Ser Ala Ala Asn Met Ser Leu Gly Gly Gly Lys
        275                 280                 285

Ser Val Thr Leu Asp Lys Ala Val Asn Ala Ala Val Asp Ala Gly Ile
    290                 295                 300

His Phe Ala Val Ala Ala Gly Asn Asp Asn Ala Asp Ser Cys Asn Tyr
305                 310                 315                 320
```

```
Ser Pro Ala Ala Ala Glu Lys Ala Val Thr Val Gly Ala Ser Thr Leu
                325                 330                 335

Ala Asp Glu Arg Ala Tyr Phe Ser Asn Tyr Gly Lys Cys Asn Asp Ile
            340                 345                 350

Phe Ala Pro Gly Leu Asn Ile Leu Ser Thr Trp Ile Gly Ser Lys Tyr
        355                 360                 365

Ala Val Asn Thr Ile Ser Gly Thr Ser Met Ala Ser Pro His Ile Ala
    370                 375                 380

Gly Leu Leu Ala Tyr Phe Leu Ser Leu Gln Pro Ala Ser Asp Ser Ala
385                 390                 395                 400

Phe Ala Val Ala Glu Ile Thr Pro Lys Lys Leu Lys Glu Asn Leu Ile
                405                 410                 415

Ala Ile Gly Thr Gln Gly Ala Leu Thr Asp Val Pro Ser Asp Thr Thr
            420                 425                 430

Asn Ile Leu Ala Trp Asn Gly Gly Gly Ser Ala Asn Tyr Thr Asp Ile
        435                 440                 445

Ile Ala Gln Gly Gly Tyr Lys Thr Lys Thr Leu Ser Asn Glu Val Asp
    450                 455                 460

Glu Leu Ile Asn Lys Leu Glu Val Val Asn Glu Glu Leu Gly Ala Ile
465                 470                 475                 480

Tyr Ser His Ile Lys Asp Ala Ile Ala Ala
                485                 490
```

<210> SEQ ID NO 70
<211> LENGTH: 78
<212> TYPE: DNA
<213> ORGANISM: Talaromyces cellulolyticus

<400> SEQUENCE: 70

```
atgtctgcct tgaactcttt caatatgtac aagagcgccc tcatcttggg ctccttgctg      60

gcaacagctg gtgctcag                                                    78
```

<210> SEQ ID NO 71
<211> LENGTH: 1827
<212> TYPE: DNA
<213> ORGANISM: Talaromyces cellulolyticus

<400> SEQUENCE: 71

```
aagtgggtca ccttcatctc tctcctcttc ttgttctcca gcgcctacag ccgtggtgtt      60

ttccgtcgtg acgcacacaa gtccgaagtg gcccatcgct tcaaagacct cggtgaggaa     120

aacttcaagg ctctcgtctt gattgccttc gctcagtact tgcaacagtg ccctttcgag     180

gaccacgtga agctggtcaa cgaagttacc gaattcgcca aaacctgcgt tgctgacgag     240

tctgccgaaa actgcgataa gtctctgcat accttgttcg gcgacaagct ctgtactgtc     300

gctaccctcc gtgagaccta cggagaaatg gccgattgtt gcgccaagca ggagcctgag     360

cgtaatgagt gctttctgca gcacaaggac gacaacccca atttgcctcg gcttgttcgt     420

cctgaggttg acgtcatgtg taccgccttc cacgataacg aggaaacctt cctcaagaag     480

tacctctacg agatcgcaag acgccatccc tacttctacg ctcctgaatt gctgttcttt     540

gccaagcgtt acaaggcagc attcactgag tgttgtcaag ccgctgacaa ggccgcctgc     600

ttgctcccca agttggatga actccgcgat gagggtaagg cctctagcgc caaacagcgc     660

cttaagtgcg cctctttgca gaagttcggt gagagagcct tcaaagcctg ggctgttgct     720

cgtctatccc aacgtttccc taaagccgag tttgctgaag tttccaaact cgtcactgac     780
```

```
ctgacaaagg tccatactga gtgctgccac ggtgacttgt tggagtgtgc tgatgatcgt    840

gccgatttgg caaagtacat ctgcgagaac caggacagca tctcctccaa gttgaaggag    900

tgctgcgaaa agcccttgct cgagaagtcc cactgcattg cggaggtcga gaacgacgaa    960

atgcctgccg acttgccttc tttggctgct gacttcgtcg aaagcaagga tgtctgcaag   1020

aactacgctg aagccaaaga cgtgttcttg ggcatgttct tgtacgagta tgctcgtcgc   1080

caccctgact actccgtggt tcttctcctc cgtctcgcca agacatacga gacgactttg   1140

gagaagtgct gtgccgctgc cgaccctcac gagtgctatg ccaaggtctt cgacgaattc   1200

aagcccttag tcgaagaacc tcagaactta atcaagcaga attgtgagct attcgagcaa   1260

ctcggtgagt acaagttcca gaacgcgtta ctggtccggt acaccaagaa ggttccccaa   1320

gtctccactc ctaccttggt tgaggtctct cgtaacttgg gtaaggttgg aagcaagtgc   1380

tgtaagcacc ccgaagccaa gcgtatgcct tgcgctgaag actacctgtc ggtcgtcttg   1440

aaccaattgt gcgtcttgca cgagaagact cccgttagcg atcgtgttac caagtgttgt   1500

accgaaagct tggttaaccg tcgtccctgc ttctccgctt tggaagtcga tgagacttac   1560

gttcctaagg agttcaacgc cgaaaccttc acctttcacg ctgatatctg cactctgtca   1620

gagaaagagc gtcagatcaa gaagcaaacc gcactcgttg agcttgtcaa gcacaaaccc   1680

aaagccacca aggaacagct caaagccgtc atggacgatt tcgctgcctt cgtcgagaaa   1740

tgctgcaaag ccgacgacaa ggagacgtgc ttcgcggaag agggcaagaa gttggtcgcc   1800

gctagtcaag ctgctcttgg tttgtag                                       1827
```

<210> SEQ ID NO 72
<211> LENGTH: 497
<212> TYPE: DNA
<213> ORGANISM: Talaromyces cellulolyticus

<400> SEQUENCE: 72

```
atcagctttg agtgcagcaa aaatgcttcc gactgtcttc ttatattgat atcatatttt     60

tcaattcact ttgtctcaag tttcaatata tcgagaaaat agtatcaaag atgaactgta    120

ataattccga tatacctata caggtttata gtaaattact ctatttcata atgcgtccat    180

ccgagaagtc tggcggcctt atcagtagtc caaaacgcct ggtttttaga catgtcacct    240

ctaatctccg cttgaggaaa atgcgtccga gcaagttctt tcgacggggt gtcttgggtc    300

gtagttggag atatgatatt tattacttcg aatcctttga tattctcact cttttcaacc    360

gccaaaaggc aagctcttgc cactgcgcga ggattaaccc atccccagag ttgtcgaacc    420

ccagattcat accatttatc gtggtgtctt tttctaacat ctctcaatgg ggcaacctca    480

tgtattctca aacaagc                                                   497
```

<210> SEQ ID NO 73
<211> LENGTH: 2858
<212> TYPE: DNA
<213> ORGANISM: Talaromyces cellulolyticus

<400> SEQUENCE: 73

```
gtcaattcag atcggctgcc gcctgcgccc caggtgacgt cgatgaaagc tgggcctagg     60

tcgtgcatgc ggtccatacg gtcgtataag ttctggacac cttgggcggt ctttgggggg    120

aagtattcga aggaaattcc aggtcggccg gtggccgcct gttcttggag cttttgcccg    180

acatgcatgt tgataggtcg gtcaattgtc tgctttttca atatcttctc ggtatgatgt    240

agcttgcaga acccaagtta tgtagttcaa ttgcaaaatc aagtctgatc aagaccgaaa    300
```

```
ctcaatcccg gagcactgag gttcgcacta attgatcaag ggtacaagaa tgaggggcac    360
aatgaaagca gtcttgaaaa tgacaggcag agaaattgaa agaaaggaga agagaggacc    420
tccgggacag gagaaatgaa agcaacaaaa ccccgaacaa gctggagaga agttaaaggg    480
agcagcttgg tcaccggcaa tggatgctca tcataaaaaa ggaccctaaa cccgttatcg    540
gagtccggag aaatgacgct aattcggatt tggaagtccc cgccaatcgt gggaaattct    600
cgaagcagac aatttgctcg tgacaatcag ccagcaatga gagggagact gaaaaatatg    660
tatttacact caaagaatcc gatactgcta ttaggatcag tgtttttctt ataagcaaat    720
gagcgttgga cgtggaaaat gaggaatcct cagtccctat actcggtcag cgacggaggg    780
gtgcgtgatc ggccaatcac agcctattat tttatcaaca tctgattggc tacttccgat    840
aagagcgaaa tatgcccctc cttgcaattt ttaccatcaa cgctaacagc aacactcaac    900
aaaccattca atcttgatac tcgctcccat tagtcaccac gcaggacaac acaacacgac    960
atcgcatctc agctttgacc attcccgccg caagcgattc gctgtcacaa acgccagata   1020
ccccaacatg gctgcccctc cctccgccga tcaggactac aagaccaatc tgttgtcttt   1080
gctgatagcc aacgatgcgc tcgcatttgg cacgttcaca ttgaaatctg gtcgccagtc   1140
gccgtatttt ttgacctcga gtcgtcttta tactgcgcct ctgctgcgcc aggtgtcggc   1200
cgcgttcgcg aataccatct cgtccccgcc ttttgtgaat atagctgcag atggcagcat   1260
taccccgaac tttgacattg tttttgggta tgttacccta ttattcgtgc gcctgatatg   1320
cgtgtactga tttacttcaa atagccccgc ctacaaagga atccccgaat gcgtcggtgt   1380
tgtcaacgag ctcgctaccc gggatgcgct cgccggtacc aagacatggg acaacatcag   1440
ctactccttc aaccgcaaag aagccaaaga ccacggcgaa gggggtaaca tcgtcggtgc   1500
gcctctcaag ggaaaacgtg ttttgatcgt tgacgacgtc atcaccgctg gtaccgcgct   1560
gcgtgaagct gtcggcatta ttcaaaagga aggcggaacc gttgccggtg ttgtgttgct   1620
gttcgatcgt caggaacggg tcagtgatac ggagcagaag agtgccattg gagccgcgga   1680
gagggacctt ggaggcgata ttcctatccg tgcggtgttg gtattccagg atttgattga   1740
taagcttgga gataagattg gtcaggagga ggtgcgcagg ttggaagagt accggaacac   1800
gtacaaggct caataaatgg ctgctgtggg atgaaatggg tatattaacg atttatgcta   1860
aaaatggctg ggtggaatac tgcgaaataa atataaatca gcttgaagga tgtattttta   1920
gcgcaaagtg atagaatttt ctatgtaaat agtttgtaca ataggattac tactttatat   1980
gcgttatgcg tatacatttc taaagtgtaa ccagtttagc tgggagtaca attttaacac   2040
tcttccatca atcaggttcc agatcagttt tctatctaca atcatgactc cccagtctct   2100
actcctttca agaatgacgc gttatgttcc aagctcccct ggttgatggc ggtaacccga   2160
tatattctag ccaggtcagg tcctagtgtg aggactaaca caggcacgtc cagtatcgta   2220
gcaaatagaa tatcagcata tataagtccc ctttcccgga ccttgctcga gtcagtgact   2280
agcaggtacg tacgtaccca tcagactatc tactatctac tatgtacgga gtatatagtc   2340
ggtacttgac gcaaggcgag tctgatagag ggacaatatg cagttctgta gccaatcaat   2400
cgcggatggc agaccctcga tcgtcattgt ggatctttag cttccttatg ggcggggcgg   2460
tggttatttc agagccattt agccaatcat acatcgtagt ccgaaagtct aggattatat   2520
aggctagacc aatctactgt caaccggtaa agcgggtctc tagtctttat cccgacctcc   2580
tctctttctc tttctccgat tcgaatgtga cacatacatc tgatcaattg ataagaatac   2640
```

ggattgccgt gtacgtgggc tgacagagct gagataaaat atcctggatg tgatatgtgg 2700
cgcatccagt accgacactg tgacaggatc cgtgtactac aattcattca tcgatcgttg 2760
gctaggcaaa aagtaggcaa ggtttgcaga tcgatatccc ggtacctggc taaaatcgag 2820
acccatctac atatagtact gactcggcgt tcacttat 2858

<210> SEQ ID NO 74
<211> LENGTH: 40
<212> TYPE: DNA
<213> ORGANISM: Artificial Sequence
<220> FEATURE:
<223> OTHER INFORMATION: primer

<400> SEQUENCE: 74
cggtacccgg ggatcagcgc agaccaatgc cagaggagaa 40

<210> SEQ ID NO 75
<211> LENGTH: 25
<212> TYPE: DNA
<213> ORGANISM: Artificial Sequence
<220> FEATURE:
<223> OTHER INFORMATION: primer

<400> SEQUENCE: 75
gcgcgagttg cgcgatgaaa tttat 25

<210> SEQ ID NO 76
<211> LENGTH: 40
<212> TYPE: DNA
<213> ORGANISM: Artificial Sequence
<220> FEATURE:
<223> OTHER INFORMATION: primer

<400> SEQUENCE: 76
tcgcgcaact cgcgctgcta tgcagttgat gctactgtgt 40

<210> SEQ ID NO 77
<211> LENGTH: 30
<212> TYPE: DNA
<213> ORGANISM: Artificial Sequence
<220> FEATURE:
<223> OTHER INFORMATION: primer

<400> SEQUENCE: 77
agttgctaaa tgatcaagaa gcttcacttt 30

<210> SEQ ID NO 78
<211> LENGTH: 45
<212> TYPE: DNA
<213> ORGANISM: Artificial Sequence
<220> FEATURE:
<223> OTHER INFORMATION: primer

<400> SEQUENCE: 78
acagctggtg ctcagaagtg ggtcaccttc atctctctcc tcttc 45

<210> SEQ ID NO 79
<211> LENGTH: 25
<212> TYPE: DNA
<213> ORGANISM: Artificial Sequence
<220> FEATURE:
<223> OTHER INFORMATION: primer

<400> SEQUENCE: 79
ctgagcacca gctgttgcca gcaag 25

<210> SEQ ID NO 80
<211> LENGTH: 25
<212> TYPE: DNA
<213> ORGANISM: Artificial Sequence
<220> FEATURE:
<223> OTHER INFORMATION: primer

<400> SEQUENCE: 80
tagatcagct ttgagtgcag caaaa 25

<210> SEQ ID NO 81
<211> LENGTH: 27
<212> TYPE: DNA
<213> ORGANISM: Artificial Sequence
<220> FEATURE:
<223> OTHER INFORMATION: primer

<400> SEQUENCE: 81
gcttgtttga gaatacatga ggttgcc 27

<210> SEQ ID NO 82
<211> LENGTH: 40
<212> TYPE: DNA
<213> ORGANISM: Artificial Sequence
<220> FEATURE:
<223> OTHER INFORMATION: primer

<400> SEQUENCE: 82
tattctcaaa caagcgtcaa ttcagatcgg ctgccgcctg 40

<210> SEQ ID NO 83
<211> LENGTH: 25
<212> TYPE: DNA
<213> ORGANISM: Artificial Sequence
<220> FEATURE:
<223> OTHER INFORMATION: primer

<400> SEQUENCE: 83
ataagtgaac gccgagtcag tacta 25

<210> SEQ ID NO 84
<211> LENGTH: 40
<212> TYPE: DNA
<213> ORGANISM: Artificial Sequence
<220> FEATURE:
<223> OTHER INFORMATION: primer

<400> SEQUENCE: 84
tcggcgttca cttatcctct ttctcgccct ttcttctcaa 40

<210> SEQ ID NO 85
<211> LENGTH: 40
<212> TYPE: DNA
<213> ORGANISM: Artificial Sequence
<220> FEATURE:
<223> OTHER INFORMATION: primer

<400> SEQUENCE: 85
cgactctaga ggatcaaccg tcgatcagaa ggagcgcaat 40

<210> SEQ ID NO 86
<211> LENGTH: 40
<212> TYPE: DNA
<213> ORGANISM: Artificial Sequence
<220> FEATURE:

```
<223> OTHER INFORMATION: primer

<400> SEQUENCE: 86

acagctggtg ctcagaagtg ggtcaccttc atctctctcc                    40


<210> SEQ ID NO 87
<211> LENGTH: 40
<212> TYPE: DNA
<213> ORGANISM: Artificial Sequence
<220> FEATURE:
<223> OTHER INFORMATION: primer

<400> SEQUENCE: 87

ctcaaagctg atctacaaac caagagcagc ttgactagcg                    40
```